United States Patent
Armani et al.

(10) Patent No.: US 9,440,954 B2
(45) Date of Patent: Sep. 13, 2016

(54) DERIVATIVES OF 1-PHENYL-2-PYRIDINYL ALKYL ALCOHOLS AS PHOSPHODIESTERASE INHIBITORS

(71) Applicant: Chiesi Farmaceutici S.p.A., Parma (IT)

(72) Inventors: Elisabetta Armani, Parma (IT); Carmelida Capaldi, Parma (IT); Laura Carzaniga, Parma (IT); Oriana Esposito, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 13/909,222

(22) Filed: Jun. 4, 2013

(65) Prior Publication Data

US 2013/0324501 A1    Dec. 5, 2013

(30) Foreign Application Priority Data

Jun. 4, 2012    (EP) .................................... 12170714

(51) Int. Cl.

| | |
|---|---|
| *A61K 31/4436* | (2006.01) |
| *C07D 401/12* | (2006.01) |
| *C07D 409/12* | (2006.01) |
| *A61K 45/06* | (2006.01) |
| *A61K 31/4439* | (2006.01) |
| *A61K 31/5377* | (2006.01) |

(52) U.S. Cl.
CPC ......... *C07D 401/12* (2013.01); *A61K 31/4436* (2013.01); *A61K 31/4439* (2013.01); *A61K 31/5377* (2013.01); *A61K 45/06* (2013.01); *C07D 409/12* (2013.01)

(58) Field of Classification Search
CPC ............. A61K 31/4436; A61K 45/06; C07D 401/12; C07D 409/12
See application file for complete search history.

(56) References Cited

U.S. PATENT DOCUMENTS

| | | |
|---|---|---|
| 7,671,066 B2 | 3/2010 | Amari et al. |
| 7,820,698 B2 | 10/2010 | Rizzi et al. |
| 7,923,565 B2 | 4/2011 | Delcanale et al. |
| 7,968,724 B2 | 6/2011 | Armani et al. |
| 8,203,000 B2 | 6/2012 | Delcanale et al. |
| 8,383,826 B2 | 2/2013 | Delcanale et al. |
| 8,440,834 B2 | 5/2013 | Amari et al. |
| 2011/0144075 A1 | 6/2011 | Delcanale et al. |
| 2013/0005716 A1 | 1/2013 | Armani et al. |
| 2013/0012487 A1 | 1/2013 | Amari et al. |
| 2013/0079313 A1 | 3/2013 | Armani et al. |
| 2013/0102576 A1 | 4/2013 | Armani et al. |
| 2013/0137648 A1 | 5/2013 | Delcanale et al. |

FOREIGN PATENT DOCUMENTS

| | | |
|---|---|---|
| EP | 2 022 783 | 2/2009 |
| EP | 2 070 913 | 6/2009 |
| EP | 2 110 375 | 10/2009 |
| EP | 2 216 327 | 8/2010 |

OTHER PUBLICATIONS

U.S. Appl. No. 13/930,304, filed Jun. 28, 2013, Amari, et al.
U.S. Appl. No. 14/048,651, filed Oct. 8, 2013, Armani, et al.
European Search Report in Application No. 12170714.5, issued Aug. 7, 2012.
U.S. Appl. No. 14/161,285, filed Jan. 22, 2014, Delcanale, et al.
U.S. Appl. No. 14/164,527, filed Jan. 27, 2014, Armani, et al.
U.S. Appl. No. 14/097,693, filed Dec. 5, 2013, Armani, et al.
U.S. Appl. No. 14/097,397, filed Dec. 5, 2013, Armani, et al.
U.S. Appl. No. 14/097,586, filed Dec. 5, 2013, Armani, et al.
U.S. Appl. No. 14/097,445, filed Dec. 5, 2013, Armani, et al.
U.S. Appl. No. 14/108,731, filed Dec. 17, 2013, Amari, et al.

*Primary Examiner* — Kendra D Carter
(74) *Attorney, Agent, or Firm* — Oblon, McClelland, Maier & Neustadt, L.L.P.

(57) ABSTRACT

Derivatives of 1-phenyl-2-pyridinyl alkyl alcohols according to formula (I) are useful as inhibitors of the phosphodiesterase 4 (PDE4) enzyme.

11 Claims, No Drawings

DERIVATIVES OF 1-PHENYL-2-PYRIDINYL ALKYL ALCOHOLS AS PHOSPHODIESTERASE INHIBITORS

CROSS REFERENCES TO RELATED APPLICATIONS

This application claims priority to European Patent Application No. 12170714.5, filed on Jun. 4, 2012, which is incorporated herein by reference in its entirety.

BACKGROUND OF THE INVENTION

1. Field of the Invention

The present invention relates to inhibitors of the phosphodiesterase 4 (PDE4) enzyme. More particularly, the present invention relates to compounds that are derivatives of 1-phenyl-2-pyridinyl alkyl alcohols, methods of preparing such a compound, compositions containing such a compound, and therapeutic uses of such a compound.

2. Discussion of the Background

Airway obstruction characterizes a number of severe respiratory diseases including asthma and chronic obstructive pulmonary disease (COPD). Events leading to airway obstruction include oedema of airway walls, increased mucous production and inflammation.

Drugs for treating respiratory diseases such as asthma and COPD are currently administered through inhalation. One of the advantages of the inhalatory route over the systemic one is the possibility of delivering the drug directly at site of action, reducing systemic side-effects, thus resulting in a more rapid clinical response and a higher therapeutic ratio.

Inhaled corticosteroids are the current maintenance therapy of choice for asthma and together with bronchodilator $beta_2$-agonists for acute symptom relief, they form the mainstay of current therapy for the disease. The current management of COPD is largely symptomatic by means of bronchodilating therapy with inhaled anticholinergics and inhaled $beta_2$-adrenoceptor agonists. However, corticosteroids do not reduce the inflammatory response in COPD as they do in asthma.

Another class of therapeutic agents which has been widely investigated in view of its anti-inflammatory effects for the treatment of inflammatory respiratory diseases such as asthma and COPD is represented by the inhibitors of the enzymes phosphodiesterases (PDEs), in particular of the phosphodiesterase type 4 (hereinafter referred to as PDE4).

Various compounds acting as PDE4 inhibitors have been disclosed in the prior art. However, the usefulness of several PDE4 inhibitors of the first-generation such as rolipram and piclamilast has been limited due to their undesirable side effects. Said effects include nausea and emesis due to their action on PDE4 in the central nervous system and gastric acid secretion due to the action on PDE4 in parietal cells in the gut. The cause of said side effects has been widely investigated.

It has been found that PDE4 exists in two distinct forms representing different conformations, that were designated as high affinity rolipram binding site or HPDE4, especially present in the central nervous system and in parietal cells, and low affinity rolipram binding site or LPDE4 (Jacobitz, S et al., Mol. Pharmacol, 1996, 50, 891-899, which is incorporated herein by reference in its entirety), which is found in the immune and inflammatory cells. While both forms appear to exhibit catalytic activity, they differ with respect to their sensitivity to inhibitors. In particular compounds with higher affinity for LPDE4 appear less prone to induce side-effects such as nausea, emesis and increased gastric secretion.

The effort of targeting LPDE4 has resulted in a slight improvement in the selectivity for the second-generation PDE4 inhibitors such as roflumilast. Nonetheless, roflumilast is under dosed in order to achieve an acceptable side effect profile.

Other classes of compounds acting as PDE4 inhibitors have been disclosed in the prior art. For example, EP 1 634 606, which is incorporated herein by reference in its entirety, discloses, among others, ketone derivatives like benzofuran or 1,3-benzodioxole derivatives.

WO 94/02465, which is incorporated herein by reference in its entirety, discloses, among others, ketone derivatives of general formula

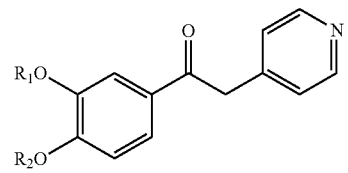

wherein $R_1$ is lower alkyl and $R_2$ may be alkyl, alkenyl, cycloalkyl, cycloalkyl, cycloalkenyl, cyclothioalkyl or cyclothioalkenyl.

WO 95/35281, which is incorporated herein by reference in its entirety, concerns tri-substituted phenyl derivatives.

WO 2009/018909, which is incorporated herein by reference in its entirety, discloses derivatives of 1-phenyl-2-pyridinyl alkyl alcohols which have general formula below reported

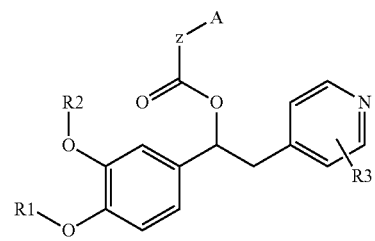

as inhibitors of phosphodiesterase 4 (PDE4) enzyme.

WO 2009/077068, which is incorporated herein by reference in its entirety, discloses further derivatives of 1-phenyl-2-pyridinyl alkyl alcohols which have general formula below reported

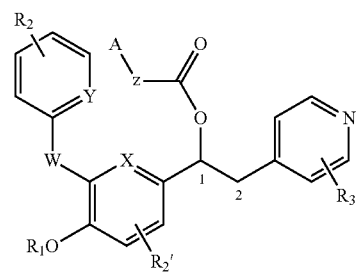

as inhibitors of phosphodiesterase 4 (PDE4) enzyme.

WO 2010/089107, which is incorporated herein by reference in its entirety, discloses further derivatives of 1-phenyl-2-pyridinyl alkyl alcohols which have general formula below reported

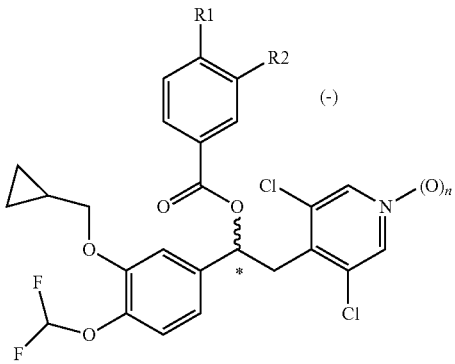

as inhibitors of phosphodiesterase 4 (PDE4) enzyme.

Although several PDE4 inhibitors have been disclosed so far as above reported, there is still a need for further PDE4 inhibitors. Particularly, there is still a need for further PDE4 inhibitors endowed with a high affinity for PDE4 enzyme and which would show an appropriate developability profile as an inhalation treatment for example in terms of reduced side effects. Such reduction of side effects may be achieved, by way of example, through a low systemic exposure of the drug; an appropriate profile in terms of some pharmacokinetic characteristics, especially high or moderate metabolic clearance, may be thus key to this goal. The present invention addresses the above-mentioned need by providing the compounds of the invention.

SUMMARY OF THE INVENTION

Accordingly, it is one object of the present invention to provide novel compounds which are inhibitors of the phosphodiesterase 4 (PDE4) enzyme.

It is another object of the present invention to provide novel methods of preparing such a compound.

It is another object of the present invention to provide novel compositions which contain such a compound.

It is another object of the present invention to provide novel therapeutic uses of such a compound.

These and other objects, which will become apparent during the following detailed description, have been achieved by the inventors' discovery that compounds of general formula (I)

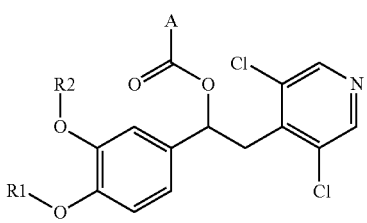

(I)

wherein:
$R_1$ and $R_2$ are different or the same and are independently selected from the group consisting of:
H;
$(C_1-C_6)$alkyl, optionally substituted by one or more substituents selected from $(C_3-C_7)$cycloalkyl or $(C_5-C_7)$cycloalkenyl;
$(C_1-C_6)$haloalkyl
$(C_3-C_7)$cycloalkyl;
$(C_5-C_7)$cycloalkenyl;
$(C_2-C_6)$alkenyl; and
$(C_2-C_6)$alkynyl;

A is a monocyclic heteroaryl ring system, selected from the group consisting of radicals (a), (b), (c) and (d):

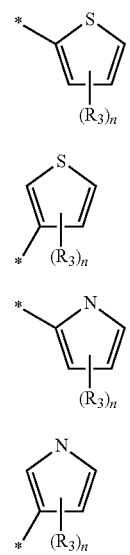

* indicates the position of attachment to the remainder of the molecule;
n is 0, 1 or 2;
$R_3$ is an optional substituent which, at each occurrence, is independently:
$(C_1-C_6)$alkyl optionally substituted by one or more $(C_3-C_7)$cycloalkyl;
$(C_1-C_6)$haloalkyl;
$OR_4$ wherein $R_4$ is selected from the group consisting of H, $(C_1-C_{10})$alkyl optionally substituted by $(C_3-C_7)$cycloalkyl, $(C_1-C_6)$haloalkyl, $(C_3-C_7)$cycloalkyl;
a halogen atom;
a group $-NR_5SO_2R_6$ wherein
$R_5$ is selected in the group consisting of hydrogen; $(C_1-C_6)$alkyl; $(C_1-C_6)$alkyl which is substituted by a group $-NR_7R_8$ wherein $R_7$ and $R_8$ are independently H, $(C_1-C_6)$alkyl, or together with the nitrogen atom to which they are attached form a $(C_5-C_7)$heterocycloalkyl group; $(C_1-C_6)$alkyl which is substituted by an heteroaryl group; and
$R_6$ is $(C_1-C_4)$alkyl optionally substituted by $(C_3-C_7)$cycloalkyl; or a phenyl ring optionally substituted with one or two halogen atoms, hydroxy, $(C_1-C_4)$alkyl or $(C_1-C_4)$alkoxy groups or with a group $-C(O)NR_9R_{10}$ wherein $R_9$ and $R_{10}$ are independently hydrogen, $(C_1-C_4)$alkyl groups, or together with the nitrogen atom to which they are attached form a $(C_5-C_7)$ heterocycloalkyl group;
a group $-SO_2R_{11}$ wherein
$R_{11}$ is selected from $(C_1-C_6)$alkyl; a phenyl ring which is optionally substituted with one or two groups selected in the list consisting of: halogen atom, hydroxyl, $(C_1-C_4)$alkyl, $(C_1-C_4)$alkoxy, a $-C(O)NR_{12}R_{13}$ group, wherein $R_{12}$ and $R_{13}$ are independently hydrogen, $(C_1-C_4)$alkyl groups, or together with the nitrogen atom to which they are attached form a $(C_5-C_7)$heterocycloalkyl group, and a group —$NR_{14}R_{15}$, wherein $R_{14}$ and $R_{15}$ are independently hydrogen, $(C_1-C_4)$alkyl groups, or together with the nitrogen atom to which they are attached form a $(C_5-C_7)$ heterocycloalkyl group;

a group —$C(O)R_{16}$ wherein $R_{16}$ is a phenyl ring which is optionally substituted with one or two groups selected in the list consisting of: halogen atom, hydroxyl, $(C_1-C_4)$alkyl, $(C_1-C_4)$alkoxy, a —$C(O)NR_{23}R_{24}$ group wherein $R_{23}$ and $R_{24}$ are independently hydrogen, $(C_1-C_4)$ alkyl groups, or together with the nitrogen atom to which they are attached form a $(C_5-C_7)$heterocycloalkyl group, and a group —$NR_{25}R_{26}$, wherein $R_{25}$ and $R_{26}$ are independently hydrogen, $(C_1-C_4)$ alkyl groups, or together with the nitrogen atom to which they are attached form a $(C_5-C_7)$ heterocycloalkyl group; or a group —$SO_2NR_{17}R_{18}$ wherein $R_{17}$ is H or $(C_1-C_6)$alkyl; and $R_{18}$ is selected from hydrogen; $(C_1-C_6)$alkyl; $(C_1-C_6)$alkyl which is substituted by a group —$NR_{19}R_{20}$ wherein $R_{19}$ and $R_{20}$ are independently H or $(C_1-C_6)$alkyl, or together with the nitrogen atom to which they are attached form a $(C_5-C_7)$ heterocycloalkyl group; a phenyl ring optionally substituted with one or two halogen atoms, hydroxy, $(C_1-C_4)$alkyl or $(C_1-C_4)$alkoxy groups or with a group —$C(O)NR_{21}R_{22}$ wherein $R_{21}$ and $R_{22}$ are independently hydrogen, $(C_1-C_4)$ alkyl groups, or together with the nitrogen atom to which they are attached form a $(C_5-C_7)$ heterocycloalkyl group;

and pharmaceutically acceptable salts and N-oxides on the pyridine ring thereof, are useful as phosphodiesterase 4 (PDE4) inhibitors.

The present invention also encompasses the pharmaceutically acceptable salts and/or solvates of compounds of formula (I).

The present invention further involves the corresponding N-oxides on the pyridine ring of compounds of formula (I) or of pharmaceutically acceptable salts and/or solvates thereof.

Hereinafter, compounds of formula (I), N-oxides on the pyridine ring, embodiments thereof and their pharmaceutically acceptable salts and solvates, defined in any aspect of the invention (except intermediate compounds described in the chemical processes) are referred to as "compounds of the invention".

The present invention further comprises a process for the preparation of compounds of the invention.

The present invention also provides pharmaceutical compositions of compounds of the invention either alone or in combination, in admixture with one or more pharmaceutically acceptable carriers.

The present invention further provides a suitable device for the delivery of the pharmaceutical compositions of compounds of the invention.

In a further aspect the present invention provides the use of the compounds of the invention as a medicament.

In one aspect the present invention provides the use of the compounds of the invention for the manufacture of a medicament.

In particular the present invention provides the use of the compounds of the invention for the prevention and/or treatment of any disease characterized by phosphodiesterase 4 (PDE4) overactivity and/or wherein an inhibition of PDE4 activity is desirable.

In particular the compounds of the invention alone or combined with other active ingredients may be administered for the prevention and/or treatment of a disease of the respiratory tract characterized by airway obstruction such as asthma and COPD.

In a further aspect the present invention provides the use of compounds of the invention for the preparation of a medicament for the prevention and/or treatment of any disease characterized by phosphodiesterase 4 (PDE4) overactivity and/or wherein an inhibition of PDE4 activity is desirable.

Moreover the present invention provides a method for prevention and/or treatment of any disease wherein PDE4 inhibition is desirable, said method comprises administering to a patient in need of such treatment a therapeutically effective amount of a compound of the invention.

DETAILED DESCRIPTION OF THE PREFERRED EMBODIMENTS

The term "halogen atoms" as used herein includes fluorine, chlorine, bromine, and iodine, preferably chlorine.

The term "$(C_1-C_x)$alkyl" where x is an integer greater than 1, refers to straight-chained and branched alkyl groups wherein the number of constituent carbon atoms is in the range 1 to x. Particular alkyl groups are methyl, ethyl, n-propyl, isopropyl and t-butyl.

The term "$(C_1-C_x)$alkoxyl" where x is an integer greater than 1, refers to straight-chained and branched alkoxy groups wherein the number of constituent carbon atoms is in the range 1 to x. Particular alkyl groups are methoxyl, ethoxyl, n-propoxyl, isopropoxyl and t-butoxyl.

The expressions "$(C_1-C_x)$haloalkyl" refer to the above defined "$(C_1-C_x)$alkyl" groups wherein one or more hydrogen atoms are replaced by one or more halogen atoms, which can be the same or different from each other. Examples of said $(C_1-C_x)$haloalkyl groups may thus include halogenated, poly-halogenated and fully halogenated alkyl groups wherein all of the hydrogen atoms are replaced by halogen atoms, e.g. trifluoromethyl or difluoro methyl groups.

The term "$(C_3-C_y)$cycloalkyl", where y is an integer greater than 3, refers to saturated cyclic hydrocarbon groups containing from 3 to y ring carbon atoms. Examples include cyclopropyl, cyclobutyl, cyclopentyl, cyclohexyl, and cycloheptyl.

The derived expression "$(C_5-C_z)$ heterocycloalkyl" refers to saturated monocyclic $(C_5-C_z)$cycloalkyl groups, wherein z is an integer greater than 5 in which at least one ring carbon atom is replaced by a heteroatom (e.g. N, NH, S or O). Not limiting examples of $(C_5-C_z)$heterocycloalkyl are represented by pyrrolidinyl, thiazolidinyl, piperazinyl, piperidinyl, morpholinyl, thiomorpholinyl.

The term "$(C_2-C_x)$alkenyl" refers to straight or branched, conjugated or not conjugated, carbon chains with one or more double bonds, in cis or trans configuration, wherein the number atoms is in the range 2 to x.

By way of analogy, the term "$(C_5-C_y)$cycloalkenyl", where y is an integer greater than 5, refers to cyclic hydrocarbon groups containing from 5 to y ring carbon atoms and one or two double bonds.

The term "$(C_2-C_x)$alkynyl" refers to straight or branched carbon chains with one or more triple bonds wherein the number atoms is in the range 2 to x.

The expression "aryl" refers to mono or bi-cyclic ring systems which have 6 to 10 ring atoms, wherein at least one ring is aromatic.

The expression "heteroaryl" refers to mono or bi-cyclic ring systems with 5 to 11 ring atoms, in which at least one ring is aromatic and in which at least one ring atom is a heteroatom (e.g. N, NH, S or O).

Examples of suitable monocyclic aryl or heteroaryl systems include, for instance, phenyl, thiophene (thiophenyl), benzene (phenyl), pyrrole (pyrrolyl), pyrazole (pyrazolyl), imidazole (imidazolyl), isoxazole (isoxazolyl), oxazole (oxaolyl), isothiazole (isothiazoyl), thiazole (thiazolyl), pyridine (pyridinyl), imidazolidine (imidazolidinyl), furan (furanyl) radicals and the like.

Examples of suitable aryl or heteroaryl bicyclic systems include naphthalene (naphthyl), biphenylene (biphenylenyl), purine (purinyl), pteridine (pteridinyl), benzotriazole (benzotriazolyl), quinolone (quinolinyl), isoquinoline (isoquinolinyl), indole (indolyl), isoindole (isoindolyl), benzothiophene (benzothiophenyl), dihydrobenzo dioxin, dihydrobenzo dioxepin, benzo oxazin radicals and the like.

The expression "heteroarylcarbonyl" refers to heteroarylCO— groups wherein the group "heteroaryl" has the meaning above defined.

As used herein, the expression "ring system" refers to mono- or bicyclic ring systems which may be saturated, partially unsaturated or unsaturated, such as aryl, $(C_3-C_8)$ cycloalkyl, $(C_3-C_7)$ heterocycloalkyl or heteroaryl.

The invention is directed to a class of compounds acting as inhibitors of the phosphodiesterase 4 (PDE4) enzyme.

Said class of compounds inhibits the conversion of cyclic nucleotides, in particular cyclic adenosine monophosphate (cAMP), into their inactive 5'-mononucleotide forms.

In the airways, the physiological responses to elevated intracellular levels of cyclic nucleotides, in particular of cAMP, lead to the suppression of the activity of immune and pro-inflammatory cells such as mast cells, macrophages, T lymphocytes, eosinophils and neutrophils, resulting in a decrease of the release of inflammatory mediators which include cytokines such as IL-1, IL-3 and tumor necrosis factor-alpha (TNF-α). It also leads to an airway smooth muscle relaxation and a decrease in oedema.

The present invention relates to derivatives of 1-phenyl-2-pyridinyl alkyl alcohols of general formula (I), pharmaceutically acceptable salts and N-oxides on the pyridine ring thereof

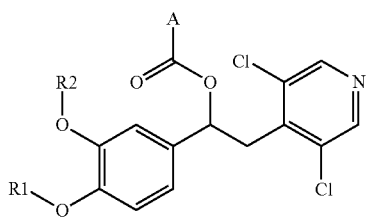

wherein $R_1$, $R_2$ and A are as above defined.

The term "pharmaceutically acceptable salts", as used herein, refers to derivatives of compounds of formula (I) wherein the parent compound is suitably modified by converting any of the free acid or basic group, if present, into the corresponding addition salt with any base or acid conventionally intended as being pharmaceutically acceptable.

Suitable examples of said salts may thus include mineral or organic acid addition salts of basic residues such as amino groups, as well as mineral or organic addition salts of acid residues such as carboxylic groups.

Cations of inorganic bases which can be suitably used to prepare salts within the invention comprise ions of alkali or alkaline earth metals such as potassium, sodium, calcium or magnesium.

Those obtained by reacting the main compound, functioning as a base, with an inorganic or organic acid to form a salt include, for example, salts of hydrochloric acid, sulfuric acid, phosphoric acid, methane sulfonic acid, camphor sulfonic acid, oxalic acid, maleic acid, succinic acid, and citric acid.

It will be apparent to those skilled in the art that compounds of general formula (I) at least contain one stereogenic center, namely represented by the carbon atom (1) with an asterisk below, and therefore exist as optical stereoisomers:

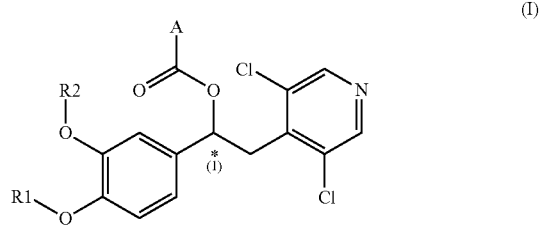

Where the compounds according to the present invention have at least one stereogenic center, they may accordingly exist as enantiomers. Where the compounds according to the invention possess two or more stereogenic centers, they may additionally exist as diastereoisomers. It is to be understood that all such isomers and mixtures thereof in any proportion are encompassed within the scope of the present invention.

In a preferred embodiment, the present invention is directed to compounds of formula (I)', which are compounds of formula (I) as above defined where the absolute configuration of carbon (1) is that shown below:

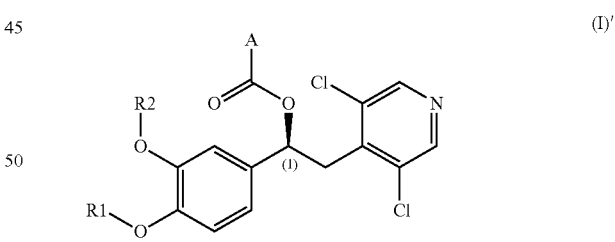

The absolute configuration for carbon (1) is assigned on the basis of Cahn-Ingold-Prelog nomenclature based on groups' priorities.

In one preferred embodiment, for compounds of formula (I), absolute configuration at carbon (1) is (S).

It is to be understood that all preferred groups or embodiments described below for compounds of formula (I) may be combined among each other and apply to compounds of formula (I)', (IA), (IB), (IC), (ID), and (IE) as well mutatis mutandis.

In a preferred embodiment, compounds of the invention are N-oxides derivatives on the pyridine ring of compounds of formula (I) or pharmaceutically acceptable salts thereof.

In one preferred embodiment, $R_1$ is $(C_1-C_6)$haloalkyl or $(C_1-C_6)$alkyl.

In another preferred embodiment, $R_2$ is $(C_1-C_6)$alkyl which is optionally substituted by $(C_3-C_7)$cycloalkyl.

In a further preferred embodiment, $R_1$ is $(C_1-C_6)$haloalkyl and $R_2$ is $(C_1-C_6)$alkyl which is substituted by $(C_3-C_7)$cycloalkyl.

In one preferred embodiment, n is zero. In another preferred embodiment, n is 1 or 2. In a further preferred embodiment, n is 1.

In one preferred embodiment, A is a group (a) or (b). In another preferred embodiment, A is a group (a).

In one preferred embodiment, A is a group (c) or (d). In another preferred embodiment, A is a group (c).

In a further preferred embodiment, $R_1$ is $(C_1-C_6)$haloalkyl, $R_2$ is $(C_1-C_6)$alkyl which is substituted by $(C_3-C_7)$cycloalkyl and A is a group (a).

In a preferred embodiment, $R_3$ is an optional substituent which, at each occurrence, is selected from the group consisting of:

$(C_1-C_6)$alkyl;

$OR_4$ wherein $R_4$ is hydrogen or $(C_1-C_{10})$alkyl;

halogen atoms;

a group $—NR_5SO_2R_6$ wherein $R_5$ is selected in the group consisting of hydrogen; $(C_1-C_6)$alkyl; $(C_1-C_6)$alkyl which is substituted by a group $—NR_7R_8$ wherein $R_7$ and $R_8$ are independently H, $(C_1-C_6)$alkyl, or together with the nitrogen atom to which they are attached form a $(C_5-C_7)$heterocycloalkyl group; $(C_1-C_6)$alkyl which is substituted by an heteroaryl group; and $R_6$ is $(C_1-C_4)$alkyl optionally substituted by $(C_3-C_7)$cycloalkyl; or a phenyl ring optionally substituted with one or two halogen atoms, hydroxy, $(C_1-C_4)$alkyl or $(C_1-C_4)$alkoxy groups or with a group $—C(O)NR_9R_{10}$ wherein $R_9$ and $R_{10}$ are independently hydrogen, $(C_1-C_4)$alkyl groups, or together with the nitrogen atom to which they are attached form a $(C_5-C_7)$ heterocycloalkyl group; a group $—SO_2R_{11}$ wherein $R_{11}$ is selected from $(C_1-C_6)$alkyl; a phenyl ring which is optionally substituted with one or two groups selected in the list consisting of: halogen atom, hydroxyl, $(C_1-C_4)$alkyl, $(C_1-C_4)$alkoxy, a $—C(O)NR_{12}R_{13}$ group, wherein $R_{12}$ and $R_{13}$ are independently hydrogen, $(C_1-C_4)$alkyl groups, or together with the nitrogen atom to which they are attached form a $(C_5-C_7)$heterocycloalkyl group, and a group $—NR_{14}R_{15}$, wherein $R_{14}$ and $R_{15}$ are independently hydrogen, $(C_1-C_4)$alkyl groups, or together with the nitrogen atom to which they are attached form a $(C_5-C_7)$heterocycloalkyl group;

a group $—C(O)R_{16}$ wherein $R_{16}$ is a phenyl ring a group $—SO_2NR_{17}R_{18}$ wherein $R_{17}$ is H or $(C_1-C_6)$alkyl; and $R_{18}$ is selected from hydrogen; $(C_1-C_6)$alkyl; $(C_1-C_6)$alkyl which is substituted by a group $—NR_{19}R_{20}$ wherein $R_{19}$ and $R_{20}$ are independently H or $(C_1-C_6)$alkyl, or together with the nitrogen atom to which they are attached form a $(C_5-C_7)$heterocycloalkyl group; a phenyl ring optionally substituted with one or two halogen atoms, hydroxy, $(C_1-C_4)$alkyl or $(C_1-C_4)$alkoxy groups or with a group $—C(O)NR_{21}R_{22}$ wherein $R_{21}$ and $R_{22}$ are independently hydrogen, $(C_1-C_4)$alkyl groups, or together with the nitrogen atom to which they are attached form a $(C_5-C_7)$heterocycloalkyl group.

In a preferred embodiment, n is 0, 1 or 2 and $R_3$ is selected from the group consisting of:

$(C_1-C_6)$alkyl;

$OR_4$ wherein $R_4$ is $(C_1-C_{10})$alkyl;

a group $—NR_5SO_2R_6$, wherein $R_5$ and $R_6$ are as defined for compounds of formula (I);

a group $—SO_2NR_{17}R_{18}$, wherein $R_{17}$ and $R_{18}$ are as defined for compounds of formula (I); and a group $—SO_2R_{11}$, wherein $R_{11}$ is as defined for compounds of formula (I).

In one embodiment, compounds of formula (IA) are provided wherein $R_1$, $R_2$, $R_3$ and n have meanings as described in formula (I):

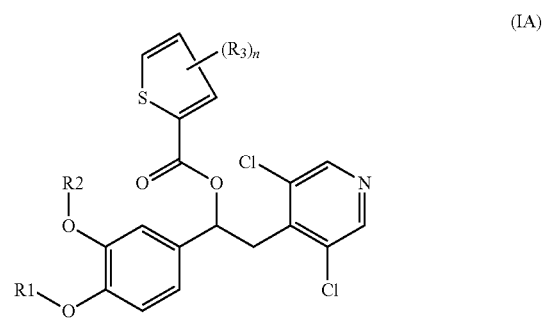

(IA)

In another embodiment, compounds of formula (IB) are provided wherein $R_1$, $R_2$, $R_3$ and n have meanings as described in formula (I):

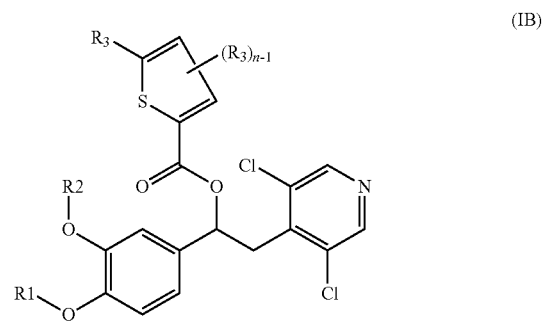

(IB)

In one embodiment, compounds of formula (IC) are provided wherein $R_1$, $R_2$, $R_3$ and n have meanings as described in formula (I):

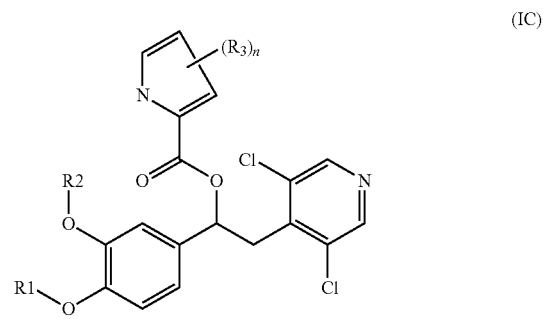

(IC)

In another embodiment, compounds of formula (ID) are provided wherein $R_1$, $R_2$, $R_3$ and n have meanings as described in formula (I):

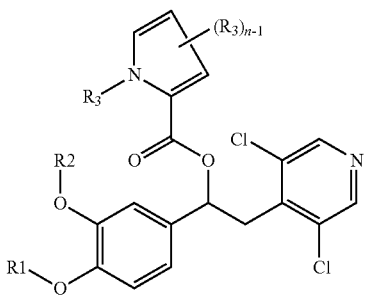

(ID)

In another embodiment, compounds of formula (IE) are provided wherein $R_1$, $R_2$, $R_3$ and n have meanings as described in formula (I):

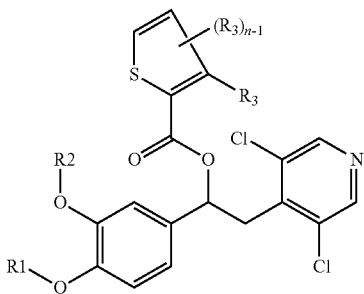

(IE)

In one embodiment, a compound of formula (I) is selected from the group consisting of:
(S)-3,5-dichloro-4-(2-(3-(cyclopropylmethoxy)-4-(difluoromethoxy)-phenyl)-2-(thiophene-3-carbonyloxy)ethyl)pyridine 1-oxide;
(S)-3,5-dichloro-4-(2-(3-(cyclopropylmethoxy)-4-(difluoromethoxy)-phenyl)-2-(thiophene-2-carbonyloxy)ethyl)pyridine 1-oxide;
(S)-4-(2-(1H-pyrrole-2-carbonyloxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)-phenyl)-2-(5-methylthiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-methoxythiophene-2-carbonyloxy)ethyl)pyridine 1-oxide;
(S)-3,5-dichloro-4-(2-(5-chlorothiophene-2-carbonyloxy)-2-(3-(cyclopropylmethoxy)-4-(difluoromethoxy)phenyl)ethyl)pyridine 1-oxide;
(S)-3,5-dichloro-4-(2-(3-chloro-4-(methyl sulfonyl)thiophene-2-carbonyloxy)-2-(3-(cyclopropylmethoxy)-4-(difluoromethoxy)phenyl)-ethyl)pyridine 1-oxide;
(S)-3,5-dichloro-4-(2-(3-(cyclopropylmethoxy)-4-(difluoromethoxy)-phenyl)-2-(5-methoxythiophene-2-carbonyloxy)ethyl)pyridine 1-oxide;
(S)-3,5-dichloro-4-(2-(3-(cyclopropylmethoxy)-4-(difluoromethoxy)-phenyl)-2-(4,5-dimethylthiophene-2-carbonyloxy)ethyl)pyridine 1-oxide;
(S)-3,5-dichloro-4-(2-(3-chlorothiophene-2-carbonyloxy)-2-(3-(cyclopropylmethoxy)-4-(difluoromethoxy)phenyl)ethyl)pyridine 1-oxide;
(S)-3,5-dichloro-4-(2-(3-(cyclopropylmethoxy)-4-(difluoromethoxy)-phenyl)-2-(3-(N-methylsulfamoyl)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-(N-methyl-N-(2-morpholinoethyl)sulfamoyl)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-(N-(2-morpholinoethyl)methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-(methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(2-morpholinoethyl)methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(4-(methylsulfonamido)thiophene-2-carbonyloxy)ethyl)pyridine 1-oxide;
(S)-3,5-dichloro-4-(2-(4-(4-chlorophenylsulfonyl)thiophene-3-carbonyloxy)-2-(3-(cyclopropylmethoxy)-4-(difluoromethoxy)phenyl)ethyl)-pyridine 1-oxide;
(S)-4-(2-(3-benzoylthiophene-2-carbonyloxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)-phenyl)-2-(3-(3-(dimethylcarbamoyl)phenylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(3-(dimethylcarbamoyl)phenyl)sulfamoyl)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(4-(dimethylcarbamoyl)phenyl)sulfamoyl)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(pyridin-3-ylmethyl)methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(2-(pyrrolidin-1-yl)ethyl) methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(4-methoxy-5-(N-(2-morpholinoethyl)methylsulfonamido)-thiophene-2-carbonyloxy)ethyl)pyridine 1-oxide;
(S)-3,5-dichloro-4-(2-(3-(cyclopropylmethoxy)-4-(difluoromethoxy)-phenyl)-2-(1-(phenylsulfonyl)-1H-pyrrole-2-carbonyloxy)ethyl)pyridine 1-oxide;
(S)-3,5-dichloro-4-(2-(3-(cyclopropylmethoxy)-4-(difluoromethoxy)-phenyl)-2-(1-(3-(dimethylcarbamoyl)phenylsulfonyl)-1H-pyrrole-2-carbonyloxy)ethyl)pyridine 1-oxide;
(S)-4-(2-(1-(4-aminophenylsulfonyl)-1H-pyrrole-2-carbonyloxy)-2-(3-(cyclopropylmethoxy)-4-(difluoromethoxy)phenyl)ethyl)-3,5-dichloropyridine 1-oxide;
(S)-3,5-dichloro-4-(2-(5-(1-cyclopropyl-N-(2-morpholinoethyl)-methylsulfonamido)thiophene-2-carbonyloxy)-2-(3-(cyclopropylmethoxy)-4-(difluoromethoxy)phenyl)ethyl)pyridine 1-oxide;
(S)-3,5-dichloro-4-(2-(5-(1-cyclopropyl-N-(2-(pyrrolidin-1-yl)ethyl)-methylsulfonamido)thiophene-2-carbonyloxy)-2-(3-(cyclopropylmethoxy)-4-(difluoromethoxy)phenyl)ethyl)pyridine 1-oxide;

(S)-3,5-dichloro-4-(2-(3-(cyclopropylmethoxy)-4-(difluoromethoxy)-phenyl)-2-(1-(3-(dimethylcarbamoyl)-4-hydroxyphenylsulfonyl)-1H-pyrrole-2-carbonyloxy)ethyl)pyridine 1-oxide;
(S)-3,5-dichloro-4-(2-(3-(cyclopropylmethoxy)-4-(difluoromethoxy)-phenyl)-2-(1-(3-(dimethylcarbamoyl)-4-methoxyphenylsulfonyl)-1H-pyrrole-2-carbonyloxy)ethyl)pyridine 1-oxide;
(S)-3,5-dichloro-4-(2-(3-(cyclopropylmethoxy)-4-(difluoromethoxy)-phenyl)-2-(1-methyl-4-(phenylsulfonamido)-1H-pyrrole-2-carbonyloxy)ethyl)pyridine 1-oxide;
(S)-3,5-dichloro-4-(2-(3-(cyclopropylmethoxy)-4-(difluoromethoxy)-phenyl)-2-(4-(3-(dimethylcarbamoyl)phenylsulfonamido)-1-methyl-1H-pyrrole-2-carbonyloxy)ethyl)pyridine 1-oxide;
(S)-3,5-dichloro-4-(2-(3,4-dimethoxyphenyl)-2-(thiophene-2-carbonyloxy)ethyl)pyridine 1-oxide;
(S)-3,5-dichloro-4-(2-(4-(difluoromethoxy)-3-methoxyphenyl)-2-(thiophene-2-carbonyloxy)ethyl)pyridine 1-oxide;
and pharmaceutically acceptable salts or solvates thereof.

In one aspect of the present invention, a process for the preparation of compounds of the invention is provided, according to general synthetic routes a) or b) reported in the General Scheme below:

TABLE A

| Example (Synthetic Scheme) | Route |
|---|---|
| 1, 3, 4, 6, 8, 9, 10, 11, 12, 13, 14, 15 | a) |
| 5 | b) |
| 2, 7, | Modified a) |

Processes which can be used and are described and reported in the examples and Schemes should not be viewed as limiting the scope of the synthetic methods available for the preparation of the compounds of the invention.

The N-oxides on the 2-pyridinyl ring of the compounds of general formula (I) may be prepared according to methods available in the literature and well known to the skilled person. For instance they may be prepared by dissolving the compound of general formula (I) in CH$_2$Cl$_2$ or CHCl$_3$, then adding an oxidizing agent such as m-chloro perbenzoic acid (mCPBA) to the resulting solution. Other oxidizing agents which may be used are hydrogen peroxide, perbenzoic acid, and peracetic acid.

General Scheme

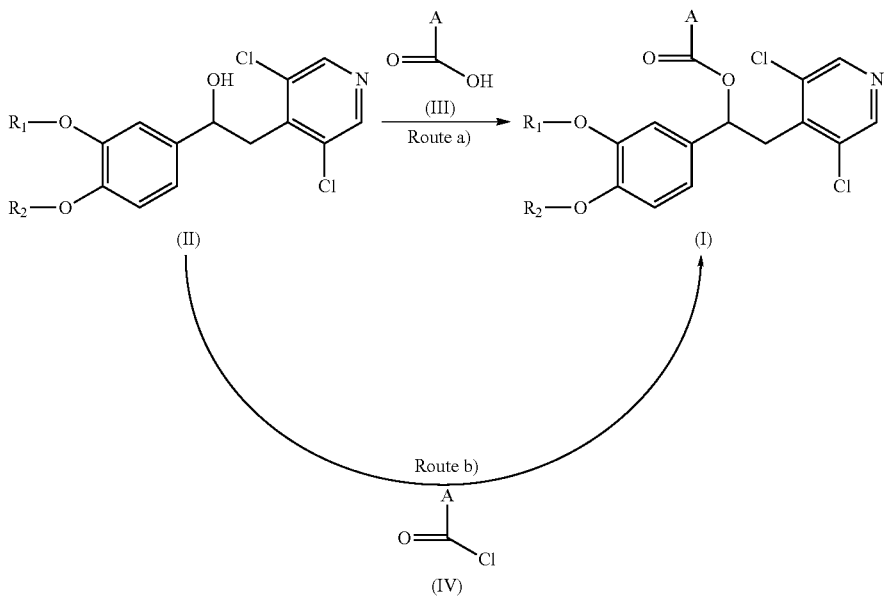

The skilled person may introduce, where appropriate, suitable variations to the conditions specifically described in the examples in order to adapt the synthetic routes to the provision of further compounds of the invention. Such variations may include, but are not limited to, use of appropriate starting materials to generate different compounds, changes in the solvent and temperature of reactions, replacements of reactants with analogous chemical role, introduction or removal of protection/deprotection stages of functional groups sensitive to reaction conditions and reagents.

Also, introduction or removal of specific synthetic steps oriented to further functionalize the chemical scaffold may be contemplated and is included within the scope of the present invention.

In Table A below, reference is made to specific synthetic Schemes where Routes a) or b) and variants thereof are better detailed and which are reported in the examples.

Alternatively, in particular for those compounds where a functional group sensitive to oxidation is present, the corresponding N-oxides are prepared by carrying out the oxidation step before further functional groups are introduced, for example on compounds of formula (II), thus generating compounds of formula (V).

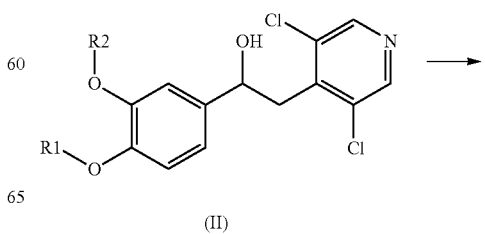

-continued

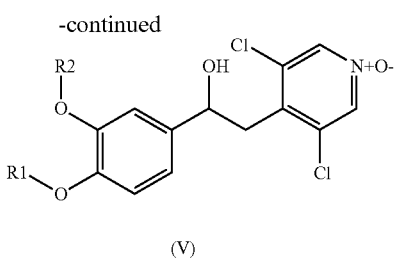

(V)

In a preferred embodiment, the process for preparation of compounds of formula (I) is performed starting from N-oxide compound of formula (V) on the pyridine ring, thus allowing the preparation of compound of formula (I) in the form of N-oxides on the pyridine ring.

Compounds used as starting materials or intermediates may be commercially available, their preparation may be specifically described in the literature or they may be prepared according to methods available in the literature and well known to the person skilled in the art. In some instances, procedures for the preparation of intermediates may be also provided in the examples, such as, for example, in Schemes 1, 2, 3, 4, 5, 7, 8, 9, 10, 11, 12, 13, 14, 15.

Compounds of formula (II) and (V) may also be prepared as described in International Patent Application WO 2009/018909, which is incorporated herein by reference in its entirety.

The process described is particularly advantageous as it is susceptible of being properly modulated, through any proper variant known to the skilled person, so as to obtain any of the desired compounds of the invention. Such variants are comprised within the scope of the present invention.

From all of the above, it should be clear to the skilled person that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known to those skilled in the art (see, for a general reference, T. W. Green; Protective Groups in Organic Synthesis (Wiley, N.Y. 1981) which is incorporated herein by reference in its entirety).

Likewise, selective protection and deprotection of any of the said groups, for instance including carbonyl, hydroxyl, or amino groups, may be accomplished according to very well-known methods commonly employed in organic synthetic chemistry.

Optional salification of the compounds of formula (I) or N-oxides on the pyridine ring thereof may be carried out by properly converting any of the free acidic or amino groups into the corresponding pharmaceutically acceptable salts. In this case too, the operative conditions being employed for the optional salification of the compounds of the invention are all within the ordinary knowledge of the skilled person.

From all of the above, it should be clear to the skilled person that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Schemes, for compounds of formula (II) to (XVI), unless otherwise indicated, groups A, n, $R_1$, $R_2$ and $R_3$ have the same meanings as described for compounds of formula (I) above.

Route a)

Compounds of formula (I) may be prepared according to Scheme A below reported by reaction of a compound of formula (II), with an appropriate compound of formula (III).

Scheme A

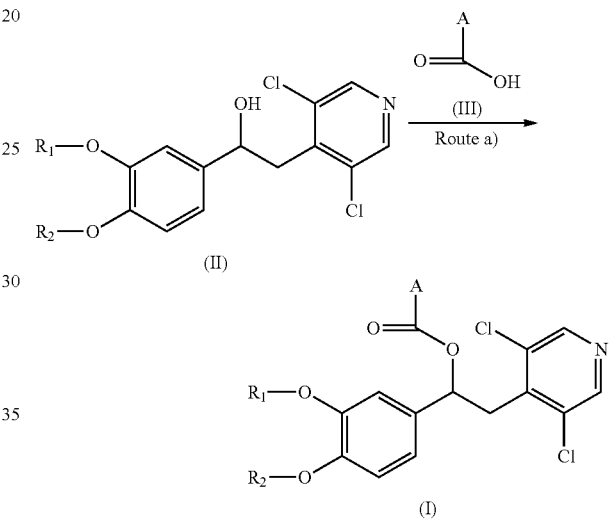

Typical reaction conditions comprise reacting a compound of formula (II) with a compound of formula (III) in a suitable polar aprotic solvent, such as DMF, chloroform, acetonitrile or DCM, in the presence of an appropriate condensing agent such as EDC, DCC or CDI and of an appropriate catalyst such as DMAP, HBTU, HOBT, 4-pyrrolidinopyridine (4-PPY) or other 4-alkylamino pyridine at room temperature.

Route b)

Compounds of formula (I) may be prepared according to Scheme B below reported by reaction of a compound of formula (II), with an appropriate compound of formula (IV).

Scheme B

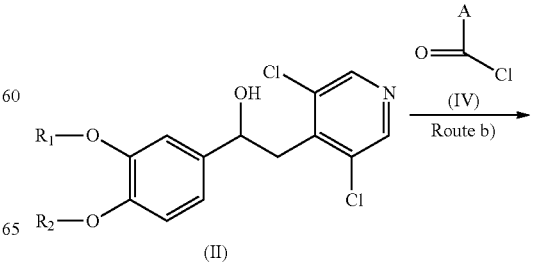

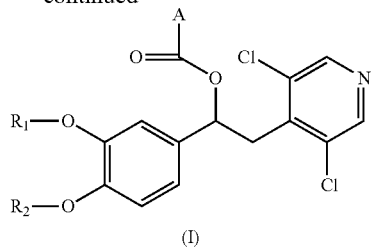

(I)

Typical reaction conditions comprise reacting a compound of formula (II) with a compound of formula (IV) in a suitable polar aprotic solvent, such as DCM or chloroform, in the presence an appropriate base, such as DMAP, Py, TEA or DIPEA at an appropriate temperature such as, for example, RT.

Compounds of formula (Ma), i.e. compounds of formula (III) wherein n is 1 or 2, $R_3$ is at one occurrence a group $-SO_2NR_{17}R_{18}$, may be prepared according to Scheme C below reported by reaction of a compound of formula (VI), wherein PG is a suitable carboxylic protecting group, with an appropriate compound of formula $R_{17}R_{18}NH$, followed by deprotection of carboxyl group under suitable conditions.

Scheme C

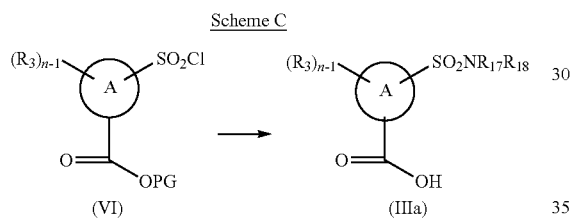

Typical reaction conditions comprise reacting a compound of formula (VI) with a compound of formula $R_{17}R_{18}NH$ in a suitable polar aprotic solvent, such as DMF, DMSO, acetonitrile, DCM, THF or chloroform, in the presence an appropriate base, such as DMAP, TEA, Methylamine or DIPEA at an appropriate temperature such as, for example, RT, or in a neat base such as pyridine at an appropriate temperature as, for example, 0 degrees.

Compounds of formula (IIIb), i.e. compounds of formula (III) wherein A is a group (a) or (b), n is 1 or 2, $R_3$ is at one occurrence a group $-NR_5SO_2R_6$, may be prepared according to Scheme D below reported by reaction of a compound of formula (VII), wherein PG is a suitable carboxylic protecting group, with an appropriate sulfonylating agent of formula $R_6SO_2X$, wherein X is a leaving group such as chlorine, followed by deprotection of carboxyl group under suitable conditions.

Scheme D

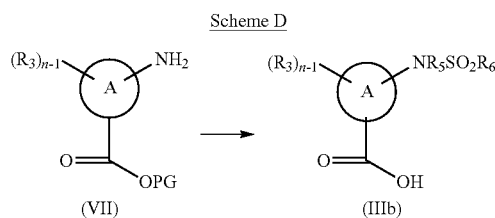

Typical reaction conditions comprise reacting a compound of formula (VII) with a compound of formula $R_6SO_2X$ in a suitable polar aprotic solvent, such as DMF, DMSO, acetonitrile, DCM or chloroform, in the presence an appropriate base, such as DMAP, TEA or DIPEA at an appropriate temperature such as, for example, RT, or in a neat base such as pyridine at an appropriate temperature as, for example, 0 degrees.

Compounds of formula (IIIb1), i.e. compounds of formula (IIIb) wherein $R_5$ is different from hydrogen, may be prepared according to Scheme D above reported by providing an intermediate alkylation step before deprotection of the carboxylic group takes place, according to Scheme E reported below. Compounds of formula (VIII) (wherein n is 1 or 2, A is a group (a) or (b) and the other groups are defined as for compounds of formula (I)) are reacted with a suitable alkylating agent of formula $R_5LG$ (wherein LG is a suitable leaving group such as halogen or mesylate or tosylate or brosylate) to give compounds of formula (IX) (wherein n is 1 or 2 and the other groups are defined as for compounds of formula (I)), as below reported in Scheme E Scheme E

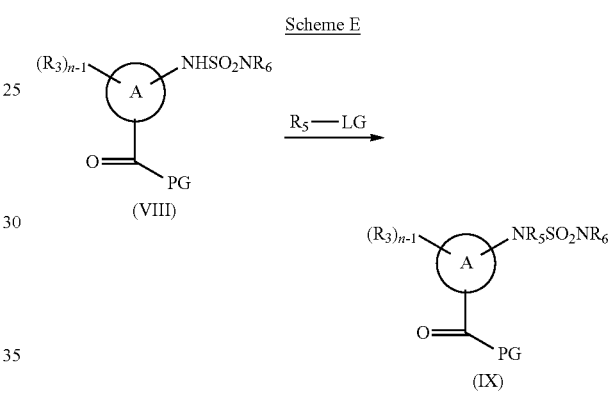

Typical reaction conditions comprise reacting a compound of formula (VIII) with a compound of formula $R_5LG$ in a suitable polar aprotic solvent, such as DMF, DMSO, acetonitrile, DCM or chloroform, in the presence an appropriate base, such as $K_2CO_3$, NaH, nBuLi, or DMAP, at an appropriate temperature such as, for example, 50 degrees.

Compounds of formula (VII) as above defined may be prepared according to Scheme F below reported by reaction of a compound of formula (X), wherein PG is a suitable carboxylic protecting group, under appropriate reduction conditions Scheme F

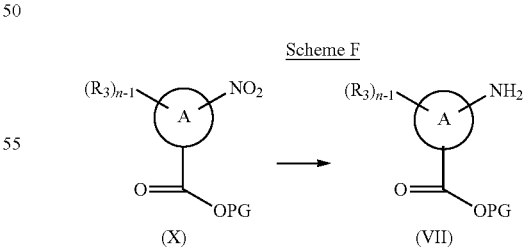

Typical reaction conditions comprise reacting a compound of formula (X) in a suitable polar aprotic solvent, such as THF, DMF, acetonitrile, DCM or chloroform, with a suitable reducing agent such as $SnCl_2 2H_2O$ (tin chloride dihydrate) or sodium dithionite at an appropriate temperature such as, for example, RT. Compound (X) can be reduced also in a suitable polar protic solvent such as MeOH or EtOH, with a suitable catalyst such Pd/C or Ni Raney under hydrogen atmosphere at an appropriate temperature such as, for example, RT.

Compounds of formula (X) as above defined may be prepared according to Scheme G below reported by reaction of a compound of formula (XI), where in A is a group (a) or (b), n is 1 or 2 and $R_3$ is as above defined, under appropriate oxidizing conditions, followed by protection of carboxyl group with protecting group PG under suitable conditions.

Scheme G

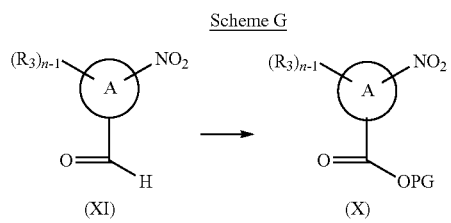

Typical reaction conditions comprise reacting a compound of formula (XI) in a suitable polar aprotic solvent, such as DMF, acetonitrile, DCM, dioxane or chloroform, in the presence of an appropriate oxidizing agent such as Oxone (mixture of 2 $KHSO_5.KHSO_4.K_2SO_4$) or PDC (pyridinium dichromate) or in a suitable mixture of a polar aprotic solvent and an aqueous solvent, such as dioxane and a solution of sodium chlorite in water, in the presence of an appropriate oxidizing agent, such as sulfamic acid, at an appropriate temperature, such as, for example, RT. Alternatively, the oxidation may be carried out in a suitable polar protic solvent, such as acetone, dioxane or t-BuOH and an appropriate oxidizing agent such as potassium permanganate or Jones reagent.

Compounds of formula (XI) as above defined may be prepared according to Scheme H below reported by reaction of a compound of formula (XII), where in A is a group (a) or (b), n is 1 or 2 and $R_3$ is as above defined, under appropriate nitrating conditions.

Scheme H

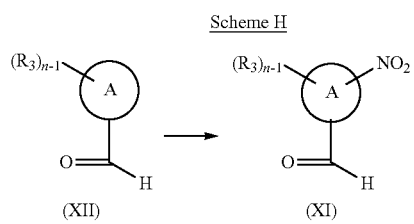

Typical reaction conditions comprise reacting a compound of formula (XII) dissolved in acetic anhydride, trifluoroacetic anhydride, aqueous conc. sulfuric acid or triflic anhydride adding an appropriate nitro source such as nitric acid in glacial acetic acid, nitric acid in sulfuric acid, nitric acid in acetic anhydride, aqueous nitric acid, ammonium nitrate or potassium nitrate in aqueous nitric acid at an appropriate temperature, such as, for example, 0 degrees.

Compounds of formula (IIIc), i.e. compounds of formula (III) wherein A is a group (c) or (d) wherein nitrogen is substituted by $R_3$ being ($C_1$-$C_6$)alkyl, n is 2, $R_3$ is at the other occurrence a group —$NR_5SO_2R_6$, may be prepared according to Scheme J below reported by reaction of a compound of formula (XIII), wherein A is a group (c) or (d) wherein nitrogen is substituted by $R_3$ being ($C_1$-$C_6$)alkyl and n is 2, with an appropriate sulfonylating agent of formula $R_6SO_2X$, wherein X is a leaving group such as chlorine.

Scheme J

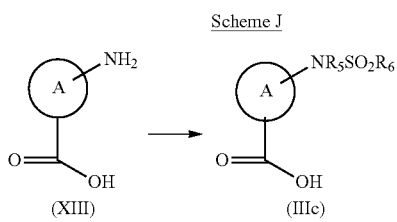

Typical reaction conditions comprise reacting a compound of formula (XIII) with a compound of formula $R_6SO_2X$ in a suitable polar aprotic solvent, such as DMF, DMSO, acetonitrile, DCM or chloroform, in the presence an appropriate base, such as DMAP, TEA or DIPEA at an appropriate temperature such as, for example, RT, or in a neat base such as pyridine at an appropriate temperature as, for example, 0 degrees.

Compounds of formula (XIII) as above defined may be prepared according to Scheme K below reported by reaction of a compound of formula (XIV), wherein A is a group (c) or (d) wherein nitrogen is substituted by $R_3$ being ($C_1$-$C_6$) alkyl, under appropriate reduction conditions Scheme K

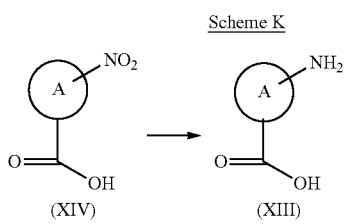

Typical reaction conditions comprise reacting a compound of formula (XIV) in a suitable polar aprotic solvent, such as THF, acetonitrile, DCM or chloroform, in the presence of an appropriate reducing agent such as $SnCl_2 2H_2O$ (tin chloride dihydrate) or sodium dithionite, or in a suitable mixture of polar aprotic solvent and aqueous solvent, such as EtOH and water, in the presence of an appropriate reducing agent such as iron powder and ammonium chloride, at an appropriate temperature such as, for example, RT. Compound (X) can be reduced also in a suitable aqueous solvent such as sodium carbonate 1M or polar protic solvent such as MeOH or EtOH, with a suitable catalyst such Pd/C or Ni Raney under hydrogen atmosphere at an appropriate temperature such as, for example, RT.

Compounds of formula (XIV) as above defined may be prepared according to Scheme L below reported by reaction of a compound of formula (XV), wherein A is a group (c) or (d) wherein nitrogen is substituted by $R_3$ being ($C_1$-$C_6$)alkyl, under appropriate nitrating conditions.

Scheme L

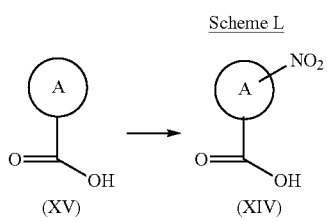

Typical reaction conditions comprise reacting a compound of formula (XV) dissolved in acetic anhydride, trifluoroacetic anhydride or triflic anhydride adding an appropriate nitro source such as nitric acid in glacial acetic acid, nitric acid in sulfuric acid, nitric acid in acetic anhydride, ammonium nitrate or copper nitrate at an appropriate temperature such as, for example, 0 degrees.

Compounds of formula (IIId), i.e. compounds of formula (III) wherein A is a group (c) or (d), n is 1 or 2 and $R_3$ is at one occurrence a group —$SO_2R_{11}$ which is linked to nitrogen atom of ring A, may be prepared according to Scheme M below reported by reaction of a compound of formula (XVI), wherein PG is a suitable carboxylic protecting group, with an appropriate compound of formula $R_{11}SO_2Cl$, followed by deprotection of carboxyl group under suitable conditions.

Scheme M

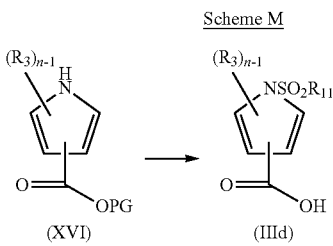

Typical reaction conditions comprise reacting a compound of formula (XVI) with a compound of formula $R_{11}SO_2Cl$ in a suitable polar aprotic solvent, such as DMF, acetonitrile, DCM or chloroform, in the presence an appropriate base, such as DMAP, TEA, $NaOH_{aq}$ or DIPEA at an appropriate temperature such as, for example, RT, in the presence of an appropriate transfer phase catalyst, if needed, such as tetrabutylammonium hydrogen sulphate, or in a neat base such as pyridine at an appropriate temperature as, for example, 0 degrees.

The present invention also provides pharmaceutical compositions of compounds of the invention in admixture with one or more pharmaceutically acceptable carriers, for example those described in Remington's Pharmaceutical Sciences Handbook, XVII Ed., Mack Pub., N.Y., U.S.A., which is incorporated herein by reference in its entirety.

Administration of the compounds of the present invention may be accomplished according to patient needs, for example, orally, nasally, parenterally (subcutaneously, intravenously, intramuscularly, intrasternally and by infusion), by inhalation, rectally, vaginally, topically, locally, transdermally, and by ocular administration. Various solid oral dosage forms may be used for administering compounds of the invention including such solid forms as tablets, gelcaps, capsules, caplets, granules, lozenges and bulk powders. The compounds of the present invention may be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms may also be used for administering compounds of the present invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention may be prepared by mixing the compound with a suitable excipient such as cocoa butter, salicylates and polyethylene glycols.

Formulations for vaginal administration may be in the form of cream, gel, paste, foam, or spray formula containing, in addition to the active ingredient, such suitable carriers as are known in the art.

For topical administration the pharmaceutical composition may be in the form of creams, ointments, liniments, lotions, emulsions, suspensions, gels, solutions, pastes, powders, sprays, and drops suitable for administration to the skin, eye, ear, or nose. Topical administration may also involve transdermal administration via means such as transdermal patches.

For the treatment of the diseases of the respiratory tract, the compounds according to the invention are preferably administered by inhalation.

Inhalable preparations include inhalable powders, propellant-containing metered aerosols or propellant-free inhalable formulations all of which may be delivered by a suitable device known in the art.

For administration as a dry powder, single- or multi-dose inhalers known from the prior art may be utilized. In that case the powder may be filled in gelatine, plastic or other capsules, cartridges or blister packs or in a reservoir.

A diluent or carrier, generally non-toxic and chemically inert to the compounds of the invention, e.g. lactose or any other additive suitable for improving the respirable fraction may be added to the powdered compounds of the invention.

Inhalation aerosols containing propellant gas such as hydrofluoroalkanes may contain the compounds of the invention either in solution or in dispersed form. The propellant-driven formulations may also contain other ingredients such as co-solvents, stabilizers and optionally other excipients.

The propellant-free inhalable formulations comprising the compounds of the invention may be in the form of solutions or suspensions in an aqueous, alcoholic or hydroalcoholic medium and they may be delivered by jet or ultrasonic nebulizers known from the prior art or by soft-mist nebulizers such as Respimat®.

The compounds of the present invention may be administered as the sole active agent or in combination with other pharmaceutical active ingredients including those currently used in the treatment of respiratory disorders, e.g. beta$_2$-agonists, corticosteroids and anticholinergic or antimuscarinic agents.

The dosages of the compounds of the present invention depend upon a variety of factors including the particular disease to be treated, the severity of the symptoms, the route of administration, the frequency of the dosage interval, the particular compound utilized, the efficacy, toxicology profile, and the pharmacokinetic profile of the compound.

Advantageously, the compounds of the invention may be administered for example, at a dosage of 0.001 to 1000 mg/day, preferably 0.1 to 500 mg/day.

When they are administered by inhalation route, the dosage of the compounds of the invention is advantageously 0.01 to 20 mg/day, preferably 0.1 to 10 mg/day.

Preferably, the compounds of the present invention alone or combined with other active ingredients may be administered for the prevention and/or treatment of any obstructive respiratory disease such as asthma, chronic bronchitis and chronic obstructive pulmonary disease (COPD).

However the compounds of the present invention may be administered for the prevention and/or treatment of any disease wherein PDE4 inhibition is required. Said disease include: allergic disease states such as atopic dermatitis, urticaria, allergic rhinitis, allergic conjunctivitis, vernal conjunctivitis, eosinophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, cystic fibrosis, arterial restenosis, artherosclerosis, keratosis, rheumatoid spondylitis, osteoarthritis, pyresis, diabetes mellitus, pneumoconiosis, toxic and allergic contact eczema, atopic eczema, seborrheic eczema, lichen simplex, sunburn, pruritus in the anogenital area, alopecia greata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

They also include neurological and psychiatric disorders such as Alzheimer's disease, multiple sclerosis, amylolateroscloerosis (ALS), multiple systems atrophy (MSA), schizophrenia, Parkinson's disease, Huntington's disease, Pick's disease, depression, stroke, and spinal cord injury.

The present invention will now be further described by way of the following non-limiting examples.

Other features of the invention will become apparent in the course of the following descriptions of exemplary embodiments which are given for illustration of the invention and are not intended to be limiting thereof.

EXAMPLES

Chemical Names of the compounds were generated with Structure To Name Enterprise 10.0 Cambridge Software.
Abbreviations:
EDC=1-ethyl-3-(3-dimethylaminopropyl) carbodiimide) hydrochloride;
DMAP=4-dimethylaminopyridine;
DMF=dimethylformamide;
EtOAc or AcOEt=Ethyl acetate;
RT or Rt=room temperature;
THF=tetrahydrofuran;
DCM=dichloromethane;
Et$_2$O=diethyl ether;
MeOH=methyl alcohol;
EtOH=ethylic alcohol;
(Ipr)$_2$O=diisopropylether;
TEA=Triethylamine;
TFA=trifluoroacetic acid;
CH$_3$CN=acetonitrile;
(Boc)$_2$O=ditertbutyl dicarbonate;
DIPEA=di-isopropyl ethyl amine;
DMSO=dimethylsulfoxide.
NMR characterization:

NMR spectra were recorder either with:

$^1$H-NMR spectra were recorded on a 400 MHz Varian AS400 spectrometer. Chemical shift are reported as δ values in ppm relative to trimethyl silane (TMS) as an internal standard. Coupling constants (J values) are given in hertz (Hz) and multiplicities are reported using the following abbreviation (s=singlet, d=doublet, t=triplet, q=quartet, m=multiplet, br=broad, nd=not determined).

or $^1$H-NMR spectra were recorded on a Bruker ARX300 Spectrometer at 300.13 MHz (1H) using deuterated solvents, such as deuterated dimethylsulfoxide (DMSO-d6) or deuterated chloroform (CDCl3). The instrument was equipped with a multinuclear inverse probe and temperature controller. Chemical shifts are expressed in parts per million (ppm) downfield of tetramethylsilane (δ units). Multiplicity is indicated as follow: (s) singlet, (d) doublet, (dd) double doublet, (ddd) triple doublet, (t) triplet, (dt) double triplet, (q) quartet, (m) multiplet, (br s) broad signal. Coupling constants J are expressed in units of hertz (Hz).

Preparative HPLC-Method 1:
Column: Waters Symmetry Prep C18 17 um 19×300
Flow: 20 ml/min
Mobile phase: 90% H$_2$O, 10% acetonitrile, 0.05% TFA (A), 10% H$_2$O, 90% acetonitrile,
0.05% TFA (B)
Gradient:

| Time (min) | % A | % B |
|---|---|---|
| 0.00 | 95 | 5 |
| 5 | 95 | 5 |
| 28 | 0 | 100 |
| 30 | 0 | 100 |

The same gradient without TFA in mobile phase was used for preparative HPLC under neutral conditions.

Preparative HPLC-Method 2:

Waters Micromass ZQ; Sample manager 2767; Photodiode array detector 2996;
Column XTerra Prep MS C18 Column (5 µm, 19×150 mm, Waters); flow rate of 20 ml/min with MS detection or UV set at 254 nm.
Gradient:

| Time (min) | % A | % B |
|---|---|---|
| 0.00 | 100.0 | 0.00 |
| 1.00 | 100 | 0.00 |
| 10.00 | 0.00 | 100.0 |
| 11.00 | 0.00 | 100.0 |
| 12.00 | 100.0 | 0.00 |

Eluent
Solvent A (water:MeCN:HCOOH 95:5:0.05)
Solvent B (water:MeCN:HCOOH 5:95:0.05)

Preparative HPLC-Method 3:
Waters Micromass ZQ/sample manager 2767
Photodiode array detector: 2996
Column: XTERRA Prep MS C18 10 um 19×300
Flow: 20 ml/min
Mobile phases: $H_2O$, 0.1% TFA (A); acetonitrile, 0.1% TFA (B)
Gradient:

| Time (min) | % A | % B |
|---|---|---|
| 0.00 | 90 | 10 |
| 2 | 90 | 10 |
| 23 | 0 | 100 |
| 30 | 0 | 100 |

Conditioning:

| Time (min) | % A | % B |
|---|---|---|
| 30.5 | 90 | 10 |
| 32 | 90 | 10 |

Optical Rotation (Activity) determination:
Specific rotations of compounds were measured with a Polarimeter Perkin Elmer model 241 or 341.
Temperature (° C.) 25
Path Length (dm) 1
Wavelength Sodium D-line (589 nm)
Automated Microwave Synthesis System:
Microwave-assisted reactions were performed using a CEM Discover reactor.
Microwave power output from 0 to 300 watts
Temperature range from 0 to 300 degrees
Pressure range from 0 to 300 psi
Volume of vessels from 5 ml to 125 ml (for reactions performed under atmospheric conditions)
10 ml septa vessels (for elevated temperatures and pressures)
The MS/ESI+ values reported in the text below may be obtained or by MS instrument Waters ZQ (or equivalent) or by UPLC Waters instrument:
MS instrument: Waters ZQ (or equivalent)
Polarity ES
Capillary (kV) 3.00
Cone (V) 20.00
Extractor (V) 3.00
RF Lens (V) 1.0
Polarity ES
Capillary (kV) 3.00
Cone (V) 20.00
Extractor (V) 3.00
RF Lens (V) 1.0
Source Temperature (° C.) 110
Desolvation Temperature (° C.) 210
Cone Gas Flow (L/Hr) 150
Desolvation Gas Flow (L/Hr) 650
Mass range: 100 to 950
Scan time (sec): 0.32
Inter-Scan delay (sec): 0.03
LC instrument: Acquity Waters UPLC
Instrument: UPLC Waters coupled with ZQ micromass and interfaced with 2996 PDA detector
Column: Acquity UPLC BEH C18 1.7 um 50×2.1 mm
Method: TFA long Conditions: ESI+, 3.2 KV, 25V, 350° C.
Wavelength: PBI

| Time (sec) | % B | Flow (mL/min) | A | B |
|---|---|---|---|---|
| 0.00 | 5.0 | 0.6 | 95:5 H2O:ACN | 5:95 H2O:ACN |
| 0.50 | 5.0 | 0.6 | (0.1% TFA) | (0.1% TFA) |
| 6.00 | 100.0 | 0.6 | | |
| 7.00 | 100.0 | 0.6 | | |
| 7.10 | 5.0 | 0.6 | | |
| 8.50 | 5.0 | 0.6 | | |

Detailed synthetic pathways and procedures for specific compounds are outlined in Examples 1-16. The synthesis of (S)-3,5-dichloro-4-(2-(3-(cyclopropylmethoxy)-4-(difluoromethoxy)phenyl)-2-hydroxyethyl)pyridine 1-oxide may be performed as described in WO 2010/089107, which is incorporated herein by reference in its entirety, (compound 7).

In the procedures that follow, after each starting material, reference to a compound number is sometimes provided. This is provided merely for assistance to the skilled chemist. The starting material may not necessarily have been prepared from the batch referred to.

When reference is made to the use of a "similar" or "analogous" procedure, as will be appreciated by those skilled in the art, such a procedure may involve minor variations, for example reaction temperature, reagent/solvent amount, reaction time, work-up conditions or chromatographic purification conditions.

Example 1

Synthesis of (S)-3,5-dichloro-4-(2-(3-(cyclopropylmethoxy)-4-(difluoromethoxy)phenyl)-2-(1-(phenylsulfonyl)-1H-pyrrole-2-carbonyloxy)ethyl)-pyridine 1-oxide (Compound 3)

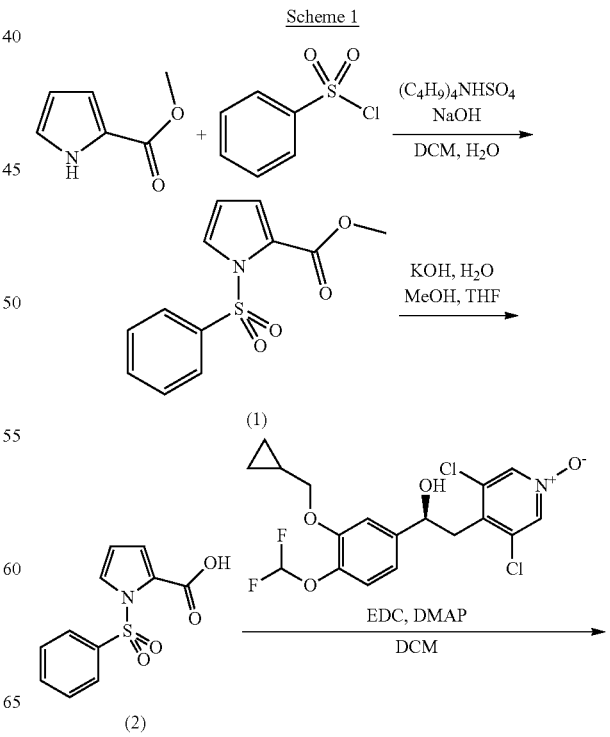

Scheme 1

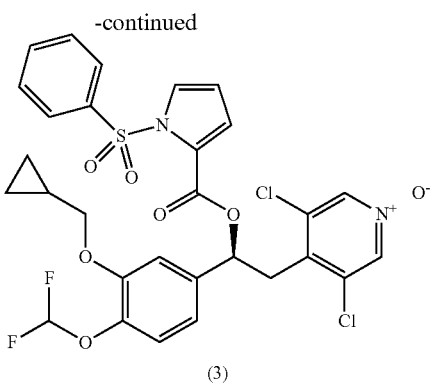

(3)

Step 1. Preparation of methyl 1-(phenylsulfonyl)-1H-pyrrole-2-carboxylate (Intermediate 1)

To a mixture of methyl 1H-pyrrole-2-carboxylate (1 g, 7.99 mmol), tetrabutylammonium hydrogen sulfate (0.271 g, 0.799 mmol) and NaOH (2.88 g, 71.9 mmol) in water (5 ml) and DCM (40 ml) under vigorous stirring, a solution of benzenesulfonyl chloride (1.794 ml, 13.99 mmol) in DCM (5 ml) was added drop-wise over 10 minutes at RT. The reaction was stirred at the same temperature for 3 hours. The mixture was diluted with water (50 ml) and DCM (100 ml), the organics were separated, washed with brine (50 ml) and dried over sodium sulfate. The solvent was evaporated and the residue was purified by flash chromatography on silica gel column (petroleum ether/acetone 8/2) to afford methyl 1-(phenylsulfonyl)-1H-pyrrole-2-carboxylate (Intermediate 1) (1.448 g, 5.46 mmol, MS/ESI$^+$287.9 [MNa]$^+$).

Step 2. Preparation of 1-(phenylsulfonyl)-1H-pyrrole-2-carboxylic acid (Intermediate 2)

To a solution of methyl 1-(phenylsulfonyl)-1H-pyrrole-2-carboxylate (Intermediate 1) (500 mg, 1.885 mmol) in MeOH (7 ml) and THF (7 ml) cooled to 0° C., aqueous 1N KOH (2.827 ml, 2.83 mmol) was added drop-wise and the resulting mixture was stirred at RT for 24 hours. UPLC-MS analysis showed the presence of desired compound in admixture with methyl 1H-pyrrole-2-carboxylate as the main product. The mixture was poured into ice-water and washed with DCM. The aqueous phase was acidified with 37% HCl (pH=2) and extracted with DCM. The organic layer was dried over sodium sulfate, filtered and evaporated to afford a mixture of 1-(phenylsulfonyl)-1H-pyrrole-2-carboxylic acid (Intermediate 2) (MS/ESI$^+$252.0 [MH]$^+$) and methyl 1H-pyrrole-2-carboxylate (MS/ESI$^+$126.0 [MH]$^+$) (234 mg, ratio about 3/7). This mixture was used as such in the next step.

Step 3. Preparation of (S)-3,5-dichloro-4-(2-(3-(cyclopropylmethoxy)-4-(difluoromethoxy)phenyl)-2-(1-(phenylsulfonyl)-1H-pyrrole-2-carbonyloxy)ethyl)-pyridine 1-oxide (Compound 3)

A mixture of crude 1-(phenylsulfonyl)-1H-pyrrole-2-carboxylic acid (234 mg, compound obtained as above indicated in step 2), (S)-3,5-dichloro-4-(2-(3-(cyclopropylmethoxy)-4-(difluoromethoxy)phenyl)-2-hydroxyethyl) pyridine1-oxide (117 mg, 0.279 mmol), EDC (161 mg, 0.838 mmol), and DMAP (34.1 mg, 0.279 mmol) in DCM (15 ml) was stirred at RT for 5 hours. The mixture was diluted with DCM and washed with 0.5N HCl, sat. $Na_2CO_3$ and finally with brine; the organic phase was dried over sodium sulfate and the solvent removed under vacuum. The crude was purified by preparative HPLC-Method 1 to afford (S)-3,5-dichloro-4-(2-(3-(cyclopropylmethoxy)-4-(difluoromethoxy)phenyl)-2-(1-(phenylsulfonyl)-1H-pyrrole-2-carbonyloxy)ethyl)-pyridine 1-oxide (Compound 3) (45 mg, 0.069 mmol, MS/ESI$^+$653.07 [MH]$^+$, [$\alpha_D$]=−25.83, c=0.6, DCM).

$^1$H NMR (300 MHz, DMSO-$d_6$) δ ppm 8.47 (s, 2H), 7.87 (dd, 1H), 7.78-7.85 (m, 2H), 7.68-7.78 (m, 1H), 7.51-7.64 (m, 2H), 7.28 (dd, 1H), 7.16 (d, 1H), 7.11 (d, 1H), 6.98 (dd, 1H), 7.06 (t, 1H), 6.52 (t, 1H), 6.01 (dd, 1H), 3.89 (d, 2H), 3.44 (dd, 1H), 3.22 (dd, 1H), 1.09-1.30 (m, 1H), 0.47-0.63 (m, 2H), 0.26-0.41 (m, 2H).

Example 2

Synthesis of (S)-4-(2-(1-(4-aminophenylsulfonyl)-1H-pyrrole-2-carbonyloxy)-2-(3-(cyclopropylmethoxy)-4-(difluoromethoxy)phenyl)ethyl)-3,5-dichloropyridine 1-oxide (Compound 7)

Scheme 2

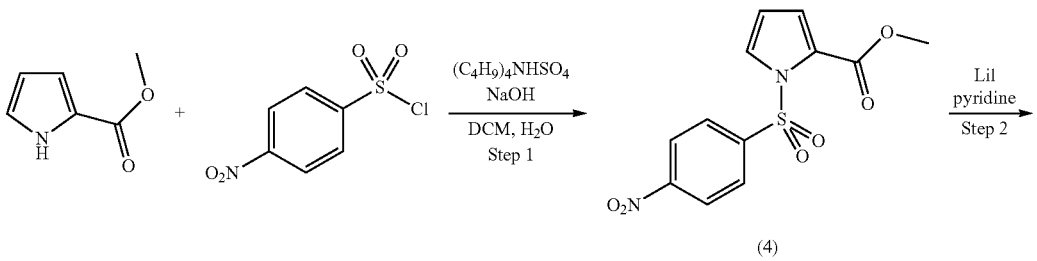

(4)

-continued

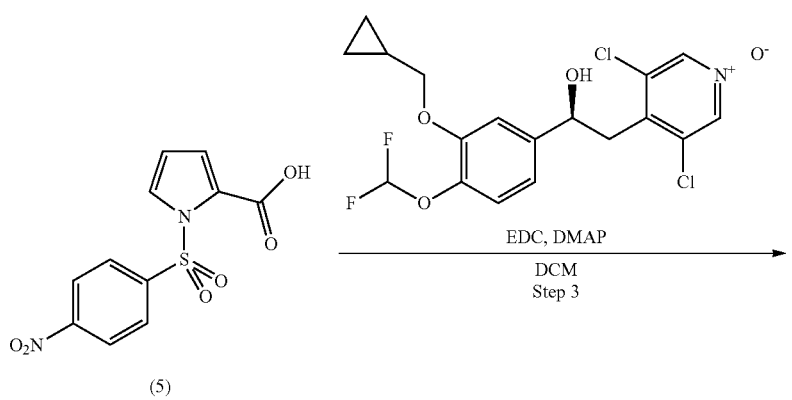

(5)

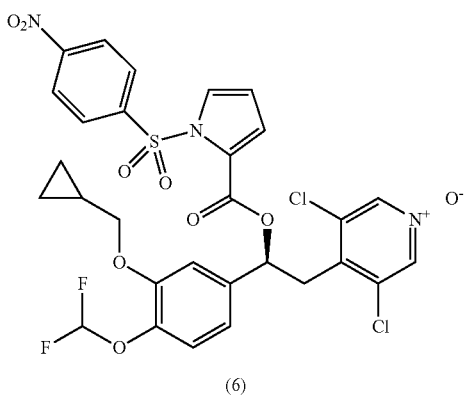

(6)

Step 4 | SnCl$_2$*2H$_2$O
         THF

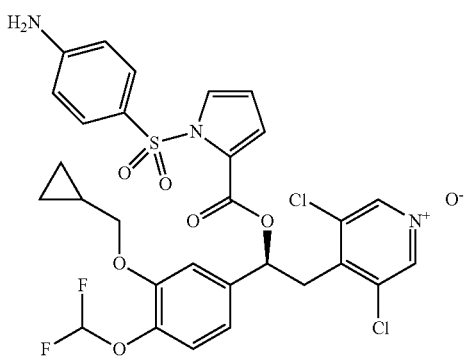

Step 1. Preparation of methyl 1-(4-nitrophenylsulfonyl)-1H-pyrrole-2-carboxylate (Intermediate 4)

To a mixture of methyl 1H-pyrrole-2-carboxylate (500 mg, 4.00 mmol), tetrabutylammonium hydrogensulfate (136 mg, 0.400 mmol) and sodium hydroxide (1.438 g, 36.0 mmol) in water (2.5 ml) and DCM (40 ml) under vigorous stirring, 4-nitrobenzene-1-sulfonyl chloride (1.550 g, 6.99 mmol) was added portion-wise over 10 minutes at RT. After 20 hours, the mixture was diluted with water (50 ml) and DCM (100 ml); the organics were separated, washed with brine (80 ml×2) and dried over sodium sulfate. The solvent was evaporated and the crude was triturated with MeOH (50 ml) overnight affording, after filtration, methyl 1-(4-nitrophenylsulfonyl)-1H-pyrrole-2-carboxylate (Int. 4) (555 mg, 1.789 mmol, MS/ESI⁺311.0 [MH]⁺).

Step 2. Preparation of
1-(4-nitrophenylsulfonyl)-1H-pyrrole-2-carboxylic
acid (Intermediate 5)

To a solution of methyl 1-(4-nitrophenylsulfonyl)-1H-pyrrole-2-carboxylate (Int. 4) (550 mg, 1.773 mmol) in pyridine (25 ml), lithium iodide (1661 mg, 12.41 mmol) was added and the resulting mixture was refluxed for 8 hours. The solution was concentrated under vacuum and the crude was dissolved in DCM (150 ml) and washed with 1N HCl (50 ml×2) and then with brine (50 ml); the organic layer was dried over sodium sulfate and the solvent was removed affording 1-(4-nitrophenylsulfonyl)-1H-pyrrole-2-carboxylic acid (Int. 5) (433 mg, 1.462 mmol).

Step 3. Preparation of (S)-3,5-dichloro-4-(2-(3-(cyclopropylmethoxy)-4-(difluoromethoxy)phenyl)-2-(1-(4-nitrophenylsulfonyl)-1H-pyrrole-2-carbonyloxy)-ethyl)pyridine 1-oxide (Intermediate 6)

A mixture of (S)-3,5-dichloro-4-(2-(3-(cyclopropylmethoxy)-4-(difluoromethoxy)phenyl)-2-hydroxyethyl)pyridine 1-oxide (206 mg, 0.490 mmol), 1-(4-nitrophenylsulfonyl)-1H-pyrrole-2-carboxylic acid (Int. 5) (160 mg, 0.539 mmol), EDC (282 mg, 1.471 mmol) and DMAP (59.9 mg, 0.490 mmol) in DCM (10 ml) was stirred at RT for 24 hours. The reaction was diluted with DCM and washed with 1N HCl, sat. NaHCO₃ (40 ml), and finally with brine. The organic phase was dried over sodium sulfate and the solvent was removed under vacuum; the crude was purified by preparative HPLC-Method 1 to yield (S)-3,5-dichloro-4-(2-(3-(cyclopropylmethoxy)-4-(difluoromethoxy)phenyl)-2-(1-(4-nitrophenylsulfonyl)-1H-pyrrole-2-carbonyloxy)ethyl)pyridine 1-oxide (Int. 6) (95 mg, 0.136 mmol, MS/ESI⁺698.05 [MH]⁺, [α$_D$]=−40.97, c=0.6, DCM).

¹H NMR (300 MHz, DMSO-d₆) δ ppm 8.40 (s, 2H), 8.36-8.40 (m, 2H), 8.04-8.18 (m, 2H), 7.94 (dd, 1H), 7.36 (dd, 1H), 7.17 (d, 1H), 7.13 (d, 1H), 7.01 (dd, 1H), 7.05 (t, 1H), 6.59 (dd, 1H), 6.03 (dd, 1H), 3.90 (d, 2H), 3.45 (dd, 1H), 3.23 (dd, 1H), 1.07-1.32 (m, 1H), 0.46-0.64 (m, 2H), 0.23-0.43 (m, 2H).

Step 4. Preparation of (S)-4-(2-(1-(4-aminophenylsulfonyl)-1H-pyrrole-2-carbonyloxy)-2-(3-(cyclopropylmethoxy)-4-(difluoromethoxy)-phenyl)ethyl)-3,5-dichloropyridine 1-oxide (Compound 7)

A mixture of (S)-3,5-dichloro-4-(2-(3-(cyclopropylmethoxy)-4-(difluoromethoxy)phenyl)-2-(1-(4-nitrophenylsulfonyl)-1H-pyrrole-2-carbonyloxy)-ethyl)pyridine 1-oxide (Int. 6) (424 mg, 0.607 mmol) and tin(II) chloride dihydrate (548 mg, 2.428 mmol) in THF (40 ml) was heated at 45° C. for 2 hours. Additional tin(II) chloride dihydrate (1.644 g, 7.284 mmol) was added in 3 portion over 3 hours at 60° C., and the resulting mixture was heated to reflux overnight. The solvent was removed and the mixture was diluted with ethyl acetate; aqueous sat. NaHCO₃ was added and the mixture was filtered through a celite pad. The filtered phases were separated and the organic layer was washed with brine and dried over sodium sulfate; the solvent was removed and the crude was purified by flash chromatography on silica gel column (DCM/MeOH=98/2) affording (S)-4-(2-(1-(4-aminophenylsulfonyl)-1H-pyrrole-2-carbonyloxy)-2-(3-(cyclopropylmethoxy)-4-(difluoromethoxy)-phenyl)ethyl)-3,5-dichloropyridine 1-oxide (Int. 7) (207 mg, 0.310 mmol, MS/ESI⁺667.96 [MH]⁺, [α$_D$]=−61.24, c=1, DCM).

¹H NMR (300 MHz, DMSO-d₆) δ ppm 8.50 (s, 2H), 7.68 (dd, 1H), 7.48-7.58 (m, 2H), 7.11-7.20 (m, 3H), 6.99 (dd, 1H), 7.05 (t, 1H), 6.51-6.63 (m, 2H), 6.38 (dd, 1H), 6.32 (s, 2H), 6.05 (dd, 1H), 3.90 (m, 2H), 3.47 (dd, 1H), 3.29 (dd, 1H), 1.03-1.37 (m, 1H), 0.43-0.76 (m, 2H), 0.22-0.43 (m, 2H).

The compound listed in Table 1 was prepared with a procedure analogous to that described in Scheme 2, Step 1, 2, and 3, by using suitable reagents.

TABLE 1

| Structure | Compound | NMR characterization | MS/ESI⁺ [MH]⁺ | [α$_D$] | Purification |
|---|---|---|---|---|---|
| (structure) | 8 | ¹H NMR (300 MHz, DMSO-d₆) δ ppm 8.49 (s, 2 H), 7.91 (dd, 1 H), 7.83-7.89 (m, 2 H), 7.75 (dt, 1 H), 7.65 (dd, 1H), 7.31 (dd, 1 H), 7.16 (d, 1 H), 7.11 (d, 1 H), 6.96 (dd, 1H), 7.05 (t, 1 H), 6.54 (t, 1 H), 5.98 (dd, 1 H), 3.90 (d, 2 H), 3.45 (dd, 1 H), 3.24 (dd, 1 H), 2.99 (br. s., 3 H), 2.78 (br. s., 3 H), 1.07-1.32 (m, 1 H), 0.47-0.66 (m, 2 H), 0.20-0.45 (m, 2 H) | 724.08 | −23.78 c = 0.65 DCM | preparative HPLC-method 1 |

Example 3
Synthesis of (S)-3,5-dichloro-4-(2-(3-(cyclopropylmethoxy)-4-(difluoromethoxy)phenyl)-2-(1-(3-(dimethylcarbamoyl)-4-hydroxyphenylsulfonyl)-1H-pyrrole-2-carbonyloxy)ethyl)pyridine 1-oxide (Compound 13) and (S)-3,5-dichloro-4-(2-(3-(cyclopropylmethoxy)-4-(difluoromethoxy)phenyl)-2-(1-(3-(dimethylcarbamoyl)-4-methoxyphenylsulfonyl)-1H-pyrrole-2-carbonyloxy)ethyl)pyridine 1-oxide (Compound 14)
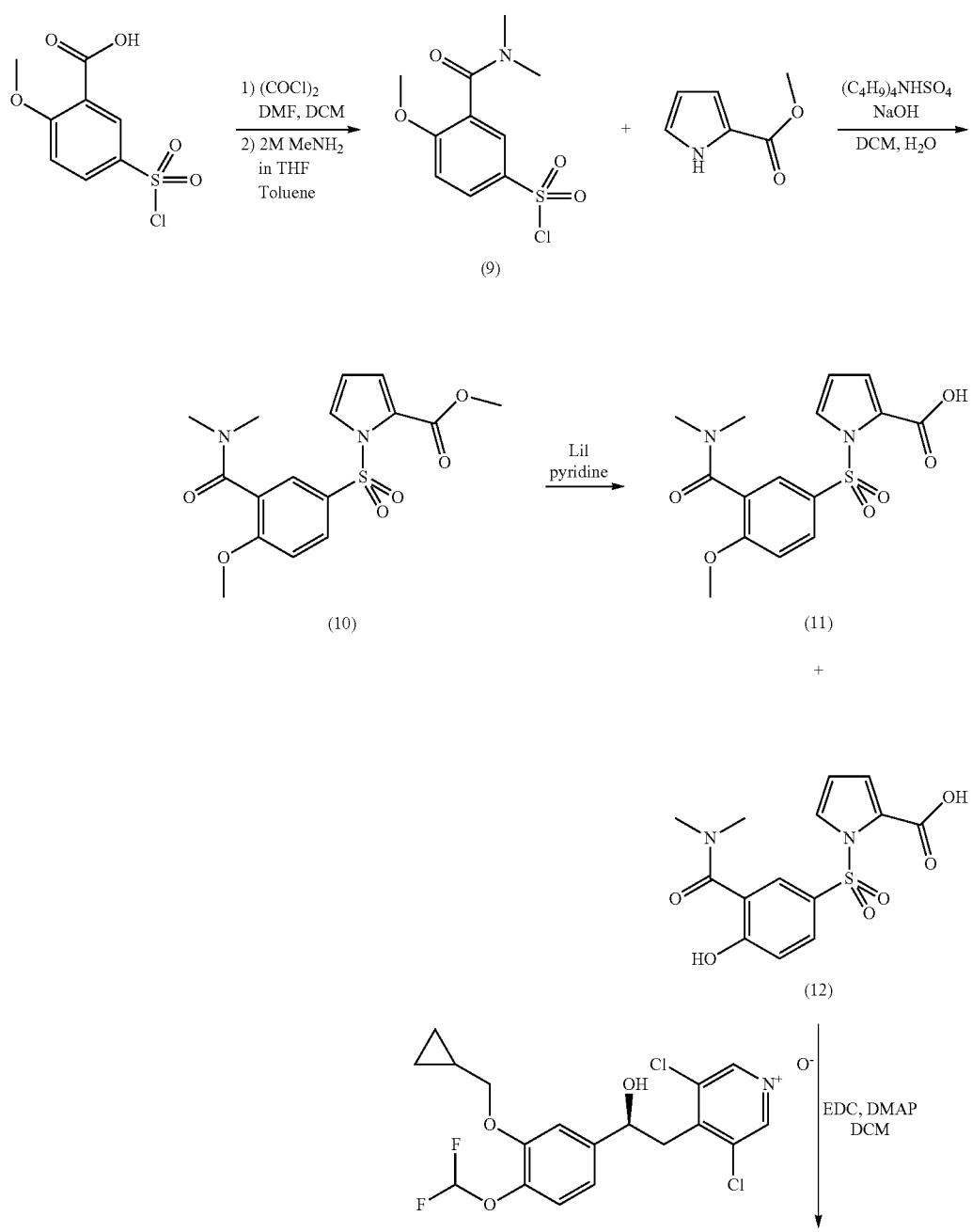

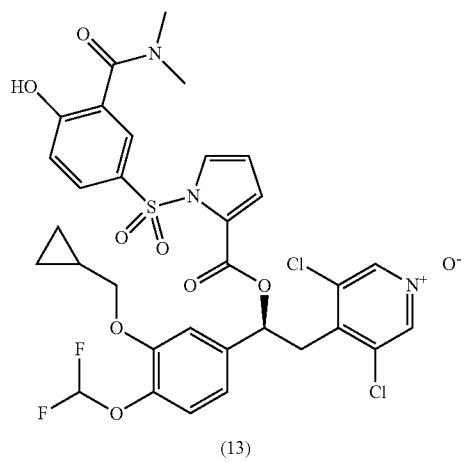

(13)

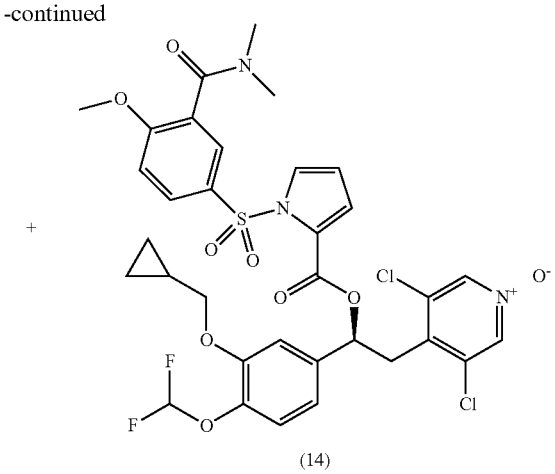

(14)

Step 1. Preparation of 3-(dimethylcarbamoyl)-4-methoxybenzene-1-sulfonyl chloride (Intermediate 9)

To a suspension of 5-(chlorosulfonyl)-2-methoxybenzoic acid (1.243 g, 4.96 mmol) in dry DCM (20 ml) cooled to 0° C., (COCl)$_2$ (1.302 ml, 14.88 mmol) was added drop-wise followed by few drops of dry DMF and the reaction was stirred at RT for 1 hour. The mixture was concentrated under reduced pressure, treated with dry toluene (30 ml×2) and evaporated to dryness. The residue was suspended in dry toluene (20 ml) and the resulting suspension was cooled to 0° C.; a solution of dimethylamine 2.0 M in THF (4.96 ml, 9.92 mmol) was added drop-wise and the reaction was stirred at RT overnight. The mixture was diluted with DCM and washed with brine; the organic phase was dried over sodium sulfate and the solvent was removed. The crude was purified by flash chromatography on silica gel (EtOAc/petroleum ether=60/40) to give 3-(dimethylcarbamoyl)-4-methoxybenzene-1-sulfonyl chloride (Int. 9) (400 mg, 1.440 mmol, MS/ESI$^+$278.0 [MH]$^+$).

Step 2. Preparation of methyl 1-(3-(dimethylcarbamoyl)-4-methoxyphenylsulfonyl)-1H-pyrrole-2-carboxylate (Intermediate 10)

To a mixture of methyl 1H-pyrrole-2-carboxylate (135 mg, 1.080 mmol), tetrabutylammonium hydrogensulfate (36.7 mg, 0.108 mmol) and sodium hydroxide (389 mg, 9.72 mmol) in water (2 ml) and DCM (4 ml) under vigorous stirring, a solution of 3-(dimethylcarbamoyl)-4-methoxybenzene-1-sulfonyl chloride (Int. 9) (300 mg, 1.080 mmol) in DCM (5 ml) was added drop-wise at RT over 10 minutes, and the reaction was stirred at the same temperature for 24 hours. The mixture was diluted with water and DCM, the organic phase was separated, washed with brine and dried over sodium sulfate. The solvent was evaporated under vacuum yielding methyl 1-(3-(dimethylcarbamoyl)-4-methoxyphenylsulfonyl)-1H-pyrrole-2-carboxylate (Int. 10) (260 mg, 0.710 mmol, MS/ESI$^+$367.0 [MH]$^+$) which was used as such in the next step.

Step 3. Preparation of 1-(3-(dimethylcarbamoyl)-4-hydroxyphenylsulfonyl)-1H-pyrrole-2-carboxylic (Intermediate 12) acid and 1-(3-(dimethylcarbamoyl)-4-methoxyphenylsulfonyl)-1H-pyrrole-2-carboxylic acid (Intermediate 11)

To a solution of methyl 1-(3-(dimethylcarbamoyl)-4-methoxyphenylsulfonyl)-1H-pyrrole-2-carboxylate (Int. 10) (260 mg, 0.710 mmol) in pyridine (7 ml), lithium iodide (665 mg, 4.97 mmol) was added, and the mixture was refluxed for 20 hours. The solvent was removed under vacuum and the crude was diluted with DCM; the resulting suspension washed with 1N HCl and then with brine. The organic phase was dried over sodium sulfate and the solvent was evaporated; the crude was purified by flash chromatography on silica gel (DCM/MeOH=9/1 to 1/1) to afford a mixture of 1-(3-(dimethylcarbamoyl)-4-hydroxyphenylsulfonyl)-1H-pyrrole-2-carboxylic acid (Int. 12) (MS/ESI$^+$ 339.0 [MH]$^+$) and 1-(3-(dimethylcarbamoyl)-4-methoxyphenylsulfonyl)-1H-pyrrole-2-carboxylic acid (Int. 11) (MS/ESI$^+$353.0 [MH]$^+$) (240 mg, approx 1/1 ratio) which was used as such in the next step.

Step 4. Preparation of (S)-3,5-dichloro-4-(2-(3-(cyclopropylmethoxy)-4-(difluoromethoxy)phenyl)-2-(1-(3-(dimethylcarbamoyl)-4-hydroxyphenylsulfonyl)-1H-pyrrole-2-carbonyloxy)ethyl)pyridine 1-oxide (Compound 13) and (S)-3,5-dichloro-4-(2-(3-(cyclopropylmethoxy)-4-(difluoromethoxy)phenyl)-2-(1-(3-(dimethylcarbamoyl)-4-methoxyphenylsulfonyl)-1H-pyrrole-2-carbonyloxy)ethyl)pyridine 1-oxide (Compound 14)

(S)-3,5-dichloro-4-(2-(3-(cyclopropylmethoxy)-4-(difluoromethoxy)-phenyl)-2-hydroxyethyl) pyridine 1-oxide (298 mg, 0.709 mmol), EDC (408 mg, 2.128 mmol), DMAP (95 mg, 0.780 mmol) and a mixture of 1-(3-(dimethylcarbamoyl)-4-hydroxyphenylsulfonyl)-1H-pyrrole-2-carboxylic acid (Int. 12) and 1-(3-(dimethylcarbamoyl)-4-methoxyphenylsulfonyl)-1H-pyrrole-2-carboxylic acid (Int. 11) (245 mg, prepared with the procedure described in Step 3 above) were dissolved in DCM (100 ml) and the reaction was stirred at RT for 2 days. The mixture was diluted with water (80 ml) and the precipitate was collected by filtration and purified by preparative HPLC-Method 1 affording:

First eluted compound: (S)-3,5-dichloro-4-(2-(3-(cyclopropylmethoxy)-4-(difluoromethoxy)phenyl)-2-(1-(3-(dimethylcarbamoyl)-4-hydroxyphenylsulfonyl)-1H-pyrrole-2-carbonyloxy)ethyl)pyridine 1-oxide (Compound 13) (55 mg, 0.074 mmol, MS/ESI⁺740.13 [MH]⁺, [α$_D$]=−15.20, c=0.8, DCM).

¹H NMR (300 MHz, DMSO-d$_6$) δ ppm 11.23 (s, 1H), 8.51 (s, 2H), 7.81 (dd, 1H), 7.76 (dd, 1H), 7.67 (d, 1H), 7.24 (dd, 1H), 7.15 (d, 1H), 7.11 (d, 1H), 7.01 (d, 1H), 6.97 (dd, 1H), 7.05 (t, 1H), 6.47 (t, 1H), 6.01 (dd, 1H), 3.90 (d, 2H), 3.47 (dd, 1H), 3.29 (dd, 1H), 2.95 (br. s., 3H), 2.68 (br. s., 3H), 1.07-1.33 (m, 1H), 0.45-0.66 (m, 2H), 0.21-0.44 (m, 2H).

Second Eluted Compound:

(S)-3,5-dichloro-4-(2-(3-(cyclopropylmethoxy)-4-(difluoromethoxy)-phenyl)-2-(1-(3-(dimethylcarbamoyl)-4-methoxyphenylsulfonyl)-1H-pyrrole-2-carbonyloxy)ethyl)pyridine 1-oxide (Compound 14) (25 mg, 0.033 mmol, MS/ESI⁺ 754.15 [MH]⁺, [α$_D$]=−28.00, c=0.1, DCM).

¹H NMR (300 MHz, DMSO-d$_6$) δ ppm 8.50 (s, 2H), 7.91 (dd, 1H), 7.86 (dd, 1H), 7.71 (d, 1H), 7.23-7.29 (m, 2H), 7.16 (d, 1H), 7.12 (d, 1H), 6.98 (dd, 1H), 7.05 (t, 1H), 6.48 (t, 1H), 6.02 (dd, 1H), 3.89 (s, 3H), 3.90 (d, 2H), 3.48 (dd, 1H), 3.27 (dd, 1H), 2.96 (s, 3H), 2.63 (br. s., 3H), 1.05-1.35 (m, 1H), 0.46-0.65 (m, 2H), 0.21-0.46 (m, 2H).

Example 4

Synthesis of (S)-3,5-dichloro-4-(2-(3-(cyclopropylmethoxy)-4-(difluoromethoxy)phenyl)-2-(1-methyl-4-(phenyl sulfonamido)-1H-pyrrole-2-carbonyloxy)ethyl)pyridine 1-oxide (Compound 17)

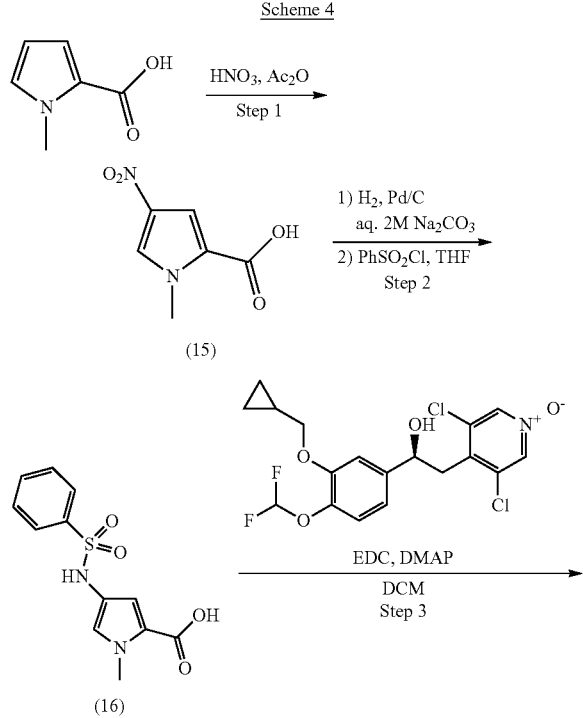

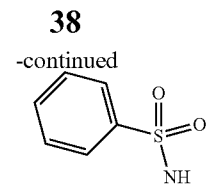

(17)

Step 1. Preparation of 1-methyl-4-nitro-1H-pyrrole-2-carboxylic acid (Intermediate 15)

Acetic anhydride (8 ml, 85 mmol) was treated with nitric acid (1.020 ml, 15.98 mmol) (heating occurred upon addition); the mixture was cooled to RT and slowly added to a suspension of 1-methyl-1H-pyrrole-2-carboxylic acid (2 g, 15.98 mmol) in acetic anhydride (12 ml, 127 mmol) cooled to −30° C. The reaction was stirred at −30° C. for 0.5 hours, then at RT for 20 minutes. The mixture was cooled again to −30° C. to precipitate the desired product. The solid was quickly filtered in a frit funnel cooled in dry ice; after a few minutes at room temperature, the solid became deliquescent and resulted in a thick slurry/solution that was collected in a separate flask. The slurry was cooled at −30° C. and washed twice with a mixture of hexane (5 ml) and (iPr)₂O (1 ml). The obtained solid was dried under vacuum, then treated with 2N NaOH till complete dissolution (10 ml) and precipitated again by addition of 37% HCl (20 ml). The solid was filtered, washed with water (10 ml) and finally dried under vacuum for 3 days to yield 1-methyl-4-nitro-1H-pyrrole-2-carboxylic acid (Int. 15) (540 mg, 3.17 mmol, MS/ESI⁺ 170.9 [MH]⁺).

Step 2. Preparation of 1-methyl-4-(phenylsulfonamido)-1H-pyrrole-2-carboxylic acid (Intermediate 16)

1-Methyl-4-nitro-1H-pyrrole-2-carboxylic acid (Int. 15) (350 mg, 2.057 mmol) was dissolved in aqueous 1M sodium carbonate (15 ml, 15.00 mmol); 10% Pd/C (219 mg) was added, and the mixture was hydrogenated in a Parr apparatus at 40 psi for 2 hours. The catalyst was filtered off maintaining the mixture under nitrogen flow and the filtrate was collected in a cooled flask (ice bath). THF (20 ml) and benzenesulfonyl chloride (0.318 ml, 2.469 mmol) were added to the cooled solution and the resulting mixture was stirred at 0° C. for 0.5 hours and then at RT for 1 hour. The reaction mixture was extracted with Et$_2$O and the organic layer was discarded. The aqueous layer was cautiously acidified by addition of solid KHSO$_4$ to pH=3 and extracted twice with DCM. The combined organic layers were dried over Na$_2$SO$_4$ and the solvent was removed under vacuum to afford 1-methyl-4-(phenylsulfonamido)-1H-pyrrole-2-carboxylic acid (Int. 16) (540 mg, 1.927 mmol, MS/ESI$^+$280.9 [MH]$^+$), which was used without purification.

Step 3. Preparation of (S)-3,5-dichloro-4-(2-(3-(cyclopropylmethoxy)-4-(difluoromethoxy)phenyl)-2-(1-methyl-4-(phenylsulfonamido)-1H-pyrrole-2-carbonyloxy)ethyl)pyridine 1-oxide (Compound 17)

A solution of 1-methyl-4-(phenylsulfonamido)-1H-pyrrole-2-carboxylic acid (Int. 16) (77 mg, 0.274 mmol), (S)-3,5-dichloro-4-(2-(3-(cyclopropylmethoxy)-4-(difluoromethoxy)phenyl)-2-hydroxyethyl)pyridine 1-oxide (115 mg, 0.274 mmol), EDC (79 mg, 0.410 mmol), and DMAP (50.1 mg, 0.410 mmol) in DCM (40 ml) was stirred at RT for 3 days. The mixture was washed twice with 1N HCl and the organic layer was dried over Na$_2$SO$_4$; the solvent was removed under vacuum and the residue was purified by preparative HPLC-Method 1. The obtained product was further purified by trituration with iPrOH and then dissolved in CH$_3$CN and water and evaporated to dryness to afford (S)-3,5-dichloro-4-(2-(3-(cyclopropylmethoxy)-4-(difluoromethoxy)phenyl)-2-(1-methyl-4-(phenylsulfonamido)-1H-pyrrole-2-carbonyloxy)ethyl)pyridine 1-oxide (Compound 17) (56 mg, 0.082 mmol, MS/ESI$^+$682.09 [MH]$^+$, [α$_D$]=-1.5, c=0.46, DCM).

$^1$H NMR (300 MHz, DMSO-d$_6$) δ ppm 9.74 (s, 1H), 8.52 (s, 2H), 7.69-7.79 (m, 2H), 7.50-7.69 (m, 3H), 7.19 (d, 1H), 7.11 (d, 1H), 6.95 (dd, 1H), 6.84 (d, 1H), 7.06 (t, 1H), 6.58 (d, 1H), 6.03 (dd, 1H), 3.92 (dd, 1H), 3.89 (dd, 1H), 3.63 (s, 3H), 3.49 (dd, 1H), 3.25 (dd, 1H), 1.06-1.32 (m, 1H), 0.45-0.72 (m, 2H), 0.17-0.45 (m, 2H).

The compound listed in Table 2 was prepared according to analogous procedures as described above and depicted in Scheme 4, Step 1-3, by reacting the appropriate precursors (commercially available or synthesized by a person skilled in the art) with suitable reagents, and where purification step has been performed as indicated in Table 2.

Example 5

Synthesis of (S)-4-(2-(1H-pyrrole-2-carbonyloxy)-2-(3-(cyclopropylmethoxy)-4-(difluoromethoxy)phenyl)ethyl)-3,5-dichloropyridine 1-oxide (Compound 20)

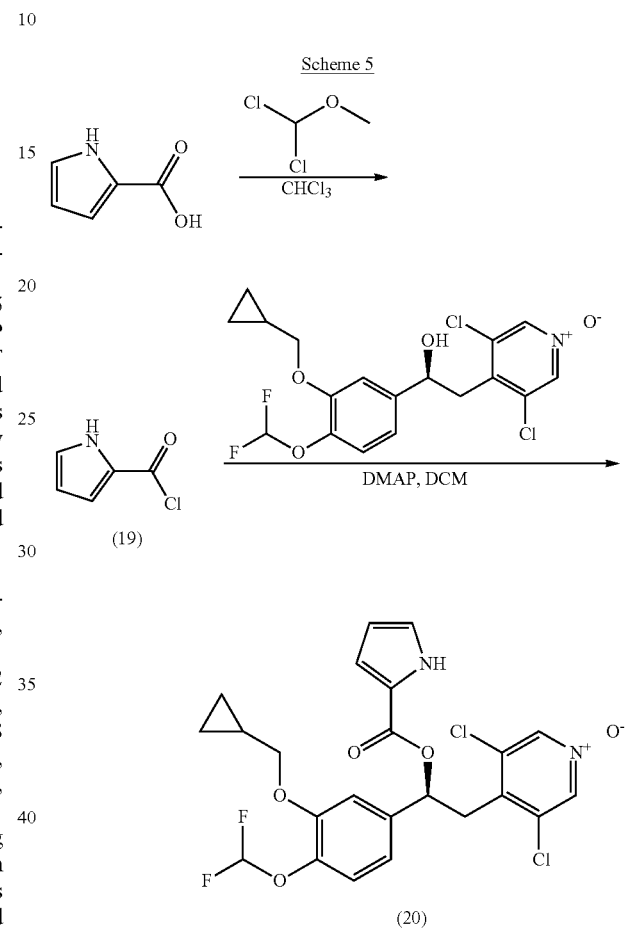

Scheme 5

TABLE 2

| Structure | Compound | NMR characterization | MS/ESI$^+$ [MH]$^+$ [α$_D$] | Starting Material [and conditions, if different] | Purification method |
| --- | --- | --- | --- | --- | --- |
| 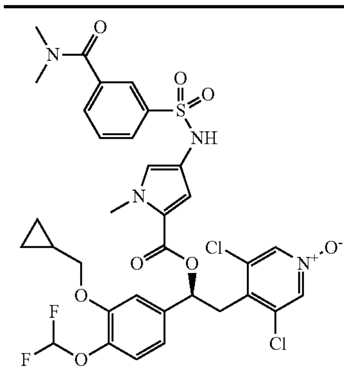 | 18 | $^1$H NMR (300 MHz, DMSO-d$_6$) δ ppm 9.78 (s, 1 H), 8.52 (s, 2 H), 7.73-7.84 (m, 1 H), 7.61-7.72 (m, 3 H), 7.20 (d, 1 H), 7.12 (d, 1 H), 6.96 (dd, 1 H), 6.86 (d, 1 H), 7.06 (t, 1 H), 6.57 (d, 1 H), 6.03 (dd, 1 H), 3.92 (dd, 1 H), 3.88 (dd, 1 H), 3.63 (s, 3 H), 3.49 (dd, 1 H), 3.24 (dd, 1 H), 2.96 (br. s., 3 H), 2.72 (br. s., 3 H), 1.13-1.32 (m, 1 H), 0.48-0.66 (m, 2 H), 0.28-0.43 (m, 2 H) | 753.26 [α$_D$] = −3.2 (c = 0.56, DCM) | Intermediate of Step 2<br><br>Step 3: RT o.n. then additional carboxylic acid (1 eq), EDC (1.2 eq) and DMAP (1.2 eq) were added in order to force the reaction to go to completion | Preparative HPLC-Method 1 |

Step 1. Preparation of 1H-pyrrole-2-carbonyl chloride (Intermediate 19)

To a solution of 1H-pyrrole-2-carboxylic acid (200 mg, 1.80 mmol) in CHCl₃ (5 ml), dichloromethyl methyl ether (3.8 g, 3 ml, 33.05 mmol) was added, and the mixture was refluxed for 3 hours. The mixture was allowed to warm to RT and the solvent evaporated under reduced pressure. The crude was taken up with chloroform and evaporated to dryness (×3) to give 1H-pyrrole-2-carbonyl chloride (Int. 19) (200 mg, 1.54 mmol). MS/ESI⁺129.00 [MH]⁺

Step 2. Preparation of (S)-4-(2-(1H-pyrrole-2-carbonyloxy)-2-(3-(cyclopropylmethoxy)-4-(difluoromethoxy)phenyl)ethyl)-3,5-dichloropyridine 1-oxide (Compound 20)

To a solution of (S)-3,5-dichloro-4-(2-(3-(cyclopropylmethoxy)-4-(difluoromethoxy)phenyl)-2-hydroxyethyl)pyridine 1-oxide (30 mg, 0.071 mmol) and 1H-pyrrole-2-carbonyl chloride (Int. 19) (200 mg, 1.54 mmol) in dry DCM (5 ml), DMAP (20 mg, 0.164 mmol) was added. The mixture was stirred overnight at RT. The mixture was diluted with DCM and washed with HCl 1N. The organic phase was dried over Na₂SO₄ and evaporated to dryness; the crude was purified by preparative HPLC-Method 2 to give (S)-4-(2-(1H-pyrrole-2-carbonyloxy)-2-(3-(cyclopropylmethoxy)-4-(difluoromethoxy)phenyl)ethyl)-3,5-dichloropyridine 1-oxide (Compound 20) (20 mg, 0.039 mmol, MS/ESI⁺513.32 [MH]⁺, [α$_D$]=−20.61, c=0.59, DCM)

¹H NMR (400 MHz, acetone) δ ppm 10.92 (br. s., 1H), 8.26 (s, 2H), 7.27 (d, J=1.96 Hz, 1H), 7.11-7.22 (m, 2H), 7.07 (td, J=2.75, 1.59 Hz, 1H), 6.98 (ddd, J=3.79, 2.38, 1.53 Hz, 1H), 6.90 (t, J=75.00 Hz, 1H), 6.27 (dd, J=9.41, 4.77 Hz, 1H), 6.22 (dt, J=3.76, 2.40 Hz, 1H), 3.90-4.04 (m, 2H), 3.65 (dd, J=14.00, 9.35 Hz, 1H), 3.39 (dd, J=14.00, 4.83 Hz, 1H), 1.21-1.32 (m, 1H), 0.47-0.65 (m, 2H), 0.31-0.44 (m, 2H).

The compound listed in Table 3 was prepared according to an analogous synthetic procedure as described above and depicted in Scheme 5, Step 1, by reacting the appropriate precursors (commercially available or synthesized by a person skilled in the art) with suitable reagents, and where purification step has been performed as indicated in Table 3.

Example 6

Synthesis of (S)-3,5-dichloro-4-(2-(3-(cyclopropylmethoxy)-4-(difluoromethoxy)phenyl)-2-(5-methyl-thiophene-2-carbonyloxy)-ethyl)pyridine 1-oxide (Compound 22)

Scheme 6

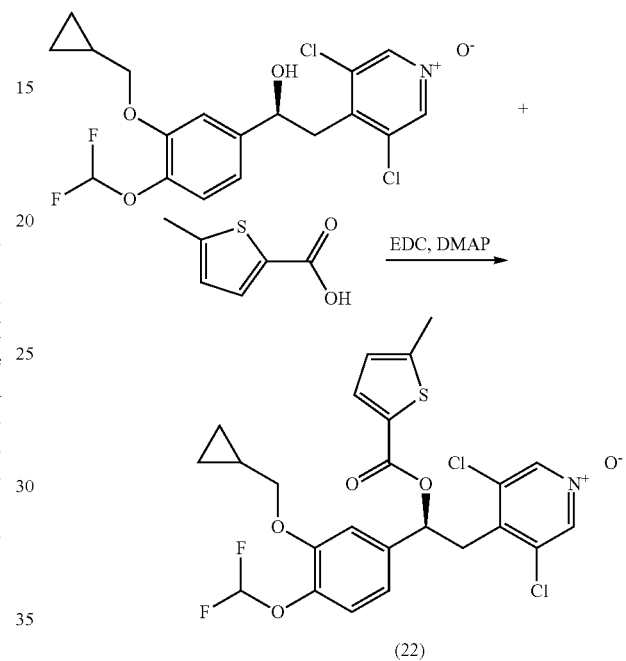

Preparation of (S)-3,5-dichloro-4-(2-(3-(cyclopropylmethoxy)-4-(difluoromethoxy)phenyl)-2-(5-methyl-thiophene-2-carbonyloxy)ethyl)pyridine 1-oxide (Compound 22)

A mixture of (S)-3,5-dichloro-4-(2-(3-(cyclopropylmethoxy)-4-(difluoromethoxy)phenyl)-2-hydroxyethyl)pyridine 1-oxide (100 mg, 0.238 mmol), 5-methylthiophene-

TABLE 3

| Structure | Compound | NMR characterization | MS/ESI⁺ [MH]⁺ [α$_D$] | Starting Material [and conditions, if different] | Purification method |
|---|---|---|---|---|---|
| 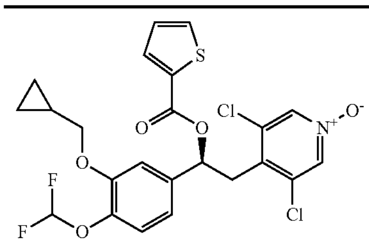 | 21 | ¹H NMR (300 MHz, DMSO-d₆) δ ppm 8.56 (s, 2 H), 7.99 (dd, 1 H), 7.85 (dd, 1 H), 7.17-7.25 (m, 3 H), 7.07 (dd, 1 H), 7.07 (t, 1 H), 6.16 (dd, 1 H), 3.93 (d, 2 H), 3.59 (dd, 1 H), 3.33 (dd, 1 H), 1.11-1.30 (m, 1 H), 0.49-0.61 (m, 2H), 0.20-0.42 (m, 2 H) | 529.87 [αD] = −20.61, c = 0.59, DCM | After 18 hrs stirring at RT, additional thiophene-2-carbonyl chloride (1.1 eq.) and DMAP (1.1 eq.) were added and the reaction was stirred at RT for further 24 hours. The mixture was diluted with DCM and washed with aqueous sat. NH4Cl, 5% NaHCO3 and water. | flash chromatography on silica gel Isolute cartridge (DCM/EtOAc = 9/1) 82% yield |

2-carboxylic acid (40.6 mg, 0.286 mmol), EDC (137 mg, 0.714 mmol) and DMAP (29.1 mg, 0.238 mmol) in DCM (10 ml) was stirred overnight at RT. The reaction was diluted with DCM, washed with 1N HCl, then with aqueous 5% NaHCO$_3$ and finally with brine. The organic phase was dried over sodium sulfate and solvent was evaporated; the crude was purified by flash chromatography on silica gel (DCM, then DCM/EtOAc=3/1) and the obtained amorphous was treated with MeOH and evaporated to give (S)-3,5-dichloro-4-(2-(3-(cyclopropylmethoxy)-4-(difluoromethoxy)phenyl)-2-(5-methylthiophene-2-carbonyloxy)ethyl) pyridine 1-oxide (Compound 22) (114 mg, 0.209 mmol, MS/ESI$^+$ 544.17 [MH]$^+$, [α$_D$]=−68.2, c=0.5, CHCl$_3$).

$^1$H NMR (300 MHz, DMSO-d$_6$) δ ppm 8.56 (s, 2H), 7.67 (d, 1H), 7.21 (d, 1H), 7.18 (d, 1H), 7.05 (dd, 1H), 6.94 (dd, 2H), 6.14 (dd, 1H), 3.93 (d, 2H), 3.56 (dd, 1H), 3.31 (dd, 1H), 1.03-1.32 (m, 1H), 0.45-0.69 (m, 2H), 0.16-0.44 (m, 2H).

The compounds reported in Table 4 were prepared according to analogous procedures to that described above in Example 6, Scheme 6 by using appropriate starting materials.

The compound 82 reported in Table 4a was prepared according to an analogous procedure to that described above in Example 6, Scheme 6 by using, as starting material, the suitable alcohol (S)-3,5-dichloro-4-(2-(3,4-dimethoxyphenyl)-2-hydroxyethyl)-pyridine 1-oxide, prepared as described in WO 2012/168226, which is incorporated herein by reference in its entirety (Example 18, Scheme 24, compound 170).

TABLE 4

| Structure | Compound | NMR characterization | MS/ESI$^+$ [MH]$^+$ | [α$_D$] | Purification |
|---|---|---|---|---|---|
| 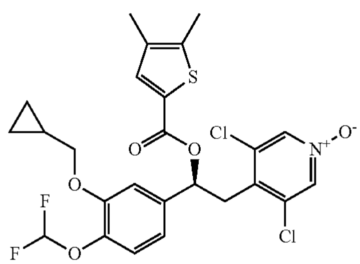 [SMILES: Cc1cc(C(=O)O[C@@H](Cc2c(Cl)c[n+]([O-])cc2Cl)c2ccc(OC(F)F)c(OCC3CC3)c2)sc1C] | 23 | $^1$H NMR (300 MHz, DMSO-d$_6$) δ ppm 8.55 (s, 2 H) 7.57 (s, 1 H) 7.21 (d, 1 H) 7.17 (d, 1 H) 7.04 (dd, 1 H) 7.06 (t, 1 H) 6.14 (dd, 1 H) 3.92 (d, 2 H) 3.54 (dd, 1 H) 3.31 (dd, 1 H) 2.36 (s, 3 H) 2.11 (s, 3 H) 1.05-1.33 (m, 1 H) 0.49-0.65 (m, 2 H) 0.30-0.42 (m, 2 H) | 558.04 | −26.24 c = 0.5 DCM | preparative HPLC - Method 3 |
| 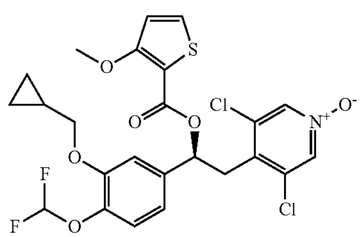 [SMILES: COc1ccsc1C(=O)O[C@@H](Cc1c(Cl)c[n+]([O-])cc1Cl)c1ccc(OC(F)F)c(OCC2CC2)c1] | 24 | $^1$H NMR (300 MHz, DMSO-d$_6$) δ ppm 8.55 (s, 2 H), 7.87 (d, 1 H), 7.20 (d, 1 H), 7.16 (d, 1 H), 7.11 (d, 1 H), 7.01 (dd, 1 H), 7.05 (t, 1 H), 6.15 (dd, 1 H), 3.89-3.97 (m, 2 H), 3.89 (s, 3 H), 3.50 (dd, 1 H), 3.29 (dd, 1 H), 1.11-1.34 (m, 1 H), 0.50-0.69 (m, 2 H), 0.29-0.44 (m, 2 H) | 560.07 | −42.27, c = 0.52 CHCl$_3$ | Flash chromatography on silica gel (DCM, DCM/EtOAc 3/1) followed by preparative HPLC - Method 1 |
| 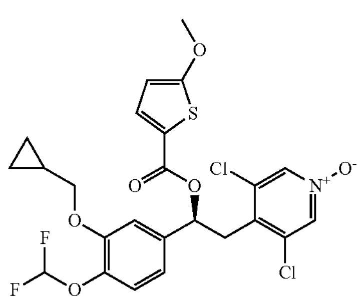 [SMILES: COc1ccc(C(=O)O[C@@H](Cc2c(Cl)c[n+]([O-])cc2Cl)c2ccc(OC(F)F)c(OCC3CC3)c2)s1] | 25 | $^1$H NMR (300 MHz, DMSO-d$_6$) δ ppm 8.56 (s, 2 H) 7.61 (d, 1 H) 7.21 (d, 1 H) 7.17 (d, 1 H) 7.04 (dd, 1 H) 7.06 (t, 1 H) 6.46 (d, 1 H) 6.12 (dd, 1 H) 3.95 (s, 3 H) 3.93 (d, 2 H) 3.54 (dd, 1 H) 3.30 (dd, 1 H) 1.11-1.35 (m, 1 H) 0.47-0.65 (m, 2 H) 0.25-0.46 (m, 2 H) | 560.05 | −33.76, c = 0.49 DCM | Trituration with EtOH |
| 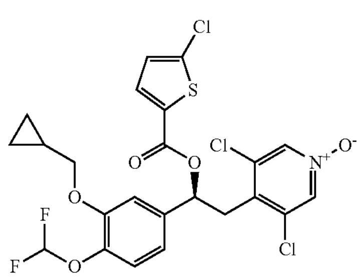 [SMILES: O=C(O[C@@H](Cc1c(Cl)c[n+]([O-])cc1Cl)c1ccc(OC(F)F)c(OCC2CC2)c1)c1ccc(Cl)s1] | 26 | $^1$H NMR (300 MHz, DMSO-d$_6$) δ ppm 8.56 (s, 2 H) 7.74 (d, 1 H) 7.29 (d, 1 H) 7.21 (s, 1 H) 7.19 (d, 1 H) 7.06 (dd, 1 H) 7.07 (t, 1 H) 6.14 (dd, 1 H) 3.93 (d, 2 H) 3.59 (dd, 1 H) 3.32 (dd, 1 H) 1.09-1.32 (m, 1 H) 0.50-0.63 (m, 2 H) 0.30-0.40 (m, 2 H) | 563.86 | −35.44 c = 0.25 DCM | Preparative HPLC - Method 3 |

TABLE 4-continued

| Structure | Compound | NMR characterization | MS/ESI+ [MH]+ | [α_D] | Purification |
|---|---|---|---|---|---|
| 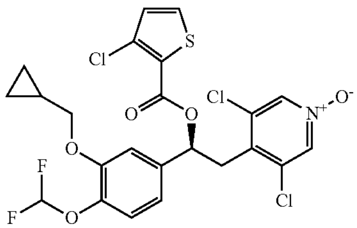 [SMILES: O=C(O[C@@H](Cc1c(Cl)c[n+]([O-])cc1Cl)c1ccc(OC(F)F)c(OCC2CC2)c1)c1sccc1Cl] | 27 | $^1$H NMR (300 MHz, DMSO-d$_6$) δ ppm 8.55 (s, 2 H), 8.05 (d, 1 H), 7.25 (d, 1 H), 7.18-7.24 (m, 2 H), 7.05 (dd, 1 H), 7.07 (t, 1 H), 6.21 (dd, 1 H), 3.92 (d, 2 H), 3.57 (dd, 1 H), 3.33 (dd, 1 H), 1.10-1.34 (m, 1 H), 0.48-0.65 (m, 2 H), 0.24-0.46 (m, 2 H) | 563.99 | −11.64 c = 0.5 DCM | preparative HPLC - Method 3 followed by trituration with iPrOH |
| 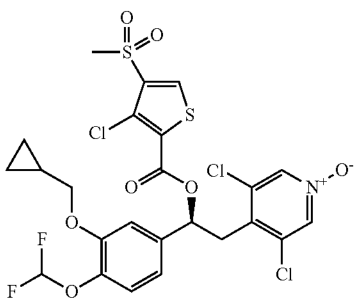 [SMILES: CS(=O)(=O)c1csc(C(=O)O[C@@H](Cc2c(Cl)c[n+]([O-])cc2Cl)c2ccc(OC(F)F)c(OCC3CC3)c2)c1Cl] | 28 | $^1$H NMR (300 MHz, DMSO-d$_6$) δ ppm 8.76 (s, 1 H), 8.56 (s, 2 H), 7.18-7.26 (m, 2 H), 7.07 (dd, 1 H), 7.07 (t, 1 H), 6.22 (dd, 1 H), 3.93 (d, 2 H), 3.61-3.66 (m, 1 H), 3.35 (dd, 1 H), 3.32 (s, 3 H), 1.10-1.32 (m, 1 H), 0.46-0.72 (m, 2 H), 0.21-0.45 (m, 2 H) | 641.9 | −21.67 c = 0.24 DCM | preparative HPLC - Method 3 followed by trituration with iPrOH |
| 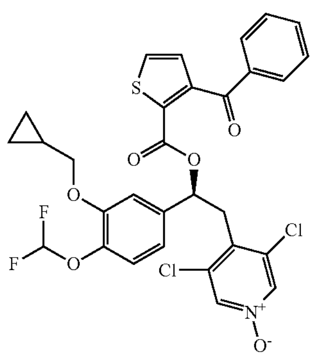 [SMILES: O=C(c1ccccc1)c1ccsc1C(=O)O[C@@H](Cc1c(Cl)c[n+]([O-])cc1Cl)c1ccc(OC(F)F)c(OCC2CC2)c1] | 29 | $^1$H NMR (400 MHz, DMSO-d$_6$) δ ppm 8.51 (s, 2 H), 8.12 (m, 1 H), 7.64 (m, 3 H), 7.45-7.57 (m, 2 H), 7.33 (m, 1 H), 7.08-7.14 (m, 1 H), 7.05 (t, J = 75.00 Hz, 1 H), 6.93-7.00 (m, 1 H), 6.74-6.81 (m, 1 H), 5.91-6.03 (m, 1 H), 3.86 (m, 2 H), 3.26-3.31 (m, 1 H), 3.01-3.13 (m, 1 H), 1.14-1.29 (m, 1 H), 0.49-0.64 (m, 2 H), 0.24-0.41 (m, 2H). | 634.0 | | Preparative HPLC - Method 2 |
| 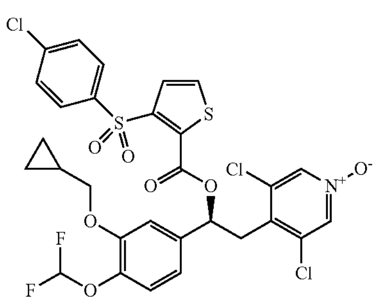 [SMILES: O=C(O[C@@H](Cc1c(Cl)c[n+]([O-])cc1Cl)c1ccc(OC(F)F)c(OCC2CC2)c1)c1sccc1S(=O)(=O)c1ccc(Cl)cc1] | 30 | $^1$H NMR (400 MHz, DMSO-d$_6$) δ ppm 8.62-8.68 (m, 1 H), 8.55-8.60 (m, 1 H), 8.45-8.50 (m, 2 H), 7.74-7.83 (m, 2 H), 7.58-7.66 (m, 2 H), 7.13-7.19 (m, 1 H), 7.09-7.12 (m, 1 H), 7.05 (t, J = 75.00 Hz, 1 H), 6.92-7.01 (m, 1 H), 5.97-6.10 (m, 1 H), 3.81-3.92 (m, 2 H), 3.53-3.58 (m, 1 H), 3.16-3.32 (m, 1 H), 1.11-1.27 (m, 1 H), 0.48-0.60 (m, 2 H), 0.28-0.37 (m, 2 H). | 703.9 | | |
| 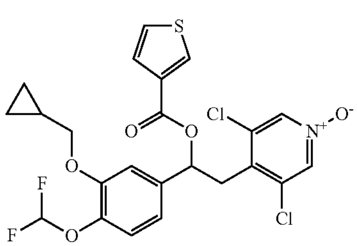 [SMILES: O=C(OC(Cc1c(Cl)c[n+]([O-])cc1Cl)c1ccc(OC(F)F)c(OCC2CC2)c1)c1ccsc1] | 31 | $^1$H NMR (300 MHz, DMSO-d$_6$) δ ppm 8.55 (s, 2 H), 8.41 (dd, 1 H), 7.66 (dd, 1 H), 7.47 (dd, 1 H), 7.20 (d, 1 H), 7.20 (d, 1 H), 7.07 (dd, 1 H), 7.06 (t, 1 H), 6.15 (dd, 1 H), 3.93 (d, 2 H), 3.58 (dd, 1 H), 3.32 (dd, 1 H), 1.11-1.31 (m, 1 H), 0.50-0.66 (m, 2 H), 0.27-0.43 (m, 2 H) | 529.82 | −30 c = 0.53 DCM | Trituration with iPrOH |

TABLE 4a

| Structure | Compound | NMR characterization | MS/ESI+ [MH]+ | [α_D] | Purification |
|---|---|---|---|---|---|
| 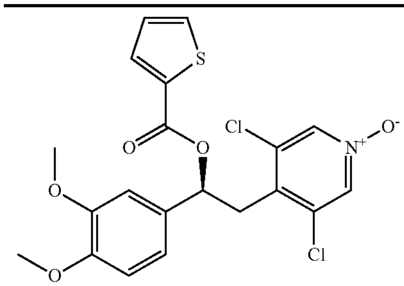 | 82 | $^1$H NMR (300 MHz, DMSO-d$_6$) δ ppm 8.55 (s, 2 H), 7.07 (dd, 1 H), 7.83 (dd, 1 H), 7.22 (dd, 1 H), 6.91-7.08 (m, 3H), 6.16 (dd, 1 H), 3.78 (s, 3 H), 3.76 (s, 3 H), 3.60 (dd, 1 H), 3.32 (dd, 1 H) | 454.14 | −38.79 c = 0.43 DCM | Flash chromatography on silica gel cartridge (DCM: EtOAc = 80:20 to 70:30), then preparative HPLC - Method 3 |

Example 7

Synthesis of (S)-3,5-dichloro-4-(2-(3-(cyclopropyl-methoxy)-4-(difluoromethoxy)phenyl)-2-(3-(N-methylsulfamoyl)thiophene-2-carbonyloxy-ethyl) pyridine 1-oxide (Compound 36)

added and the reaction was stirred for 1 hour at RT. The mixture was partitioned between 2N HCl and DCM and the aqueous phase was extracted with DCM. The combined organic layers were dried over sodium sulfate and the solvent was removed affording methyl 3-(N-methylsulfamoyl)thiophene-2-carboxylate (Int. 32) (430 mg, 1.828 mmol, MS/ESI$^+$235.8 [MH]$^+$).

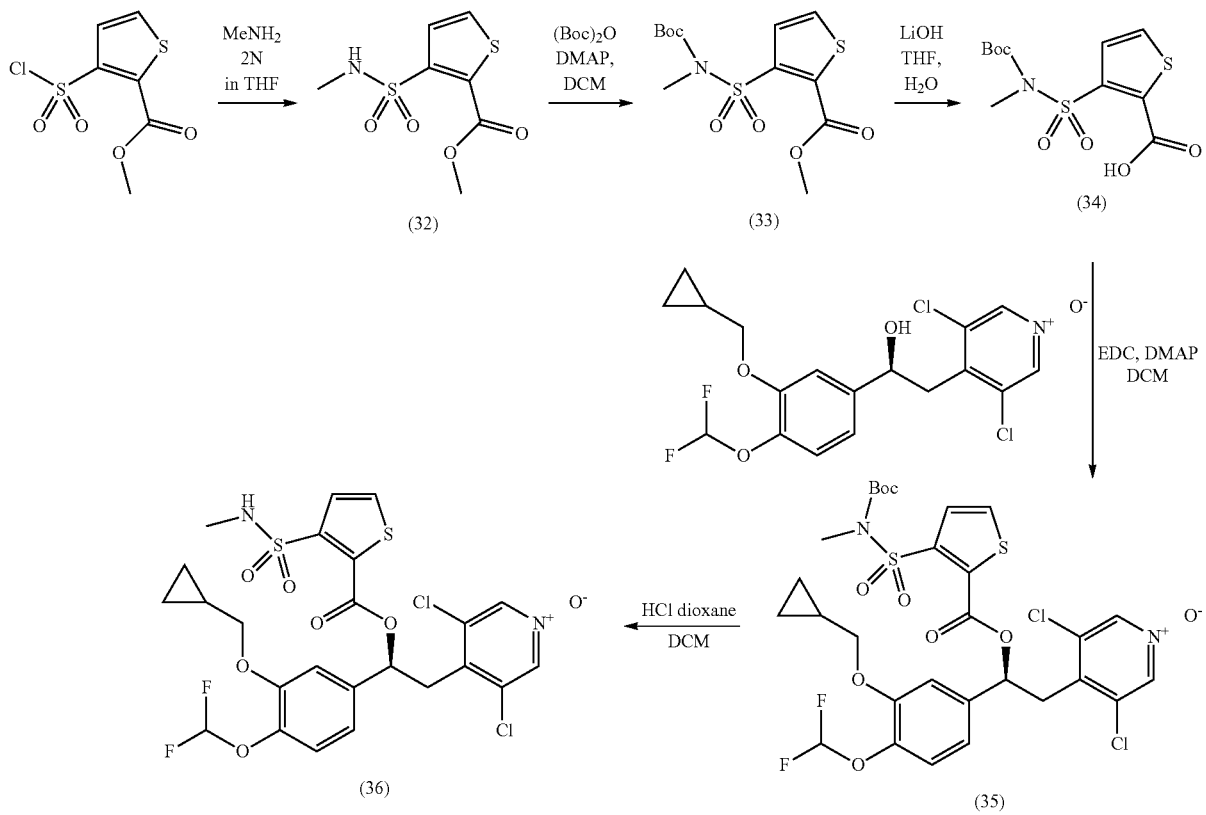

Scheme 7

Step 1. Preparation of methyl 3-(N-methylsulfamoyl)thiophene-2-carboxylate (Intermediate 32)

To a solution of methyl 3-(chlorosulfonyl)thiophene-2-carboxylate (500 mg, 2.077 mmol) in DCM (20 ml), methanamine 2N solution in THF (4.155 ml, 8.31 mmol) was

Step 2. Preparation of methyl 3-(N-(tert-butoxycarbonyl)-N-methylsulfamoyl)thiophene-2-carboxylate (Int. 33)

To a solution of methyl 3-(N-methylsulfamoyl)thiophene-2-carboxylate (Int. 32) (430 mg, 1.828 mmol) in DCM (20 ml) DMAP (246 mg, 2.010 mmol) and di-tert-butyldicarbonate (399 mg, 1.828 mmol) were added and the reaction was stirred overnight at RT. The mixture was partitioned between water and DCM, and the aqueous phase was extracted with DCM (×3); the combined organic layers were dried over sodium sulfate and the solvent was removed yielding methyl 3-(N-(tert-butoxycarbonyl)-N-methylsulfamoyl)thiophene-2-carboxylate (Int. 33) which was used without any additional purification (500 mg, 1.491 mmol, MS/ESI⁺357.8 [MNa]⁺).

Step 3. Preparation of 3-(N-(tert-butoxycarbonyl)-N-methylsulfamoyl)thiophene-2-carboxylic acid (Intermediate 34)

To a solution of methyl 3-(N-(tert-butoxycarbonyl)-N-methylsulfamoyl)-thiophene-2-carboxylate (Int. 33) (500 mg, 1.491 mmol) in a mixture of THF and H₂O 1/1 (100 ml), lithium hydroxide (357 mg, 14.91 mmol) was added, and the reaction was stirred at RT for 2 hours. The organic solvent was evaporated under vacuum and the aqueous residue was acidified with 1N HCl (pH=4). The resulting precipitate was collected by filtration recovering 3-(N-(tert-butoxycarbonyl)-N-methylsulfamoyl)-thiophene-2-carboxylic acid (Int. 34) (370 mg, 1.151 mmol, MS/ESI⁺343.8 [MNa]⁺).

Step 4. Preparation of (S)-4-(2-(3-(N-(tert-butoxycarbonyl)-N-methylsulfamoylthiophene-2-carbonyloxy)-2-(3-(cyclopropylmethoxy)-4-(difluoromethoxy)phenyl)ethyl)-3,5-dichloropyridine 1-oxide (Intermediate 35)

To a solution of 3-(N-(tert-butoxycarbonyl)-N-methylsulfamoyl)-thiophene-2-carboxylic acid (Int. 34) (150 mg, 0.467 mmol) in DCM (5 ml), (S)-3,5-dichloro-4-(2-(3-(cyclopropylmethoxy)-4-(difluoromethoxy)phenyl)-2-hydroxyethyl)pyridine 1-oxide (196 mg, 0.467 mmol), EDC (268 mg, 1.400 mmol) and DMAP (28.5 mg, 0.233 mmol) were added and the mixture was reacted at RT overnight. The solvent was removed and the crude was purified by flash chromatography on silica gel (DCM/MeOH=95/5) affording (S)-4-(2-(3-(N-(tert-butoxycarbonyl)-N-methylsulfamoyl)thiophene-2-carbonyloxy)-2-(3-(cyclopropylmethoxy)-4-(difluoromethoxy) phenyl)ethyl)-3,5-dichloropyridine 1-oxide (Int. 35) (230 mg, 0.318 mmol, MS/ESI⁺722.8 [MH]⁺).

Step 5. Preparation of (S)-3,5-dichloro-4-(2-(3-(cyclopropylmethoxy)-4-(difluoromethoxy)phenyl)-2-(3-(N-methylsulfamoyl)thiophene-2-carbonyloxy)ethyl)-pyridine 1-oxide (Compound 36)

To a solution of (S)-4-(2-(3-(N-(tert-butoxycarbonyl)-N-methylsulfamoyl)-thiophene-2-carbonyloxy)-2-(3-(cyclopropylmethoxy)-4-(difluoromethoxy)phenyl)ethyl)-3,5-dichloropyridine 1-oxide (Int. 35) (230 mg, 0.318 mmol) in DCM (10 ml), HCl 4M in dioxane (0.795 ml, 3.18 mmol) was added, and the mixture stirred at RT for 48 hours. The solvent was evaporated and the resulting crude was purified by preparative HPLC-Method 3 to obtain (S)-3,5-dichloro-4-(2-(3-(cyclopropylmethoxy)-4-(difluoromethoxy)-phenyl)-2-(3-(N-methylsulfamoyl)thiophene-2-carbonyloxy)ethyl)pyridine 1-oxide (Compound 36) (71.3 mg, 0.114 mmol, MS/ESI⁺623.02 [MH]⁺, [α$_D$]=−10.04, c=0.5, DCM).

¹H NMR (300 MHz, DMSO-d₆) δ ppm 8.54 (s, 2H), 8.06 (dd, 1H), 7.43 (dd, 1H), 7.21 (d, 1H), 6.99-7.07 (m, 2H), 7.08 (t, 1H), 6.19 (dd, 1H), 3.93 (d, 2H), 3.58 (dd, 1H), 3.37 (dd, 1H), 2.48 (d, 3H), 1.14-1.23 (m, 1H), 0.50-0.63 (m, 2H), 0.28-0.42 (m, 2H)

Example 8

Synthesis of (S)-3,5-dichloro-4-(2-(3-(cyclopropylmethoxy)-4-(difluoromethoxy)phenyl)-2-(3-(methylsulfonamido)thiophene-2-carbonyloxy)ethyl)-pyridine 1-oxide (Compound 39)

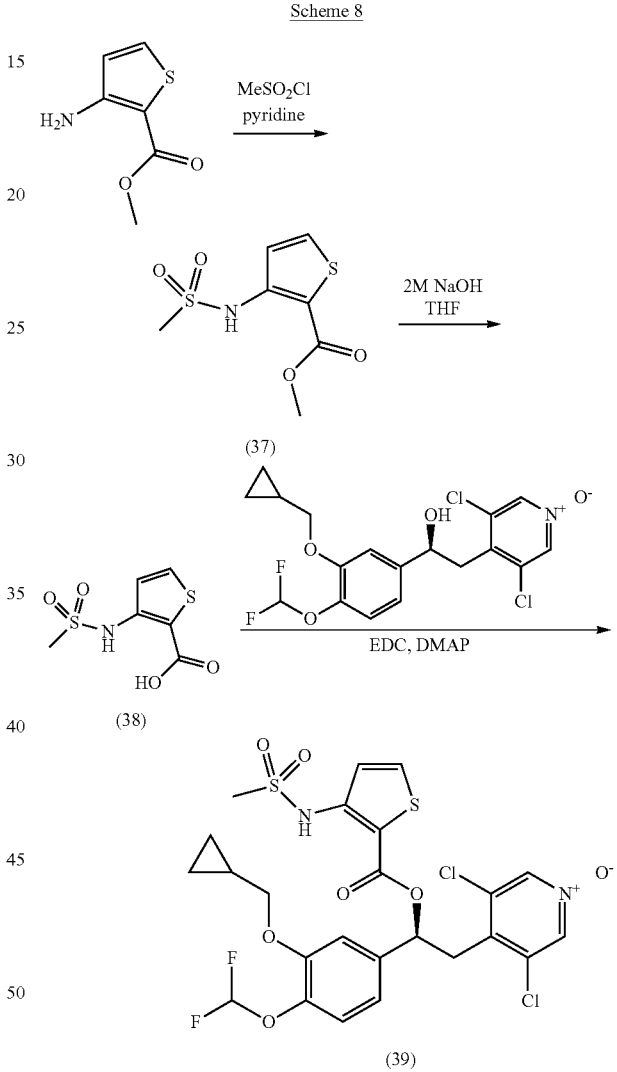

Scheme 8

Step 1. Preparation of methyl 3-(methylsulfonamido)thiophene-2-carboxylate (Intermediate 37)

To a solution of methyl 3-aminothiophene-2-carboxylate (1.013 g, 6.44 mmol) in pyridine (15 ml) cooled to 0° C., methanesulfonyl chloride (0.552 ml, 7.09 mmol) was added, and the reaction was stirred at RT for 4 hours. Additional methanesulfonyl chloride (0.100 ml, 1.289 mmol) was added, and the stirring was continued overnight at RT. The solvent was evaporated, and the residue was partitioned between EtOAc and 1N HCl; the organic layer was washed with 1N HCl, dried over Na$_2$SO$_4$ and evaporated. The crude was triturated with Et$_2$O/DCM 95/5 to afford methyl 3-(methylsulfonamido)-thiophene-2-carboxylate (Intermediate 37) (1.272 g, 5.41 mmol, MS/ESI$^+$235.9 [MH]$^+$).

Step 2. Preparation of 3-(methylsulfonamido)thiophene-2-carboxylic acid (Intermediate 38)

A mixture of methyl 3-(methylsulfonamido)thiophene-2-carboxylate (Int. 37) (193 mg, 0.820 mmol) in aqueous 2M NaOH (4.10 ml, 8.20 mmol) and THF (4.1 ml) was heated under microwaves irradiation at 80° C. for 30 minutes. 2N HCl was added (pH=2) and the mixture was extracted with EtOAc (×3). The combined organic layers were dried over Na$_2$SO$_4$ and evaporated to dryness affording 3-(methylsulfonamido)thiophene-2-carboxylic acid (Int. 38) (180 mg, 0.814 mmol, MS/ESI$^+$221.8 [MH]$^+$).

Step 3. Preparation of (S)-3,5-dichloro-4-(2-(3-(cyclopropylmethoxy)-4-(difluoromethoxy)phenyl)-2-(3-(methylsulfonamido)thiophene-2-carbonyloxy)ethyl)-pyridine 1-oxide (Compound 39)

A mixture of 3-(methylsulfonamido)thiophene-2-carboxylic acid (Int. 38) (110 mg, 0.497 mmol), (S)-3,5-dichloro-4-(2-(3-(cyclopropylmethoxy)-4-(difluoromethoxy)-phenyl)-2-hydroxyethyl)pyridine 1-oxide (209 mg, 0.497 mmol), EDC (286 mg, 1.491 mmol) and DMAP (30.4 mg, 0.249 mmol) in DCM (25 ml) was stirred at RT for 3 days. The mixture was diluted with DCM and washed with 1N HCl and aqueous NaHCO$_3$; the organic layer was dried over Na$_2$SO$_4$, filtered and evaporated. The crude was purified by flash chromatography on silica gel cartridge (DCM/MeOH=99.5/0.5 to 99/1) affording (S)-3,5-dichloro-4-(2-(3-(cyclopropylmethoxy)-4-(difluoromethoxy)-phenyl)-2-(3-(methylsulfonamido)thiophene-2-carbonyloxy)ethyl) pyridine 1-oxide (Int. 39) (95 mg, 0.152 mmol, MS/ESI$^+$ 623.05 [MH]$^+$, [α$_D$]=−28.6, c=0.3, DCM).

$^1$H NMR (300 MHz, DMSO-d$_6$) δ ppm 8.57 (s, 3H) 7.97 (d, 1H) 7.27 (d, 1H) 7.23 (d, 1H) 7.19 (d, 1H) 7.04 (dd, 1H) 6.94 (t, 1H) 6.16 (dd, 1H) 3.93 (d, 2H) 3.58 (dd, 1H) 3.34-3.45 (m, 1H) 3.16 (s, 3H) 1.04-1.35 (m, 1H) 0.49-0.65 (m, 2H) 0.24-0.42 (m, 2H).

Example 9

Synthesis of (S)-3,5-dichloro-4-(2-(3-(cyclopropylmethoxy)-4-(difluoromethoxy)phenyl)-2-(4-(methylsulfonamido)thiophene-2-carbonyloxy)-ethyl)pyridine 1-oxide (Compound 46)

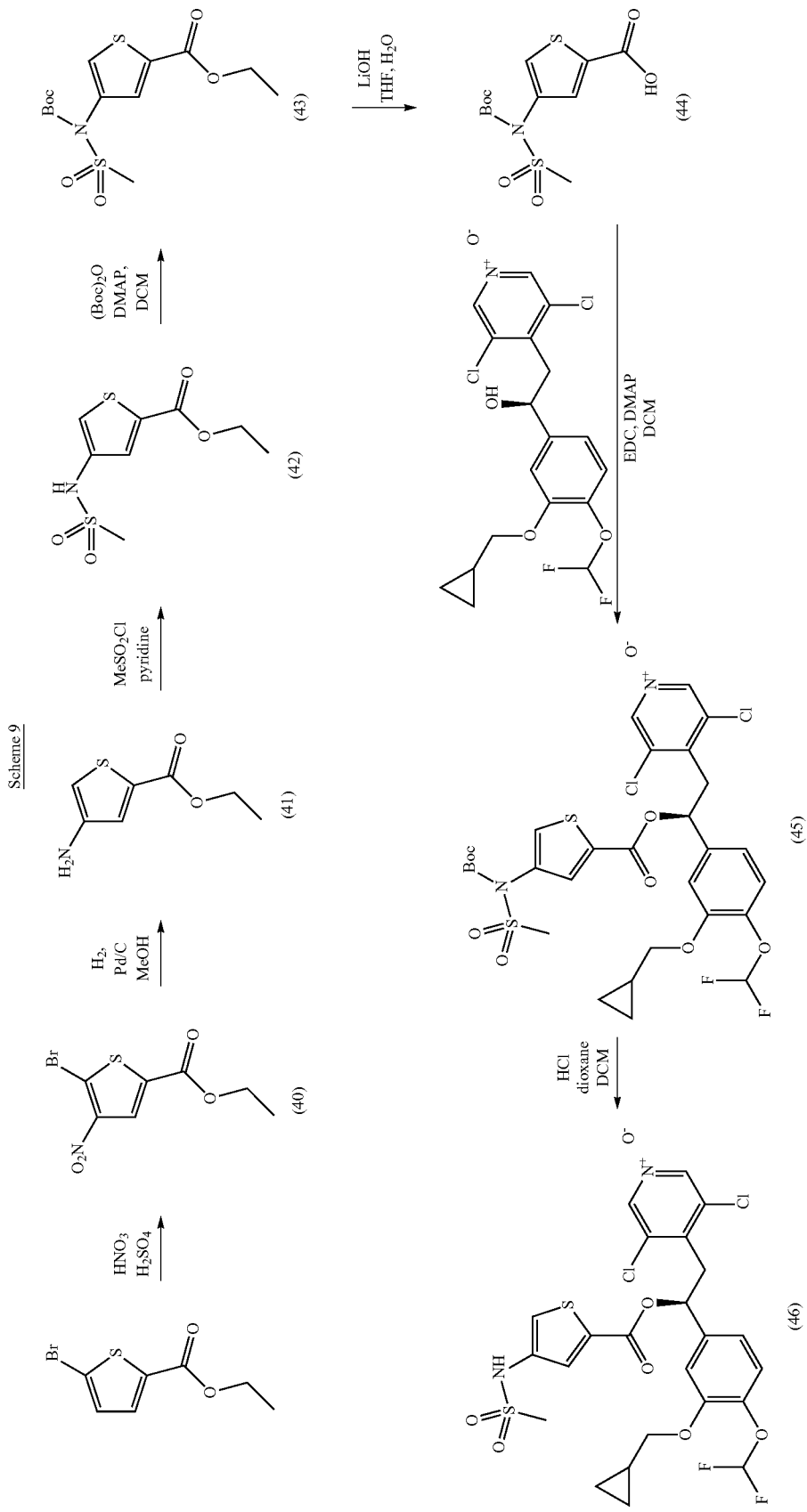

Step 1. Preparation of ethyl 5-bromo-4-nitrothiophene-2-carboxylate (Intermediate 40)

To a solution of ethyl 5-bromothiophene-2-carboxylate (1.5 g, 6.38 mmol) in aqueous conc. $H_2SO_4$ (6 ml) cooled to 0° C., aqueous 65% $HNO_3$ (2 ml) was added, and the reaction was left to warm to RT and stirred for 1 hour. The mixture was poured into ice-water and extracted with EtOAc (×3); the combined organic layers were dried over sodium sulfate and the solvent was removed affording ethyl 5-bromo-4-nitrothiophene-2-carboxylate (Int. 40) which was used without any additional purification (550 mg, 1.964 mmol).

Step 2. Preparation of ethyl 4-aminothiophene-2-carboxylate (Intermediate 41)

A solution of ethyl 5-bromo-4-nitrothiophene-2-carboxylate (Int. 40) (500 mg, 1.785 mmol) in MeOH (35 ml) was hydrogenated in a continuous-flow hydrogenation reactor (H-Cube apparatus) (flow rate: 1.0 ml/min, Temp: 50° C., $H_2$ pressure: 20 bar). The solvent was evaporated affording ethyl 4-aminothiophene-2-carboxylate (Int. 41) which was used without any additional purification (350 mg, MS/ESI$^+$ 172.1 [MH]$^+$).

Step 3. Preparation of ethyl 4-(methylsulfonamido)thiophene-2-carboxylate (Intermediate 42)

To a solution of ethyl 4-aminothiophene-2-carboxylate (Int. 41) (theoretical 1.785 mmol) in pyridine (20 ml), methanesulfonyl chloride (0.239 ml, 3.07 mmol) was added and the mixture was stirred overnight at RT. The solvent was evaporated and the residue was partitioned between 1N HCl and EtOAc; the aqueous phase was extracted with EtOAc and the combined organic layers were dried over sodium sulfate and evaporated to afford ethyl 4-(methylsulfonamido)thiophene-2-carboxylate (Int. 42) which was used without any additional purification (370 mg, 1.484 mmol, MS/ESI$^+$ 249.8 [MH]$^+$).

Step 4. Preparation of ethyl 4-(N-(tert-butoxycarbonyl)-methylsulfonamido)thiophene-2-carboxylate (Intermediate 43)

To a solution of ethyl 4-(methylsulfonamido)thiophene-2-carboxylate (22) (370 mg, 1.484 mmol) in DCM (20 ml), DMAP (272 mg, 2.226 mmol) and di-tert-butyldicarbonate (486 mg, 2.226 mmol) were added, and the mixture was stirred at RT for 5 hours. The solvent was removed and the crude was purified by flash chromatography on silica gel (Hexane/EtOAc=1/1) yielding ethyl 4-(N-(tert-butoxycarbonyl)-methylsulfonamido)thiophene-2-carboxylate (Int. 43) (300 mg, 0.859 mmol).

Step 5. Preparation of 4-(N-(tert-butoxycarbonyl)-methylsulfonamido)thiophene-2-carboxylic acid (Intermediate 44)

To a solution of ethyl 4-(N-(tert-butoxycarbonyl)methyl-sulfonamido)-thiophene-2-carboxylate (Int. 43) (300 mg, 0.859 mmol) in THF/water 1/1 (20 ml), lithium hydroxide (61.7 mg, 2.58 mmol) was added, and the mixture was reacted overnight at RT. The organic solvent was evaporated and the aqueous residue was acidified with 1N HCl (pH=5); the resulting precipitate was collected by filtration yielding 4-(N-(tert-butoxycarbonyl)-methylsulfonamido)thiophene-2-carboxylic acid (Int. 44) (220 mg, 0.685 mmol, MS/ESI$^+$ 343.7 [MNa]$^+$).

Step 6. Preparation of (S)-4-(2-(4-(N-(tert-butoxycarbonyl)-methylsulfonamido)thiophene-2-carbonyloxy)-2-(3-(cyclopropylmethoxy)-4-(difluoromethoxy)phenyl)ethyl)-3,5-dichloropyridine 1-oxide (Intermediate 45)

To a solution of 4-(N-(tert-butoxycarbonyl)methylsulfonamido)-thiophene-2-carboxylic acid (Int. 44) (100 mg, 0.311 mmol) in DCM (5 ml), (S)-3,5-dichloro-4-(2-(3-(cyclopropylmethoxy)-4-(difluoromethoxy)phenyl)-2-hydroxyethyl)pyridine 1-oxide (131 mg, 0.311 mmol), EDC (179 mg, 0.934 mmol) and DMAP (19.01 mg, 0.156 mmol) were added, and reaction was stirred at RT overnight. The mixture was diluted with DCM (10 ml) and washed with 1N HCl; the aqueous phase was extracted with EtOAc and the combined organic layers were dried over sodium sulfate. The solvent was removed under vacuum and the crude was purified by flash chromatography on silica gel (DCM/MeOH=98/2) affording (S)-4-(2-(4-(N-(tert-butoxycarbonyl)methylsulfonamido)thiophene-2-carbonyloxy)-2-(3-(cyclopropylmethoxy)-4-(difluoromethoxy)phenyl)ethyl)-3,5-dichloropyridine 1-oxide (Int. 45) (72 mg, 0.100 mmol, MS/ESI$^+$722.9 [MH]$^+$).

Step 7. Preparation of (S)-3,5-dichloro-4-(2-(3-(cyclopropylmethoxy)-4-(difluoromethoxy)phenyl)-2-(4-(methylsulfonamido)thiophene-2-carbonyloxy)ethyl) pyridine 1-oxide (Compound 46)

To a solution of (S)-4-(2-(4-(N-(tert-butoxycarbonyl)-methylsulfonamido)-thiophene-2-carbonyloxy)-2-(3-(cyclopropylmethoxy)-4-(difluoromethoxy)phenyl)ethyl)-3,5-dichloropyridine 1-oxide (Int. 5) (72 mg, 0.100 mmol) in DCM (5 ml), HCl 4M in dioxane (0.249 ml, 0.995 mmol) was added and the mixture was reacted overnight at RT. The solvent was removed and the crude, was triturated with MeOH; a further purification by preparative HPLC (Method 3) was required to obtain (S)-3,5-dichloro-4-(2-(3-(cyclopropylmethoxy)-4-(difluoromethoxy)phenyl)-2-(4-(methyl-sulfonamido)-thiophene-2-carbonyloxy)ethyl)pyridine 1-oxide (Compound 46) (30.3 mg, 0.049 mmol, MS/ESI$^+$ 623.05 [MH]$^+$, $[\alpha_D]$=−29.28, c=0.25, DCM).

$^1$H NMR (300 MHz, DMSO-d$_6$) δ ppm 10.06 (s, 1H), 8.55 (s, 2H), 7.60 (d, 1H), 7.40 (d, 1H), 7.22 (d, 1H), 7.19 (d, 1H), 7.05 (dd, 1H), 7.07 (t, 1H), 6.13 (dd, 1H), 3.93 (d, 2H), 3.59 (dd, 1H), 3.32 (dd, 1H), 3.00 (s, 3H), 1.12-1.32 (m, 1H), 0.48-0.62 (m, 2H), 0.27-0.44 (m, 2H)

Example 10

Synthesis of (S)-3,5-dichloro-4-(2-(3-(cyclopropylmethoxy)-4-(difluoromethoxy)phenyl)-2-(3-(N-methyl-N-(2-morpholinoethyl)-sulfamoyl)thiophene-2-carbonyloxy)ethyl)pyridine 1-oxide (Compound 49)

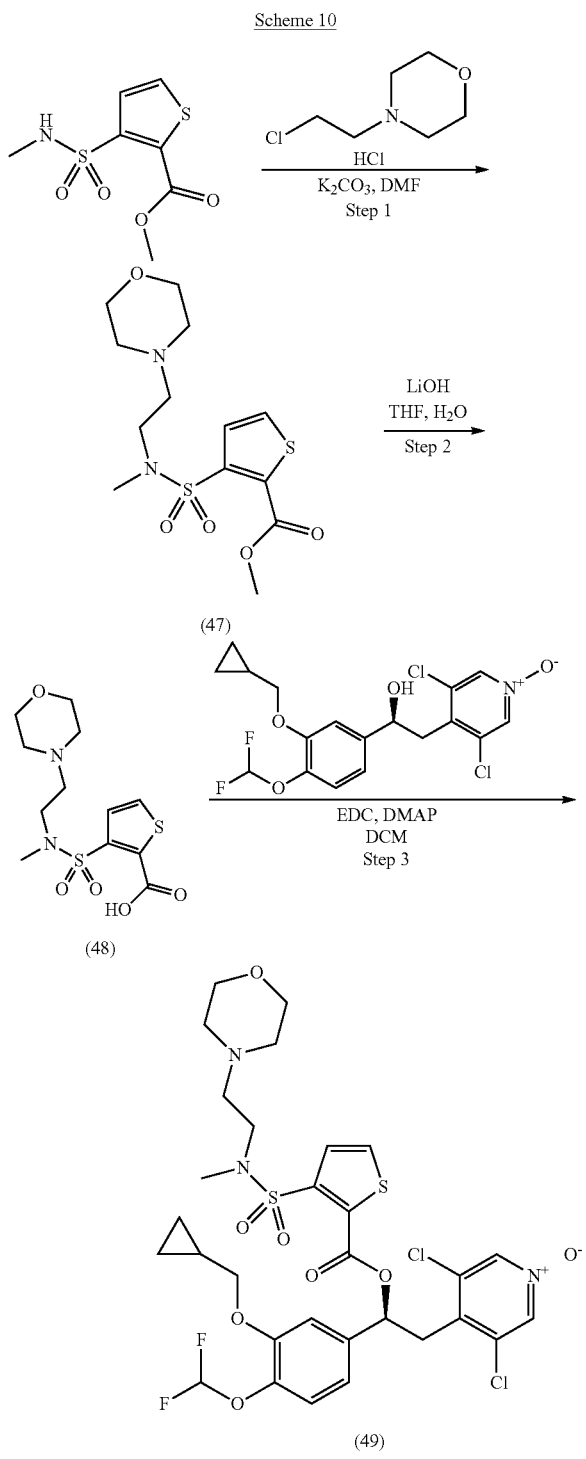

Step 1. Preparation of methyl 3-(N-methyl-N-(2-morpholinoethyl)sulfamoyl)thiophene-2-carboxylate (Intermediate 47)

To a solution of methyl 3-(N-methylsulfamoyl)thiophene-2-carboxylate (prepared in an analogous manner as described in Example 10, Scheme 10, Step 1, 530 mg, 2.253 mmol) in dry DMF (20 ml) under nitrogen atmosphere, $K_2CO_3$ (623 mg, 4.51 mmol) and 4-(2-chloroethyl)morpholine hydrochloride (838 mg, 4.51 mmol) were added, and the mixture was reacted at 60° C. overnight and then at 80° C. for 5 hours. The insoluble inorganic salts were filtered off, the filtrate was evaporated and the residue was purified by flash chromatography on silica gel (DCM/MeOH=9/1) to afford methyl 3-(N-methyl-N-(2-morpholinoethyl)sulfamoyl)thiophene-2-carboxylate (Int. 47) (510 mg, 1.464 mmol, MS/ESI⁺348.8 [MH]⁺).

Step 2. Preparation of 3-(N-methyl-N-(2-morpholinoethyl)sulfamoyl)thiophene-2-carboxylic acid (Int. 48)

To a solution of methyl 3-(N-methyl-N-(2-morpholinoethyl)sulfamoyl)-thiophene-2-carboxylate (Int. 47) (510 mg, 1.464 mmol) in a 1:1 mixture of THF and $H_2O$, lithium hydroxide (351 mg, 14.64 mmol) was added, and the mixture was stirred at RT overnight. The organic solvent was evaporated and the aqueous residue was acidified with 2N HCl (pH=7); the precipitate was collected by filtration affording 3-(N-methyl-N-(2-morpholinoethyl)-sulfamoyl)thiophene-2-carboxylic acid (Int. 48) (410 mg, 1.226 mmol, MS/ESI⁺334.9 [MH]⁺).

Step 3. Preparation of (S)-3,5-dichloro-4-(2-(3-(cyclopropylmethoxy)-4-(difluoromethoxy)phenyl)-2-(3-(N-methyl-N-(2-morpholinoethyl)-sulfamoyl)thiophene-2-carbonyloxy)ethyl)pyridine 1-oxide (Compound 49)

To a solution of 3-(N-methyl-N-(2-morpholinoethyl)sulfamoyl)-thiophene-2-carboxylic acid (Int. 48) (95 mg, 0.284 mmol) in DCM (5 ml), (S)-3,5-dichloro-4-(2-(3-(cyclopropylmethoxy)-4-(difluoromethoxy)phenyl)-2-hydroxyethyl)pyridine 1-oxide (119 mg, 0.284 mmol), DMAP (52.1 mg, 0.426 mmol), and EDC (163 mg, 0.852 mmol) were added, and the mixture was stirred overnight at RT. The solvent was evaporated and the residue was purified by filtration through a SCX cartridge (MeOH, then MeOH/conc.$NH_4OH$aq=9/1) to obtain (S)-3,5-dichloro-4-(2-(3-(cyclopropylmethoxy)-4-(difluoromethoxy)phenyl)-2-(3-(N-methyl-N-(2-morpholinoethyl)sulfamoyl)thiophene-2-carbonyloxy)ethyl)pyridine 1-oxide (Compound 49) (70.1 mg, 0.095 mmol, MS/ESI⁺ 736.17 [MH]⁺, $[\alpha_D]$=+8.96, c=0.25, DCM).

¹H NMR (300 MHz, DMSO-$d_6$) δ ppm 8.54 (s, 2H) 8.03 (d, 1H) 7.47 (d, 1H) 7.00-7.27 (m, 3H) 7.07 (t, 1H) 6.18 (dd, 1H) 3.92 (d, 2H) 3.54-3.65 (m, 1H) 3.46-3.54 (m, 4H) 3.36 (dd, 1H) 3.21-3.25 (m, 2H) 2.82 (s, 3H) 2.39 (t, 2H) 2.26-2.35 (m, 4H) 1.19-1.31 (m, 1H) 0.50-0.64 (m, 2H) 0.27-0.40 (m, 2H)

Example 11

Synthesis of (S)-3,5-dichloro-4-(2-(3-(cyclopropylmethoxy)-4-(difluoromethoxy)phenyl)-2-(3-(N-(2-morpholinoethyl)-methylsulfonamido)thiophene-2-carbonyloxy)ethyl)pyridine 1-oxide (Compound 52)

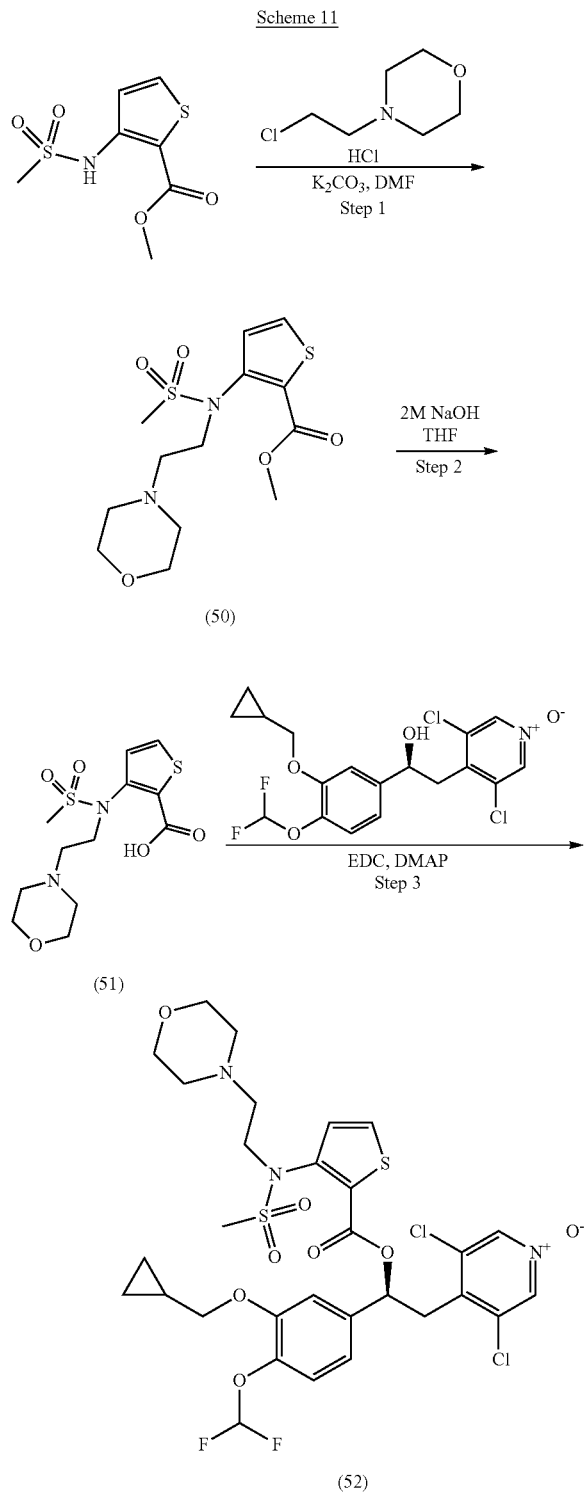

Scheme 11

Step 1. Preparation of methyl 3-(N-(2-morpholinoethyl)methylsulfonamido)thiophene-2-carboxylate (Intermediate 50)

A mixture of methyl 3-(methylsulfonamido)thiophene-2-carboxylate (prepared in an analogous manner as described in Example 8, Scheme 8, Step 1, 500 mg, 2.125 mmol), 4-(2-chloroethyl)morpholine hydrochloride (435 mg, 2.338 mmol) and potassium carbonate (646 mg, 4.68 mmol) in dry DMF (13 ml) was heated at 80° C. for 5 h and stirred at RT for 3 days. The solvent was evaporated, the residue was diluted with EtOAc and washed with $H_2O$ and brine; the organic layer was dried over $Na_2SO_4$, filtered and evaporated. The crude was purified by flash chromatography on silica gel (DCM/EtOAc=8/2 to 7/3 and then DCM/MeOH=95/5) to afford methyl 3-(N-(2-morpholinoethyl)-methylsulfonamido)thiophene-2-carboxylate (Int. 50) (655 mg, 1.880 mmol, MS/ESI$^+$ 348.9 [MH]$^+$).

Step 2. Preparation of 3-(N-(2-morpholinoethyl)-methylsulfonamido)thiophene-2-carboxylic acid (Intermediate 51)

A mixture of methyl 3-(N-(2-morpholinoethyl)methylsulfonamido)-thiophene-2-carboxylate (Intermediate 50) (348 mg, 0.999 mmol) in aqueous 2M sodium hydroxide (4.994 ml, 9.99 mmol) and THF (4.9 ml) was stirred at 60° C. for 6 hours and at RT overnight. The mixture was neutralized with 2N HCl and the solvent was removed. The crude was purified by flash chromatography on silica gel (DCM/MeOH=8/2 to 75/25) affording 3-(N-(2-morpholinoethyl)methylsulfonamido)thiophene-2-carboxylic acid (Intermediate 51) (312 mg, 0.933 mmol, MS/ESI$^+$334.9 [MH]$^+$).

Step 3. Preparation of (S)-3,5-dichloro-4-(2-(3-(cyclopropylmethoxy)-4-(difluoromethoxy)phenyl)-2-(3-(N-(2-morpholinoethyl)-methylsulfonamido)thiophene-2-carbonyloxy)ethyl)pyridine 1-oxide (Compound 52)

A mixture of 3-(N-(2-morpholinoethyl)methylsulfonamido)thiophene-2-carboxylic acid (Int. 51) (159 mg, 0.476 mmol), (S)-3,5-dichloro-4-(2-(3-(cyclopropylmethoxy)-4-(difluoromethoxy)phenyl)-2-hydroxyethyl)pyridine 1-oxide (200 mg, 0.476 mmol), EDC (274 mg, 1.428 mmol) and DMAP (87 mg, 0.714 mmol) in DCM (25 ml) was stirred at RT overnight. 0.5N HCl was added, the phases were separated, and the organic layer was washed with aqueous $NaHCO_3$ and dried over $Na_2SO_4$. The solvent was removed and the crude was purified by filtration through a SCX cartridge (DCM/MeOH=1/1, then MeOH/conc.$NH_4OH$ aq.=95/5); the basic fractions were diluted with $H_2O$ and the resulting aqueous solution was extracted with EtOAc (×3). The combined organic layers were dried over $Na_2SO_4$, filtered and evaporated. The recovered product was further purified by flash chromatography on silica gel cartridge (DCM/MeOH=99.5/0.5 to 97/3) affording (S)-3,5-dichloro-4-(2-(3-(cyclopropylmethoxy)-4-(difluoromethoxy)phenyl)-2-(3-(N-(2-morpholinoethyl)methylsulfonamido)thiophene-2-carbonyloxy)ethyl)pyridine 1-oxide (Compound 52) (50.2 mg, 0.068 mmol, MS/ESI$^+$736.21 [MH]$^+$, $[\alpha_D]$=−9.88, c=0.48, DCM).

¹H NMR (300 MHz, DMSO-d₆) δ ppm 8.40 (s, 2H), 7.89 (d, 1H), 7.24 (d, 1H), 7.19 (d, 1H), 7.19 (d, 1H), 7.05 (dd, 1H), 6.98 (t, 1H), 6.25 (dd, 1H), 3.95 (d, 2H), 3.72 (br. s., 2H), 3.59 (dd, 1H), 3.51 (br. s., 4H), 3.42 (dd, 1H), 2.95 (s, 3H), 2.31-2.46 (m, 6H), 1.12-1.33 (m, 1H), 0.51-0.66 (m, 2H), 0.23-0.45 (m, 2H)

Example 12

Synthesis of (S)-3,5-dichloro-4-(2-(3-(cyclopropylmethoxy)-4-(difluoromethoxy)phenyl)-2-(5-(N-(2-morpholinoethyl)-methylsulfonamido)thiophene-2-carbonyloxy)ethyl)pyridine 1-oxide (Compound 60)

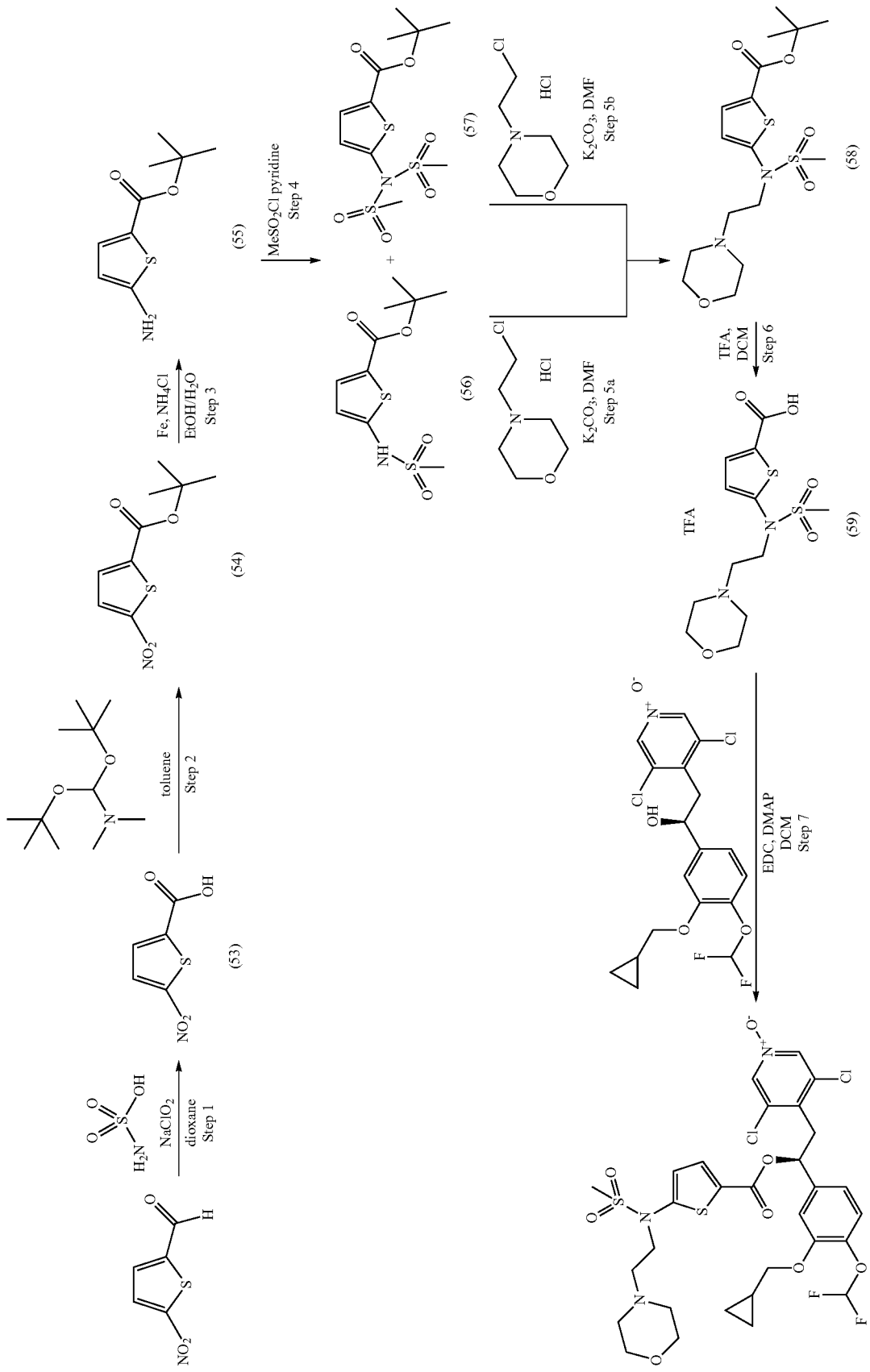
Scheme 12

Step 1. Preparation of 5-nitrothiophene-2-carboxylic acid (Intermediate 53)

A mixture of 5-nitrothiophene-2-carbaldehyde (1.685 g, 10.72 mmol) and sulfamic acid (1.249 g, 12.87 mmol) in dioxane (30 ml) was cooled to 0° C., and a solution of sodium chlorite (1.940 g, 21.44 mmol) in water (14 ml) was added drop-wise. The mixture was allowed to warm to RT and stirred for 2 hours. A second batch of 5-nitrothiophene-2-carbaldehyde (1.966 g, 12.51 mmol) was reacted under the same conditions using the molar ratios described above. The two reaction mixtures were combined and portioned between ethyl acetate and water. The organic layer was extracted twice with 5% NaHCO$_3$ and the organic phase was discarded. The basic aqueous phase was acidified with 2N HCl (pH=2) and extracted twice with ethyl acetate. The combined organic layers were washed with brine and dried over sodium sulfate; the solvent was removed affording 5-nitrothiophene-2-carboxylic acid (Int. 53) (3.6 g, 20.79 mmol, MS/ESI$^+$173.9 [MH]$^+$).

Step 2. Preparation of tert-butyl 5-nitrothiophene-2-carboxylate (Intermediate 54)

A solution of 5-nitrothiophene-2-carboxylic acid (Int. 53) (3.6 g, 20.79 mmol) in dry toluene (260 ml) was heated to reflux and 1,1-di-tert-butoxy-N,N-dimethyl-methanamine (9.97 ml, 41.6 mmol) was added drop-wise. The reaction was heated to reflux for 20 hour. The mixture was washed with a saturated solution of NaHCO3, then with brine, dried over Na$_2$SO$_4$ and evaporated to dryness to obtain tert-butyl 5-nitrothiophene-2-carboxylate (Int. 54) (2.23 g, 9.73 mmol, MS/ESI$^+$ not detectable [MH]$^+$).

Step 3. Preparation of tert-butyl 5-aminothiophene-2-carboxylate (Intermediate 55)

To a suspension of tert-butyl 5-nitrothiophene-2-carboxylate (Int. 54) (2.230 g, 9.73 mmol) in a mixture of EtOH (60 ml) and water (30 ml), iron powder (3.26 g, 58.4 mmol) and ammonium chloride (0.364 g, 6.81 mmol) were added. The reaction was stirred at 80° C. for 3 hours and then at RT overnight. The mixture was filtered through a celite pad and the filtrate was evaporated to dryness. The crude was then dissolved in EtOAc and washed with brine; the organic phase was dried over sodium sulfate and the solvent evaporated under vacuum. The residue was purified by filtration through a silica gel cartridge (petroleum ether/EtOAc=9/1 to 6/4) to yield tert-butyl 5-aminothiophene-2-carboxylate (Int. 55) (1.481 g, 7.43 mmol, MS/ESI$^+$200.0 [MH]$^+$).

Step 4. Preparation of tert-butyl 5-(methylsulfonamido)thiophene-2-carboxylate (Intermediate 56) and tert-butyl 5-(N-(methylsulfonyl)-methylsulfonamido)thiophene-2-carboxylate (Intermediate 57)

To a solution of tert-butyl 5-aminothiophene-2-carboxylate (Int. 55) (1.481 g, 7.43 mmol) in pyridine (50 ml) cooled to 0° C., methanesulfonyl chloride (0.695 ml, 8.92 mmol) was added drop-wise. The reaction was warmed to RT and stirred for 3 days. The solvent was removed under vacuum, and the residue was portioned between EtOAc and 1N HCl; the organic phase was washed with brine, dried over sodium sulfate, filtered and evaporated to dryness. The crude was purified by flash chromatography on silica gel cartridge (petroleum ether/EtOAc=8/2) to afford tert-butyl 5-(methylsulfonamido)-thiophene-2-carboxylate (Int. 56) (773 mg, 2.79 mmol, MS/ESI$^+$299.9 [MNa]$^+$) and tert-butyl 5-(N-(methylsulfonyl)-methylsulfonamido)thiophene-2-carboxylate (Int. 57) (420 mg, 1.182 mmol, MS/ESI$^+$ not detectable [MH]$^+$).

Step 5a-b. Preparation of tert-butyl 5-(N-(2-morpholinoethyl)-methylsulfonamido)-thiophene-2-carboxylate (Intermediate 58)

A mixture of tert-butyl 5-(methylsulfonamido)thiophene-2-carboxylate (int. 56) (773 mg, 2.79 mmol), 4-(2-chloroethyl)morpholine hydrochloride (778 mg, 4.18 mmol) and K$_2$CO$_3$ (963 mg, 6.97 mmol) in DMF (30 ml) was heated to 80° C. for 6 hours. In parallel a mixture of tert-butyl 5-(N-(methylsulfonyl)methylsulfonamido)thiophene-2-carboxylate (Int. 57) (420 mg, 1.182 mmol), 4-(2-chloroethyl)morpholine hydrochloride (330 mg, 1.772 mmol) and K$_2$CO$_3$ (408 mg, 2.95 mmol) in DMF (15 ml) was heated to 80° C. for 4 hours, stirred at RT overnight and heated to 80° C. for additional 2 hours. The two reaction mixtures were combined and partitioned between EtOAc and water. The aqueous phase was extracted with EtOAc and the combined organic layers were washed several times with brine, dried over sodium sulfate, filtered and concentrated to dryness. The residue was purified by flash chromatography on silica gel (petroleum ether/EtOAc=6/4 to EtOAc 100%) to afford tert-butyl 5-(N-(2-morpholinoethyl)methylsulfonamido)-thiophene-2-carboxylate (Int. 58) (1.3 g, 3.33 mmol, MS/ESI$^+$391.0 [MH]$^+$).

Step 6. Preparation of 5-(N-(2-morpholinoethyl)methylsulfonamido)-thiophene-2-carboxylic acid 2,2,2-trifluoroacetic acid salt (Intermediate 59)

To a solution of tert-butyl 5-(N-(2-morpholinoethyl)-methylsulfonamido)-thiophene-2-carboxylate (Int. 58) (1.3 g, 3.33 mmol) in DCM (50 ml), TFA (2.56 ml, 33.3 mmol) was added drop-wise at 0° C. and then the brown solution was stirred at RT overnight. Additional TFA (7.69 ml, 99.9 mmol) was added in two portions over 4 hours, cooling to 0° C. and stirring at RT. The volatiles were removed under vacuum to afford 5-(N-(2-morpholinoethyl)methylsulfonamido)thiophene-2-carboxylic acid 2,2,2-trifluoroacetic acid salt (Int. 59) (1.436 g, 3.21 mmol, MS/ESI$^+$335.0 [MH]$^+$).

Step 7. Preparation of (S)-3,5-dichloro-4-(2-(3-(cyclopropylmethoxy)-4-(difluoromethoxy)phenyl)-2-(5-(N-(2-morpholinoethyl)-methylsulfonamido)thiophene-2-carbonyloxy)ethyl)pyridine 1-oxide (Compound 60)

(S)-3,5-dichloro-4-(2-(3-(cyclopropylmethoxy)-4-(difluoromethoxy)-phenyl)-2-hydroxyethyl)pyridine 1-oxide (1.387 g, 3.3 mmol), 5-(N-(2-morpholinoethyl)-methylsulfonamido)thiophene-2-carboxylic acid 2,2,2-trifluoroacetic acid salt (Int. 59) (1.436 g, 3.21 mmol), EDC (1.914 g, 9.99 mmol) and DMAP (0.813 g, 6.66 mmol) were dissolved in DCM (100 ml), and the resulting mixture was stirred at RT for 7 hours. A second portion of EDC (1.914 g, 9.99 mmol) and DMAP (0.813 g, 6.66 mmol) was added, and the mixture stirred at RT for 3 days. A further addition of EDC (0.447 g, 2.330 mmol) and DMAP (0.285 g, 2.330 mmol) was performed and the mixture was heated at 40° C. for 5 hrs; after a new addition of EDC (0.319 g, 1.664 mmol) and DMAP (0.203 g, 1.664 mmol), the mixture was stirred at 40° C. overnight. The mixture was diluted with DCM (100 ml)

and washed with 0.5N HCl (3×80 ml), with 5% NaHCO$_3$ (80 ml) and finally with brine (80 ml); the organic phase was dried over sodium sulfate, filtered and concentrated under vacuum. The crude was purified by chromatography on silica gel cartridge (DCM/EtOAc 1/1, then washing the column with DCM, then DCM/MeOH=99/2) to afford an off white solid (1.6 g) that was triturated with MeOH. The obtained solid was dissolved in a 1/1 mixture of DCM/MeOH, and the solvents were removed under vacuum; this same operation was repeated twice. The residue was dried to afford (S)-3,5-dichloro-4-(2-(3-(cyclopropylmethoxy)-4-(difluoromethoxy)phenyl)-2-(5-(N-(2-morpholinoethyl)methylsulfonamido)thiophene-2-carbonyloxy)ethyl)pyridine 1-oxide (Compound 60) (1.230 g, 1.670 mmol, MS/ESI$^+$736.05 [MH]$^+$, [α$_D$]=−38.54, c=1, MeOH).

$^1$H NMR (300 MHz, DMSO-d$_6$) δ ppm 8.55 (s, 2H), 7.71 (d, 1H), 7.21 (d, 1H), 7.19 (d, 1H), 7.11 (d, 1H), 7.05 (dd, 1H), 7.07 (t, 1H), 6.13 (dd, 1H), 3.93 (d, 2H), 3.81 (t, 2H), 3.58 (dd, 1H), 3.48-3.54 (m, 4H), 3.32 (dd, 1H), 3.19 (s, 3H), 2.47 (t, 2H), 2.34-2.41 (m, 4H), 1.04-1.34 (m, 1H), 0.46-0.64 (m, 2H), 0.25-0.45 (m, 2H).

The compounds listed in Table 5 were prepared according to analogous synthetic procedures to those described above and depicted in Scheme 12, Step 1-7 (Step 5a), by reacting the appropriate precursors (commercially available or synthesized by a person skilled in the art) with suitable reagents, and where purification step has been performed as indicated in Table 5.

TABLE 5

| Structure | Compound | NMR characterization | MS/ESI$^+$ [MH]$^+$ [α$_D$] | Starting Material [and conditions, if different] | Purification method |
|---|---|---|---|---|---|
| (structure) | 61 | $^1$H NMR (300 MHz, DMSO-d$_6$) δ ppm 8.55 (s, 2 H), 7.71 (d, 1 H), 7.21 (d, 1 H), 7.19 (d, 1 H), 7.09 (d, 1 H), 7.05 (dd, 1 H), 7.07 (t, 1 H), 6.13 (dd, 1 H), 3.93 (d, 2 H), 3.79 (t, 2 H), 3.58 (dd, 1 H), 3.32 (dd, 1 H), 3.17 (s, 3 H), 2.59 (t, 2 H), 2.34-2.48 (m, 4 H), 1.55-1.75 (m, 4 H), 1.08-1.31 (m, 1 H), 0.47-0.68 (m, 2 H), 0.26-0.46 (m, 2 H) | 720.13 [α$_D$] = −35.10 (c = 0.510, DCM) | (structure) Used for alkylation of Intermediate 56 (reaction not performed on intermediate (57)) Step 6: DCM, TFA (20 eq), 0° C. to RT overnight Step 7: DCM, RT, 3 days | Flash chromatography on silica gel (DCM/MeOH = 98/2 to 95/5) |
| (structure) | 62 | $^1$H NMR (300 MHz, DMSO-d$_6$) δ ppm 8.52 (s, 2 H), 8.46-8.52 (m, 2 H), 7.72 (dt, 1 H), 7.64 (d, 1 H), 7.38 (ddd, 1 H), 7.19 (d, 1 H), 7.15 (d, 1 H), 7.09 (d, 1 H), 7.01 (dd, 1 H), 7.05 (t, 1 H), 6.08 (dd, 1 H), 4.97 (s, 2 H), 3.91 (d, 2 H), 3.54 (dd, 1 H), 3.30-3.35 (m, 1 H), 3.26 (s, 3H), 1.05-1.35 (m, 1 H), 0.45-0.64 (m, 2 H), 0.28-0.43 (m, 2 H) | 714.01 [α$_D$] = −38.20 (c = 0.500, DCM) | (structure) Used for alkylation of Intermediate 56 (reaction not performed on intermediate (57)) Step 6: DCM, TFA (20 eq), 0° C. to RT overnight Step 7: DCM, RT, 3 days | Flash chromatography on silica gel (DCM/MeOH = 98/2 to 95/5) |
| (structure) | 63 | $^1$H NMR (300 MHz, DMSO-d$_6$) δ ppm 8.54 (s, 2 H), 7.69 (d, 1 H), 7.21 (d, 1 H), 7.19 (d, 1 H), 7.01-7.09 (m, 2 H), 7.07 (t, 1 H), 6.13 (dd, 1 H), 3.93 (d, 2 H), 3.87 (t, 2 H), 3.58 (dd, 1 H), 3.48-3.53 (m, 4 H), 3.30-3.39 (m, 3 H), 2.47 (t, 2 H), 2.33-2.40 (m, 4 H), 1.11-1.29 (m, 1 H), 0.91-1.11 (m, 1 H), 0.48-0.65 (m, 4 H), 0.27-0.44 (m, 4 H) | 776.09 [α$_D$] = −32.59 (c = 0.54; DCM) | (structure) Reactant of Step 4 (0° C. to r.t. 3 h, only mono-sulfonylated derivative was isolated) (structure) Reactant of Step 5a (80° C., 2 h) Step 6: DCM, TFA (20 eq), 0° C. to RT overnight Step 7: DCM, RT, 3 days | Flash chromatography on silica gel (DCM/MeOH = 98/2) |

TABLE 5-continued

| Structure | Compound | NMR characterization | MS/ESI+ [MH]+ [α_D] | Starting Material [and conditions, if different] | Purification method |
|---|---|---|---|---|---|
| (structure shown) | 64 | ¹H NMR (300 MHz, DMSO-d₆) δ ppm 8.54 (s, 2 H), 7.69 (d, 1 H), 7.21 (d, 1 H), 7.19 (d, 1 H), 7.00-7.06 (m, 2 H), 7.07 (t, 1 H), 6.12 (dd, 1 H), 3.93 (d, 2 H), 3.86 (t, 2 H), 3.58 (dd, 1 H), 3.31 (dd, 1 H), 3.31 (d, 2 H), 2.61 (t, 2 H), 2.38-2.48 (m, 4 H), 1.49-1.75 (m, 4 H), 1.11-1.33 (m, 1 H), 0.89-1.11 (m, 1 H), 0.44-0.68 (m, 4 H), 0.18-0.44 (m, 4 H) | 760.08 [α_D] = −28.46 (c = 0.52, DCM) | Reactant of Step 4 (0° C. to r.t. 3 h, only mono-sulfonylated derivative was isolated) Reactant of Step 5a (80° C., 2.5 h) Step 6: DCM, TFA (20 eq), 0° C. to RT overnight Step 7: DCM, RT, 3 days | Flash chromatography on silica gel (DCM/MeOH = 98/2) |

Example 13

Synthesis of (S)-3,5-dichloro-4-(2-(3-(cyclopropyl-methoxy)-4-(difluoromethoxy)phenyl)-2-(4-methoxy-5-(N-(2-morpholinoethyl)-methylsulfonamido)thiophene-2-carbonyloxy)ethyl)pyridine 1-oxide 2,2,2-trifluoroacetate (Compound 72)

Scheme 13

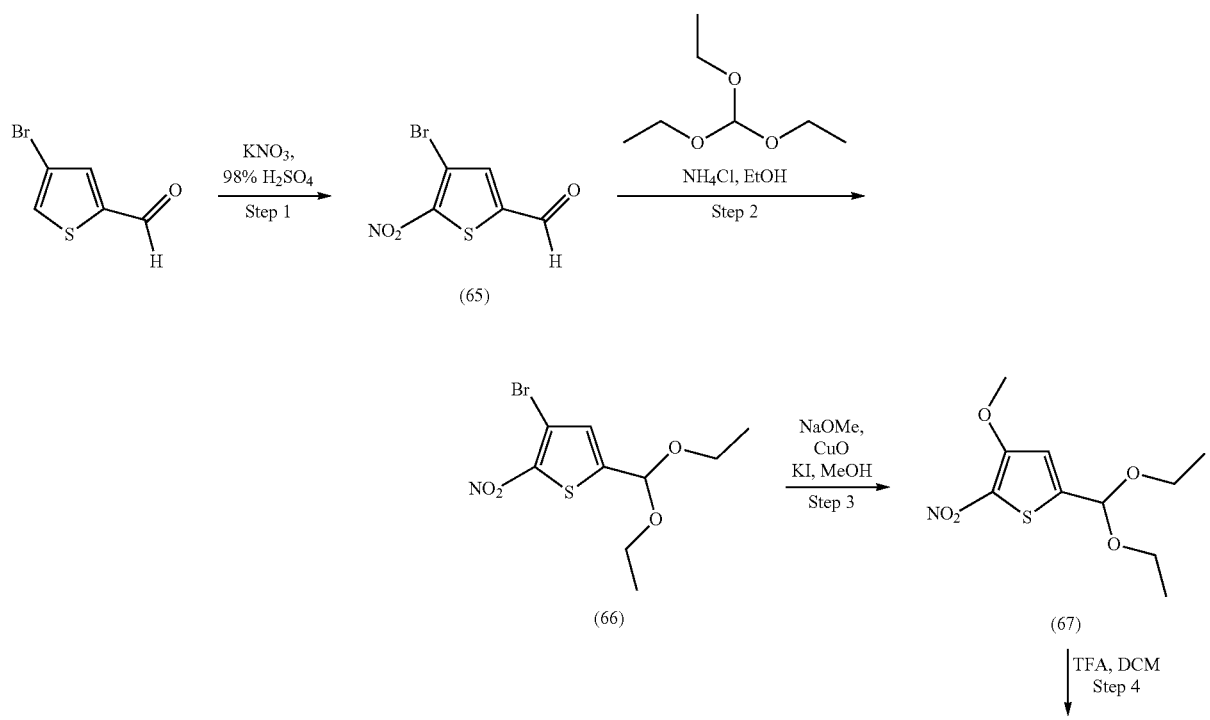

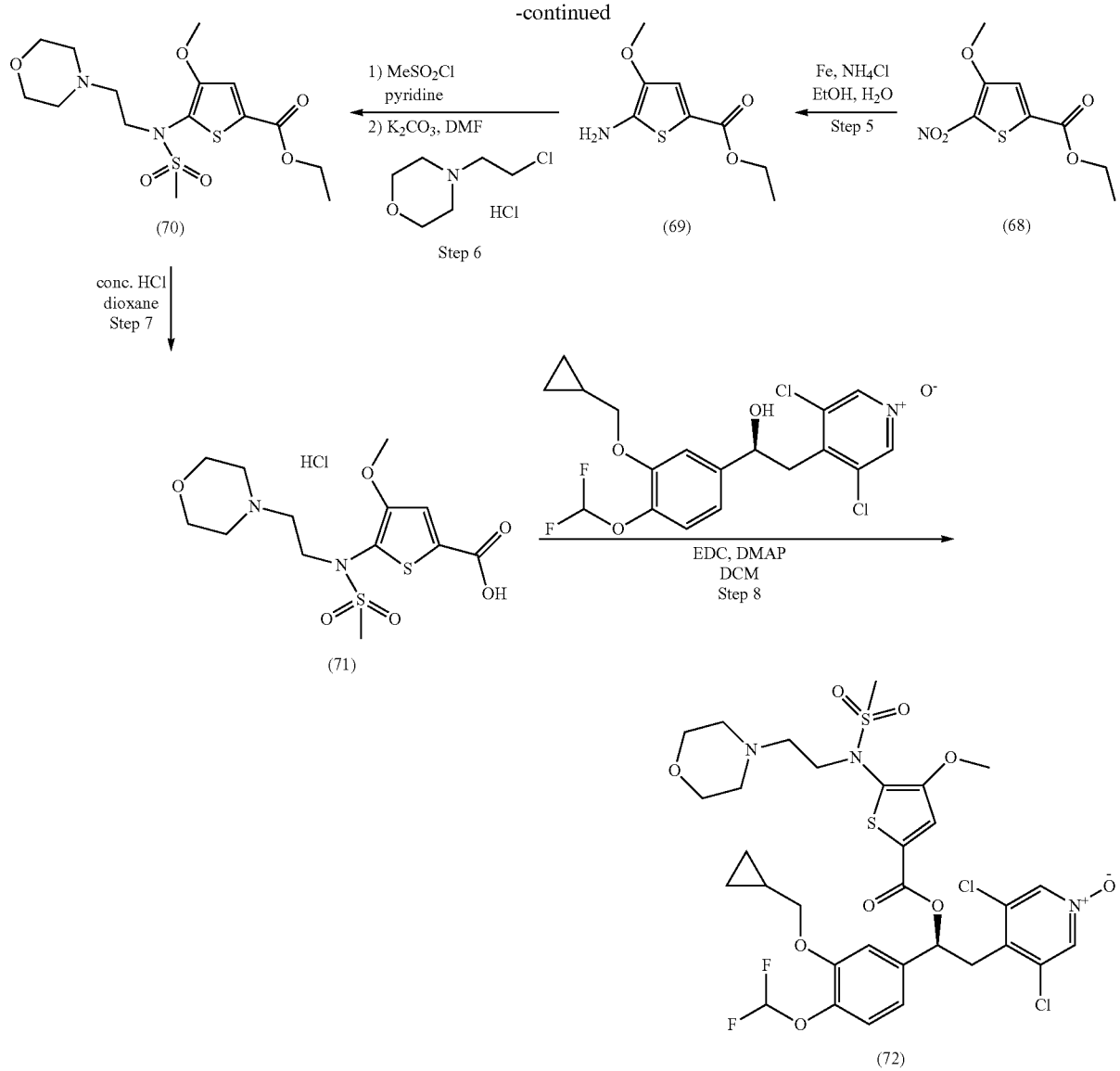

Step 1. Preparation of 4-bromo-5-nitrothiophene-2-carbaldehyde (Intermediate 65)

A solution of KNO₃ (3.38 g, 33.4 mmol) in 96% aqueous H₂SO₄ (30 ml) was added to a solution of 4-bromothiophene-2-carbaldehyde (5.8 g, 30.4 mmol) in 96% aqueous H₂SO₄ (60 ml) over 45 minutes, maintaining the temperature below 4° C. The resulting mixture was stirred at 0° C. for 2 hrs and then at RT overnight. The reaction was poured into ice (300 ml) and the resulting precipitate was filtered and washed with water and hexane to afford 4-bromo-5-nitrothiophene-2-carbaldehyde (Int. 65) (6.987 g, 29.6 mmol).

Step 2. Preparation of 3-bromo-5-(diethoxymethyl)-2-nitrothiophene (Intermediate 66)

To a solution of 4-bromo-5-nitrothiophene-2-carbaldehyde (Int. 65) (6.981 g, 29.6 mmol) in EtOH (50 ml), ammonium chloride (0.475 g, 8.87 mmol) and triethyl orthoformate (7.39 ml, 44.4 mmol) were added, and the resulting solution was stirred at 60° C. for 14 hours. Additional triethyl orthoformate (7.39 ml, 44.4 mmol) was added, and the mixture was vigorously refluxed for further 2 days. The solvent was evaporated under vacuum and the crude was partitioned between water and EtOAc. The organic phase was washed with brine, dried over sodium sulfate, filtered and evaporated. The crude was purified by chromatography on silica gel cartridge (petroleum ether/EtOAc=9/1) to afford 3-bromo-5-(diethoxymethyl)-2-nitrothiophene (Int. 66) (7.456 g, 24.04 mmol).

Step 3. Preparation of 5-(diethoxymethyl)-3-methoxy-2-nitrothiophene (Intermediate 67)

To a solution of 3-bromo-5-(diethoxymethyl)-2-nitrothiophene (Int. 66) (1 g, 3.22 mmol) in MeOH (10 ml) copper(II)

oxide (0.051 g, 0.645 mmol), KI (10.7 mg, 0.064 mmol) and sodium methanolate (0.662 g, 12.25 mmol) were added, and the mixture was heated under MW irradiation at 120° C. for 2 hours. The reaction mixture was filtered through a celite pad, the filtrate was concentrated under vacuum and then partitioned between 0.5N HCl and EtOAc. The organic phase was dried over sodium sulfate, filtered and evaporated to give 5-(diethoxymethyl)-3-methoxy-2-nitrothiophene (Int. 67) (680 mg, 2.60 mmol, MS/ESI$^+$261.0 [MH]$^+$). This crude was used without any additional purification.

Step 4. Preparation of ethyl 4-methoxy-5-nitrothiophene-2-carboxylate (Intermediate 68)

To a solution of 5-(diethoxymethyl)-3-methoxy-2-nitrothiophene (Int. 67) (680 mg, 2.60 mmol) in DCM (15 ml) cooled to 0° C., TFA (5 ml, 64.9 mmol) was added, and the resulting mixture was stirred at RT for 2 hours and then concentrated to dryness. The crude was purified by silica gel flash chromatography (petroleum ether/EtOAc=99/1 to petroleum ether/EtOAc=9/1) to afford ethyl 4-methoxy-5-nitrothiophene-2-carboxylate (Int. 68) (300 mg, 1.297 mmol, containing about 30% of the corresponding methyl ester, MS/ESI$^+$231.9 [MH]$^+$). This intermediate was used as such in the following step considering it was a single product.

Step 5. Preparation of ethyl 5-amino-4-methoxythiophene-2-carboxylate (Intermediate 69)

A mixture of ethyl 4-methoxy-5-nitrothiophene-2-carboxylate (Int. 68) (300 mg, 1.297 mmol) (prepared as described in Step 4 hereabove reported), and ammonium chloride (139 mg, 2.59 mmol) in EtOH/water=2/1 (18 ml) was heated at 50° C. until complete dissolution. Iron powder (435 mg, 7.78 mmol) was added, and the reaction was heated at 80° C. for 2 hours. The mixture was filtered and the filtrate was concentrated under vacuum; the residue was portioned between brine and EtOAc and the organic phase was dried over sodium sulfate. The solvent was removed to afford ethyl 5-amino-4-methoxythiophene-2-carboxylate (Int. 69) in a mixture with approximately 30% of corresponding methyl ester (261 mg, 1.297 mmol, MS/ESI$^+$201.9 [MH]$^+$). This intermediate was used as such in the following step.

Step 6. Preparation of ethyl 4-methoxy-5-(N-(2-morpholinoethyl)methylsulfonamido)-thiophene-2-carboxylate (Intermediate 70)

To a solution of ethyl 5-amino-4-methoxythiophene-2-carboxylate (Int. 69) (261 mg, 1.297 mmol) (prepared as described in Step 5 hereabove reported) in pyridine (10 ml) cooled to 0° C., methanesulfonyl chloride (0.131 ml, 1.686 mmol) was added, and the reaction was allowed to warm to RT and stirred overnight. The solvent was removed under vacuum and the residue was portioned between EtOAc and 10% HCl; the organic phase was washed with brine and dried over sodium sulfate. The solvent was removed under vacuum and the residue was dissolved in dry DMF (10 ml); $K_2CO_3$ (448 mg, 3.24 mmol) and 4-(2-chloroethyl)morpholine hydrochloride (362 mg, 1.946 mmol) were added in one portion, and the resulting mixture was heated to 80° C. and stirred at this temperature for 3 hours. The solvent was removed under vacuum, and the residue was dissolved in EtOAc and washed with brine. The organic phase was dried over sodium sulfate, filtered evaporated. The residue was purified by filtration on silica gel cartridge (DCM/EtOAc=8/2 to EtOAc) to afford ethyl 4-methoxy-5-(N-(2-morpholinoethyl)-methylsulfonamido)thiophene-2-carboxylate (Int. 70) in a mixture with approximately 30% of corresponding methyl ester (375 mg, 0.955 mmol, MS/ESI$^+$ 392.8 [MH]$^+$). This intermediate was used as such in the following step considering it was a single product.

Step 7: Preparation of 4-methoxy-5-(N-(2-morpholinoethyl)-methylsulfonamido)-thiophene-2-carboxylic acid hydrochloride (Intermediate 71)

To a solution of ethyl 4-methoxy-5-(N-(2-morpholinoethyl)-methylsulfonamido)-thiophene-2-carboxylate (Int. 70, 375 mg, 0.955 mmol) (prepared as described in Step 6 hereabove reported) in dioxane (8 ml), aqueous 37% HCl (3 ml) was added drop wise, and the resulting mixture was heated under MW irradiation at 100° C. for 3.5 hours. The volatiles were removed under vacuum to afford 4-methoxy-5-(N-(2-morpholinoethyl)-methylsulfonamido)thiophene-2-carboxylic acid hydrochloride (Int. 71) (383 mg, 0.955 mmol, MS/ESI$^+$364.9 [MH]$^+$).

Step 8. Preparation of (S)-3,5-dichloro-4-(2-(3-(cyclopropylmethoxy)-4-(difluoromethoxy)phenyl)-2-(4-methoxy-5-(N-(2-morpholinoethyl)-methylsulfonamido)-thiophene-2-carbonyloxy)ethyl)pyridine 1-oxide 2,2,2-trifluoroacetate (Compound 72)

(S)-3,5-dichloro-4-(2-(3-(cyclopropylmethoxy)-4-(difluoromethoxy)-phenyl)-2-hydroxyethyl)pyridine 1-oxide (401 mg, 0.955 mmol), 4-methoxy-5-(N-(2-morpholinoethyl)methylsulfonamido)thiophene-2-carboxylic acid hydrochloride (Int. 71) (383 mg, 0.955 mmol), EDC (549 mg, 2.87 mmol) and DMAP (233 mg, 1.911 mmol) were dissolved in DCM (30 ml), and the solution was stirred at RT for 4 days. The mixture was diluted with DCM and washed with 0.5N HCl, sat $Na_2CO_3$ and finally with brine. The organic phase was dried over sodium sulfate and the solvent removed under vacuum. The crude was purified by flash chromatography on silica gel (DCM/MeOH/conc.$NH_4OH$=98/2/0.2) and then by a further flash chromatography on silica gel (DCM/MeOH/conc.$NH_4OH$=99/1/0.1). An additional purification by preparative HPLC-Method 1 was required to afford (S)-3,5-dichloro-4-(2-(3-(cyclopropylmethoxy)-4-(difluoromethoxy)phenyl)-2-(4-methoxy-5-(N-(2-morpholinoethyl)methylsulfonamido) thiophene-2-carbonyloxy)ethyl)pyridine 1-oxide 2,2,2-trifluoroacetate (Compound 72) (150 mg, 0.170 mmol, MS/ESI$^+$766.05 [MH]$^+$, [$\alpha_D$]=−27.72, c=0.5, DCM).

$^1$H NMR (300 MHz, DMSO-d$_6$) δ ppm 9.65 (s, 1H), 8.58 (s, 2H), 7.76 (s, 1H), 7.15-7.28 (m, 2H), 6.94-7.15 (m, 1H), 7.07 (t, 1H), 6.14 (dd, 1H), 3.92 (s, 3H), 3.74-4.06 (m, 10H), 3.60 (dd, 1H), 3.35 (dd, 1H), 3.14 (s, 3H), 2.99-3.28 (m, 4H), 1.00-1.33 (m, 1H), 0.46-0.73 (m, 2H), 0.32-0.39 (m, 2H).

Example 14
Synthesis of (S)-3,5-dichloro-4-(2-(3-(cyclopropyl-methoxy)-4-(difluoromethoxy)phenyl)-2-(5-(N-(4-(dimethylcarbamoyl)phenyl)-sulfamoyl)thiophene-2-carbonyloxy)ethyl)pyridine 1-oxide (Compound 77)
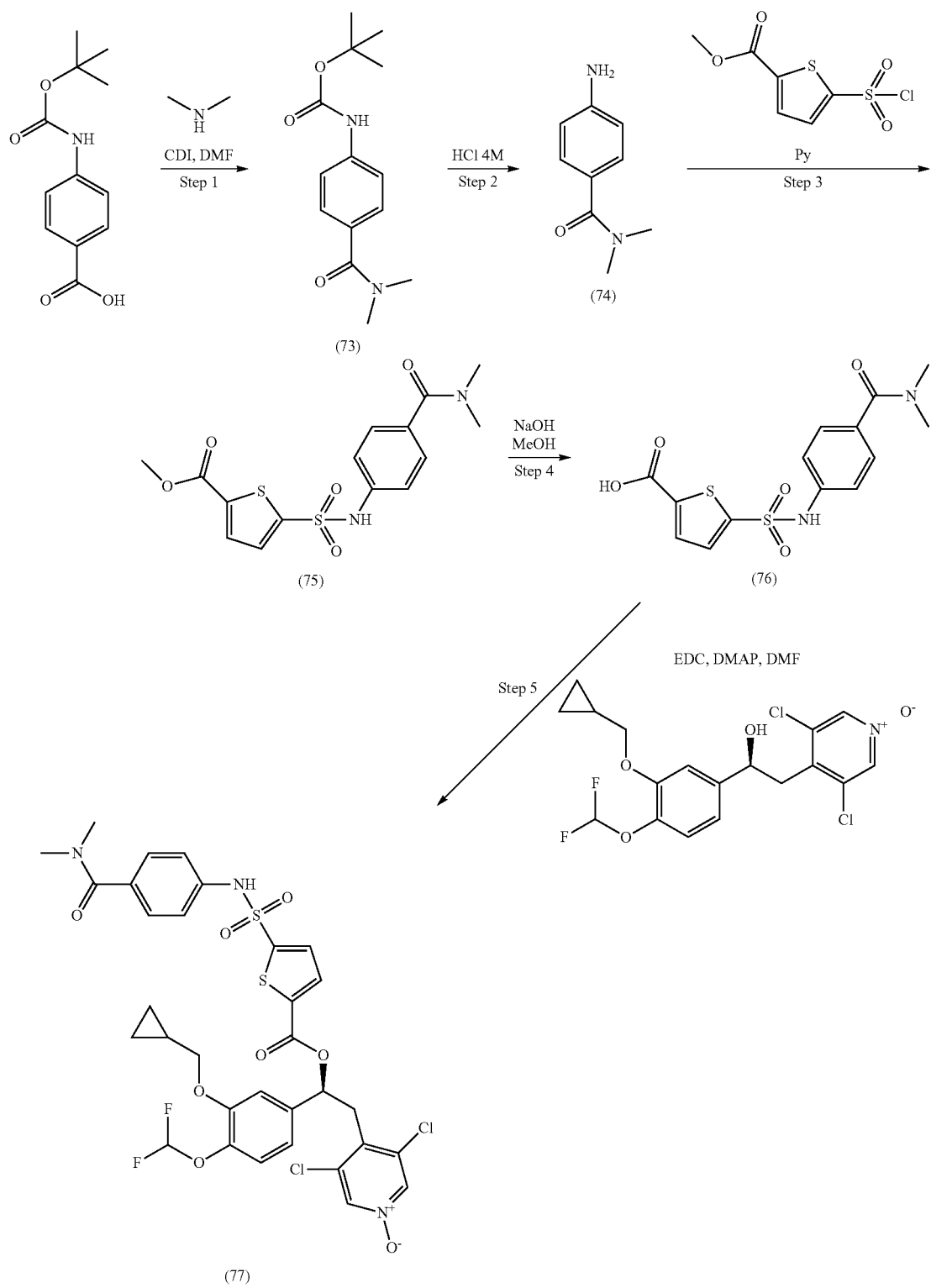

Step 1. Synthesis of tert-butyl 4-(dimethylcarbamoyl)-phenylcarbamate (Intermediate 73)

To a solution of 4-(tert-butoxycarbonylamino)benzoic acid (1 g, 4.21 mmol) in DMF (10 ml) CDI (1.025 g, 6.32 mmol) was added. The mixture was stirred at RT for 2 hours. Dimethylamine 2M in THF (3.16 ml, 6.32 mmol) was added, and the mixture stirred at RT for 3 hours. The mixture was poured onto water and extracted with AcOEt (2×). Organic phase was dried over $Na_2SO_4$ and evaporated under vacuum to give g 1.25 of Int. 73 which crystallizes on standing.

Step 2. Synthesis of 4-amino-N,N-dimethylbenzamide (Intermediate 74)

To a solution of tert-butyl 4-(dimethylcarbamoyl)phenylcarbamate (Int. 73) (1.11 g, 4.21 mmol) in AcOEt (20 ml), HCl 4M in AcOEt (18 ml, 76 mmol) was added, and the mixture stirred for 5 hours at RT. The pH was adjusted at 6/7 by adding $NaHCO_3$ sat. sol. and aqueous phase was extracted with AcOEt (×3). Organic phase was dried over $Na_2SO_4$ and evaporated under reduced pressure to give mg 615 of the title product (Int. 74).

Step 3. Synthesis of methyl 5-(N-(4-(dimethylcarbamoyl)phenyl)sulfamoyl)thiophene-2-carboxylate (Intermediate 75)

To a solution of 4-amino-N,N-dimethylbenzamide (Int. 74) (57 g, 347 mmol) in pyridine (570 µL, 7.06 mmol) kept at 0 degrees in an ice/water bath, methyl 5-(chlorosulfonyl)thiophene-2-carboxylate (100 g, 417 mmol) was added, and the mixture stirred at 0 degrees for 3 hours. The reaction mixture was diluted with HCl 1N and extracted with AcOEt (×2). The organic phase was dried over $Na_2SO_4$ and concentrated under vacuum to give 100 mg of 5-(N-(4-(dimethylcarbamoyl)phenyl)sulfamoyl)-thiophene-2-carboxylate (Int. 75).

Step 4. Synthesis of 5-(N-(4-(dimethylcarbamoyl)phenyl)-sulfamoyl)thiophene-2-carboxylic acid (Intermediate 76)

To a solution of methyl 5-(N-(4-(dimethylcarbamoyl)phenyl)-sulfamoyl)-thiophene-2-carboxylate (Int. 75) (100 mg, 0.271 mmol) in methanol (10 ml), sodium hydroxide 1M (1 ml) was added, and the mixture stirred at RT for 4 days with monitoring the progress of reaction and adding further amounts of NaOH 1M until completion. MeOH was evaporated under reduced pressure and the crude taken up with HCl 1N and AcOEt. The organic phase was dried over $Na_2SO_4$ and concentrated under vacuum to give 54 mg of 5-(N-(4-(dimethylcarbamoyl)phenyl)sulfamoyl)thiophene-2-carboxylic acid (Int. 76).

Step 5. Synthesis of (S)-3,5-dichloro-4-(2-(3-(cyclopropylmethoxy)-4-(difluoromethoxy)phenyl)-2-(5-(N-(4-(dimethylcarbamoyl)phenyl)-sulfamoyl)thiophene-2-carbonyloxy)ethyl)pyridine 1-oxide (Compound 77)

5-(N-(4-(dimethylcarbamoyl)phenyl)sulfamoyl)thiophene-2-carboxylic acid (Int. 76) (54 mg, 0.152 mmol), DMAP (6.20 mg, 0.051 mmol), and EDC (38.9 mg, 0.203 mmol) were dissolved in DMF. (S)-3,5-dichloro-4-(2-(3-(cyclopropylmethoxy)-4-(difluoromethoxy)phenyl)-2-hydroxyethyl)pyridine 1-oxide (42.7 mg, 0.102 mmol) was added. The reaction was stirred at RT for 4 hours. The reaction mixture was diluted with water and extracted with AcOEt. The organic phase was dried over $Na_2SO_4$ and concentrated under vacuum to give a crude product which was purified by preparative HPLC-Method 2 to give 10 mg of the desired product (Compound 77).

The compound reported in Table 6 was prepared according to an analogous procedure as that described in Scheme 14 starting from commercial suitable reagents.

TABLE 6

| Structure | Compound | NMR characterization | MS/ESI+ [MH]+ [$α_D$] | Starting Material [and conditions, if different] | Purification method |
|---|---|---|---|---|---|
| (structure depicted) | 78 | 1H NMR (400 MHz, acetone) δ ppm $^1$H NMR (400 MHz, DMSO-$d_6$) δ ppm 10.71-10.90 (bs, 1 H), 8.55 (s, 2 H), 7.72-7.82 (m, 1 H), 7.53-7.61 (m, 1 H), 7.32-7.46 (m, 1 H), 7.11-7.29 (m, 4 H), 7.06-7.11 (m, 2H), 7.00-7.05 (m, 1 H), 6.03-6.14 (m, 1 H), 3.91 (d, J = 7.06 Hz, 2 H), 3.49-3.63 (m, 1 H), 3.20-3.30 (m, 1 H), 2.93 (s, 3 H), 2.73 (s, 3 H), 1.14-1.29 (m, 1 H), 0.50-0.62 (m, 2 H), 0.29-0.39 (m, 2 H). | 756.1 | (structure depicted) | preparative HPLC-Method 2 |

Example 15

Synthesis of (S)-3,5-dichloro-4-(2-(3-(cyclopropylmethoxy)-4-(difluoromethoxy)phenyl)-2-(3-(3-(dimethylcarbamoyl)-phenylsulfonamido)thiophene-2-carbonyloxy)ethyl)pyridine 1-oxide (Compound 81)

added, and the reaction was stirred at RT for 3 hrs to achieve completion. The reaction mixture was diluted with HCl 1N and extracted with AcOEt. The organic phase was washed with HCl 1N and brine, dried over Na2SO4 and concentrated under vacuum to give methyl 3-(3-(dimethylcarbamoyl)phenylsulfonamido)thiophene-2-carboxylate (Int. 79, 200 mg, 0.543 mmol).

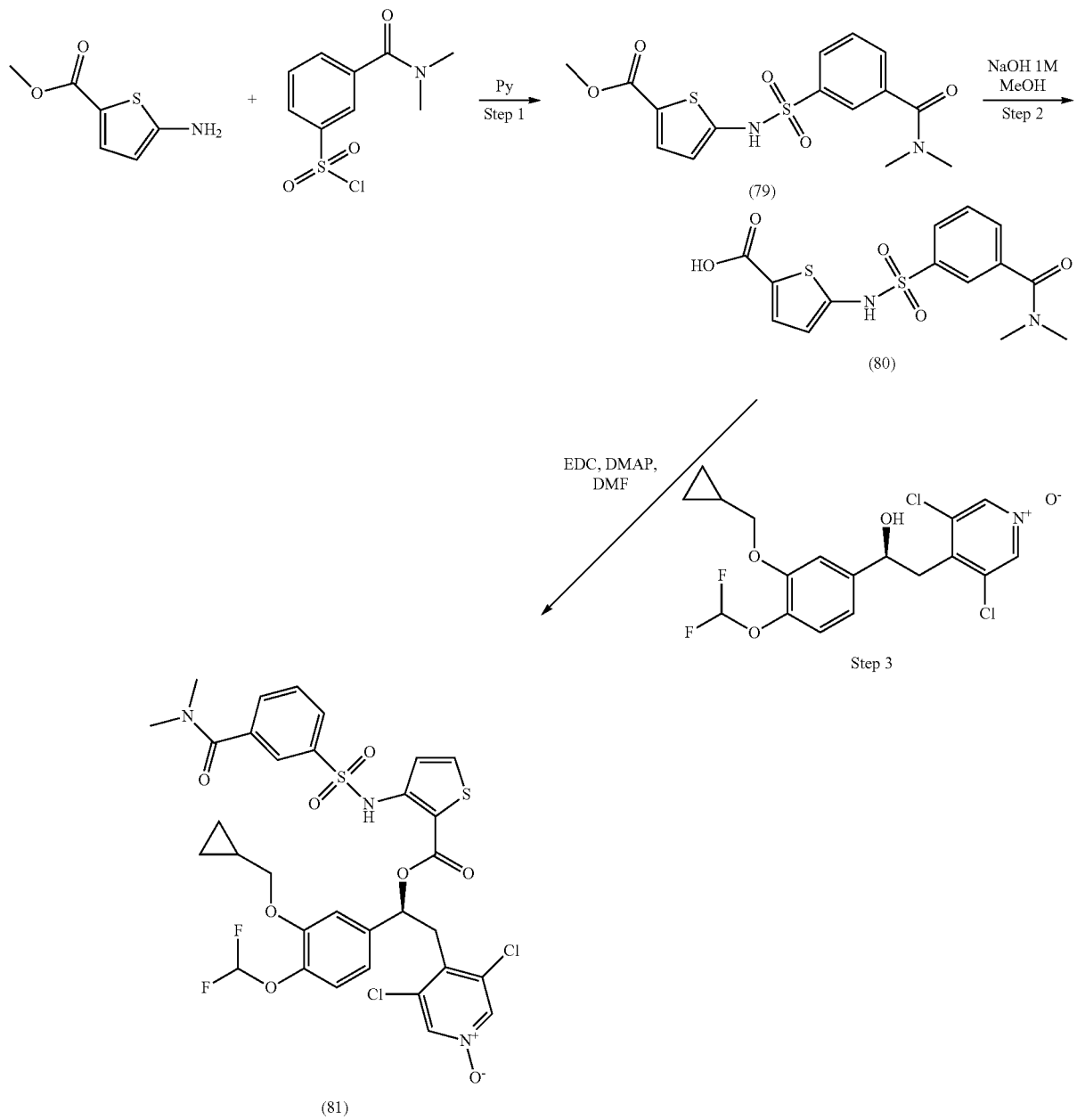

Scheme 15

Step 1. Synthesis of methyl 3-(3-(dimethylcarbamoyl)-phenylsulfonamido)thiophene-2-carboxylate (Intermediate 79)

Methyl 3-aminothiophene-2-carboxylate (93 mg, 0.592 mmol) was dissolved in Py (1.5 ml). 3-(dimethylcarbamoyl)benzene-1-sulfonyl chloride (220 mg, 0.887 mmol) was

Step 2. Synthesis of 3-(3-(dimethylcarbamoyl)-phenylsulfonamido)thiophene-2-carboxylic acid (Intermediate 80)

Methyl 3-(3-(dimethylcarbamoyl)phenylsulfonamido) thiophene-2-carboxylate (Int. 79, 200 mg, 0.543 mmol) was dissolved in MeOH (4 ml, 99 mmol). NaOH 1M (2 ml) was added, and the reaction was stirred at RT for 8 hours to achieve completion. The reaction mixture was diluted with HCl 1N and extracted with AcOEt. The organic phase was washed with HCl 1N and brine, dried over Na2SO4 and concentrated under vacuum to give 3-(3-(dimethylcarbamoyl)phenylsulfonamido)thiophene-2-carboxylic acid (Int. 80, 150 mg, 0.423 mmol).

Step 3. Synthesis of (S)-3,5-dichloro-4-(2-(3-(cyclopropylmethoxy)-4-(difluoromethoxy)phenyl)-2-(3-(3-(dimethylcarbamoyl)-phenylsulfonamido)thiophene-2-carbonyloxy)ethyl)pyridine 1-oxide (Compound 81)

(S)-3,5-Dichloro-4-(2-(3-(cyclopropylmethoxy)-4-(difluoromethoxy)-phenyl)-2-hydroxyethyl)pyridine 1-oxide (50 mg, 0.119 mmol), 3-(3-(dimethylcarbamoyl)-phenylsulfonamido)thiophene-2-carboxylic acid (Int. 80, 127 mg, 0.357 mmol), DMAP (17.44 mg, 0.143 mmol) and EDC (228 mg, 1.190 mmol) were dissolved in DMF. The reaction was stirred at RT for 8 hours to achieve completion. The reaction mixture was diluted with water, and the precipitate was washed with water, dissolved in AcOEt and extracted with HCl 1N, Na2CO3 sat. sol. and brine. The organic phase was dried over Na2SO4 and concentrated under vacuum. The crude product was purified by preparative HPLC-method 1 to give (S)-3,5-dichloro-4-(2-(3-(cyclopropylmethoxy)-4-(difluoromethoxy)phenyl)-2-(3-(3-(dimethylcarbamoyl)phenylsulfonamido)-thiophene-2-carbonyloxy)ethyl)pyridine 1-oxide (Compound 81, 40 mg, 0.053 mmol).

Example 16

Synthesis of (S)-3,5-dichloro-4-(2-(4-(difluoromethoxy)-3-methoxyphenyl)-2-(thiophene-2-carbonyloxy)ethyl)pyridine 1-oxide (Compound 84)

Scheme 16

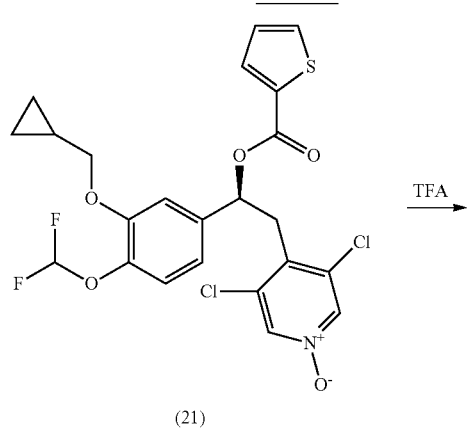

(21)

TFA →

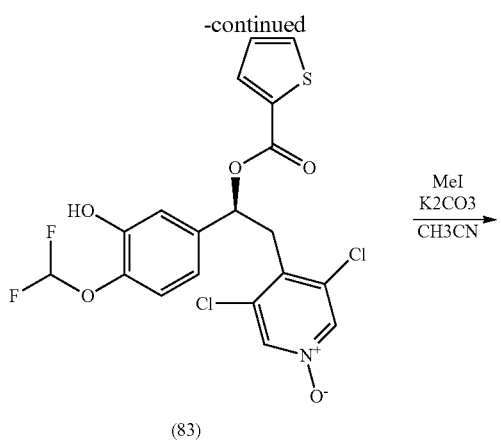

(83)

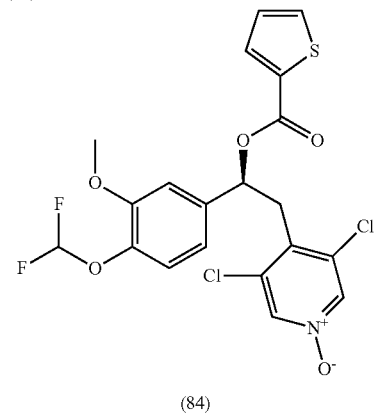

(84)

Step 1. Synthesis of (S)-3,5-dichloro-4-(2-(4-(difluoromethoxy)-3-hydroxyphenyl)-2-(thiophene-2-carbonyloxy)ethyl)pyridine 1-oxide (Intermediate 83)

(S)-3,5-dichloro-4-(2-(3-(cyclopropylmethoxy)-4-(difluoromethoxy)phenyl)-2-(thiophene-2-carbonyloxy)ethyl) pyridine 1-oxide (180 mg, 0.339 mmol) (Compound 21), prepared as previously described in Example 5, Scheme 5, Table 3, was treated with trifluoroacetic acid (TFA) (4 mL, 51.9 mmol), and the resulting solution was stirred at room temperature for 2.5 hours. The reaction mixture was diluted with CH2Cl2 (40 mL) and washed with water (3×40 mL). The organic layer was died over Na2SO4 and evaporated to dryness. The residue was purified by chromatography on SiO$_2$ (CH2Cl2:AcOEt=3:2) to afford (S)-3,5-dichloro-4-(2-(4-(difluoromethoxy)-3-hydroxyphenyl)-2-(thiophene-2-carbonyloxy)ethyl)pyridine 1-oxide (83) (67 mg, 0.141 mmol, 41.4% yield, MS/ESI$^+$474.99 [MH]$^+$)

Step 2. Synthesis of (S)-3,5-dichloro-4-(2-(4-(difluoromethoxy)-3-methoxyphenyl)-2-(thiophene-2-carbonyloxy)ethyl)pyridine 1-oxide (Compound 84)

A suspension of (S)-3,5-dichloro-4-(2-(4-(difluoromethoxy)-3-hydroxyphenyl)-2-(thiophene-2-carbonyloxy)ethyl)pyridine-1-oxide (67 mg, 0.141 mmol) (83), potassium carbonate (38.9 mg, 0.281 mmol) and methyl iodide (0.018 ml, 0.281 mmol) in acetonitrile (10 ml) was vigorously stirred at room temperature for 24 hours. More potassium carbonate (38.9 mg, 0.281 mmol) and methyl iodide (0.018 ml, 0.281 mmol) were added, and the mixture was stirred at room temperature for additional 24 hours. The reaction mixture Solid K2CO3 was filtered off, the residue was concentrated in vacuum and purified by preparative HPLC— Method 3. The collected fraction were evaporated to dryness to afford (S)-3,5-dichloro-4-(2-(4-(difluoromethoxy)-3-methoxyphenyl)-2-(thiophene-2-carbonyloxy)ethyl)pyridine 1-oxide (compound 84) (37 mg, 0.075 mmol, 54.1% yield, MS/ESI$^+$489.97 [MH]$^+$, $[\alpha_D]$=−23.00, c=0.49, DCM).

$^1$H NMR (300 MHz, DMSO-d$_6$) δ ppm 8.56 (s, 2H), 7.99 (dd, 1H), 7.86 (dd, 1H), 7.19-7.26 (m, 3H), 7.07 (dd, 1H), 7.06 (t, 1H), 6.19 (dd, 1H), 3.86 (s, 3H), 3.60 (dd, 1H), 3.35 (dd, 1H).

Pharmacological Activity of the Compounds of the Present Invention

Example 17

In Vitro Determination of PDE4 Inhibitory Activity in the Cell Free Assay

PDE4 activity was determined in U937 human monocytic supernatants cells lysate. Cells were cultured, harvested and supernatant fraction prepared essentially as described in Torphy T J et al J. Pharmacol. Exp. Ther. 1992; 263:1195-1205, which is incorporated herein by reference in its entirety. U937 cells (Cell Bank, Interlab Cell Line Collection, ICLC HTL94002) were grown at 37° C., 5% CO$_2$ in RPMI 1640 with GlutaMAX™-I medium supplemented with 10% fetal bovine serum and 100 µg/ml Pen-strep (Gibco). Cells were harvested and washed twice by centrifugation (150×g, 8 minutes) in cold PBS. Washed cells were resuspended in cold Krebs-Ringer-Henseleit buffer at a final concentration 20×10$^6$ cells/ml and sonicated. After centrifugation at 15000×g for 20 minutes, the supernatants were pooled, divided in aliquots and stored at −80° C.

PDE4 activity was determined in cells supernatants by assaying cAMP disappearance from the incubation mixtures. The concentration of the test compounds ranged between 10$^{-12}$ M and 10$^{-6}$ M. Reactions were stopped by enzyme heat inactivation (2.5 minutes at 100° C.) and residual cAMP content was determined using the 'LANCE cAMP Assay' from PerkinElmer following the providers instructions. Percentage of inhibition of PDE4 activity was calculated, assuming cAMP disappearance in the absence of inhibitors as 100% and cAMP disappearance in heat inactivated samples as 0%.

The results of the tested compounds, representatives of the invention, expressed as mean±standard deviation of the nM concentration of the test compound producing 50% inhibition of cAMP disappearance (IC$_{50}$), were less than 2.5 nM. For a group of preferred compounds (27 out of the 30 tested) the results were less than 0.5 nM. For a group of more preferred compounds (6 out of the 30 tested) the results were less than 0.05 nM.

Example 18

In Vitro Determination of PDE4 Inhibitory Activity in the Peripheral Blood Mononuclear Cells (PBMCs) Assay The assay, which is based on the known inhibitory activity exerted by PDE4 inhibitors on the lipopolyshaccarides (LPS)-induced tumour necrosis factor-alpha (TNF-α release in peripheral blood mononuclear cells (PBMCs), was performed according to a method previously described (Hatzelmann A et al J. Pharmacol. Exp. Ther. 2001; 297:267-279 and Draheim R et al. J. Pharmacol. Exp. Ther. 2004; 308:555-563, both of which are incorporated herein by reference in their entireties). Cryopreserved human PBMCs, (100 µl/well) were incubated in 96-well plates (10$^5$ cells/well), for 30 min, in the presence or absence (50 microl) of the test compounds whose concentrations ranged from 10$^{-12}$ M to 10$^{-6}$ M or from 10$^{-13}$ M to 10$^{-7}$ M. Subsequently, LPS (3 ng/ml) was added. After 18 hours, incubation at 37° C. in a humidified incubator under an atmosphere of 95% air and 5% CO$_2$, culture medium was collected and TNF-α measured by ELISA.

The effects of the tested compounds were calculated as percentage of inhibition of TNF-α release, assuming LPS-induced TNF-α production in the absence of inhibitor compound as 100% and basal TNF-α production of PBMCs in the absence of LPS as 0%. The results of the tested compounds, representatives of the invention, expressed as mean±95% confidence limits of the molar concentration of the test compound producing 50% inhibition of LPS-induced TNF-α release (IC$_{50}$) were less than 33 nM. For a group of preferred compounds, the results were less than 1 nM. For a group of further preferred compounds, the results were less than 0.1 nM.

Example 19

In Vitro Determination of Intrinsic Clearance in Human Hepatic Microsomes

Method a)

Test compounds in duplicate at the final concentration of 1 µM are dissolved in DMSO (DMSO final concentration 0.5% v/v) and pre-incubated for 10 minutes at 37° C. in potassium phosphate buffer pH 7.4, 3 mM MgCl$_2$, with liver microsomes at the final concentration of 0.5 mg/ml. After the pre-incubation period, reactions are started by adding the cofactors mixture (NADP, Glc6P, Glc6P-DH); samples are taken at time 0, 5, 10, 15, 20 and 30 minutes, added to acetonitrile to stop reaction and centrifuged. The supernatants are analyzed and quantified by LC-MS/MS.

A control sample without cofactors is always added in order to check the stability of test compounds in the matrix. 7-Ethoxycoumarin is added as reference standard. A fixed concentration of verapamil is added in every sample as internal standard for LC-MS/MS. Zero-time incubation is used as 100% value. Percent loss of substrate in incubation is determined to estimate in-vitro half life and in-vitro intrinsic clearance of compounds. The rate constant, k (min$^{-1}$) derived for the exponential decay equation (peak area vs time) is used to calculate the rate of intrinsic clearance (CLi) of the compounds using the following equation:

$$CLi \text{ (mL/min/g liver)} = k \times V \times y$$

Where:
k is calculated from the exponential fitting decay of the area values
V=incubation volume (mL)/mg protein
y=microsomal protein yield=52.5 mg/g liver Compounds of the invention are endowed with high or moderate intrinsic metabolic clearance. Some of the representative compounds of the invention, when tested according to the protocol, showed an intrinsic Clearance>15 mL/min/g.

Method b)

Test compounds are incubated, in duplicate, at the concentration of 1 μM with liver microsomes (0.8 mg protein/mL) in Dulbecco's KHB buffer (pH 7.4) at 37° C. in the presence of 1 mM NADPH. At different time points (0, 5, 10, 20, 30 and 60 minutes) 50 μL aliquots of the incubates are taken, added with 80 μL of ice-cold acetonitrile and 20 μL of 1 μM warfarin in acetonitrile (injection check) to stop the reaction and samples centrifuged. The supernatant is analysed by LC-MS/MS for unchanged compounds.

Test compounds are incubated with liver microsomes in Dulbecco's KHB buffer in the absence of NADPH for 0 and 60 minutes, as control. Midazolam at the concentration of 1 μM, is incubated with microsomes as positive control for phase I activity of microsomes. Control samples are processed as test compounds samples.

The intrinsic clearance is determined using the half-life approach. The half-life is calculated from the relationship:

$$\text{Half-life (min)} = \frac{LN(2)}{-\text{SLOPE}} = \frac{0.693}{-\text{SLOPE}}$$

The slope refers to the curve obtained by plotting the natural logarithmic (LN) value of peak area of the compound remaining against the time and is calculated by linear regression analysis.

Results are reported as half-life in minutes and as in vitro intrinsic clearance values expressed in μL/min/mg protein (for incubation with microsomes). Compounds of the invention are endowed with high or moderate intrinsic metabolic clearance. Some of the representative compounds of the invention, when tested according to the protocol, showed an intrinsic Clearance>300 μL/min/mg and a half life<3 minutes.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. An N-oxide compound of formula (IA):

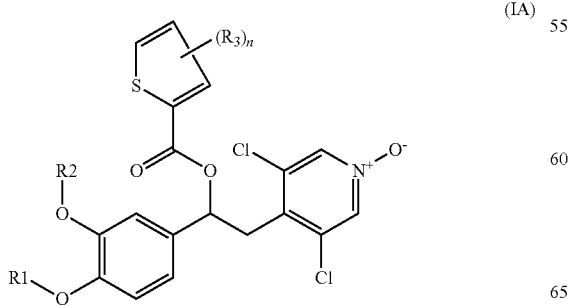

(IA)

wherein:
$R_1$ and $R_2$ are different or the same and are each independently:
H;
$(C_1-C_6)$ haloalkyl
$(C_1-C_6)$ alkyl, optionally substituted by one or more substituents selected from $(C_3-C_7)$ cycloalkyl or $(C_5-C_7)$ cycloalkenyl;
$(C_3-C_7)$ cycloalkyl;
$(C_5-C_7)$ cycloalkenyl;
$(C_2-C_6)$ alkenyl; or
$(C_2-C_6)$ alkynyl;
n is 0, 1 or 2;
$R_3$ is an optional substituent which, at each occurrence, is independently:
$(C_1-C_6)$ alkyl optionally substituted by one or more $(C_3-C_7)$ cycloalkyl;
$(C_1-C_6)$ haloalkyl;
$OR_4$ wherein $R_4$ is selected from the group consisting of H, $(C_1-C_{10})$ alkyl optionally substituted by $(C_3-C_7)$ cycloalkyl, $(C_1-C_6)$ haloalkyl, $(C_3-C_7)$ cycloalkyl;
a halogen atom;
a group —$NR_5SO_2R_6$ wherein
$R_5$ is selected in the group consisting of hydrogen; $(C_1-C_6)$ alkyl; $(C_1-C_6)$ alkyl which is substituted by a group —$NR_7R_8$ wherein $R_7$ and $R_8$ are independently H, $(C_1-C_6)$ alkyl, or together with the nitrogen atom to which they are attached form a $(C_5-C_7)$ heterocycloalkyl group; $(C_1-C_6)$ alkyl which is substituted by an heteroaryl group; and
$R_6$ is $(C_1-C_4)$ alkyl optionally substituted by $(C_3-C_7)$ cycloalkyl; or a phenyl ring optionally substituted with one or two halogen atoms, hydroxy, $(C_1-C_4)$ alkyl or $(C_1-C_4)$ alkoxy groups or with a group —$C(O)NR_9R_{10}$ wherein $R_9$ and $R_{10}$ are independently hydrogen, $(C_1-C_4)$ alkyl groups, or together with the nitrogen atom to which they are attached form a $(C_5-C_7)$ heterocycloalkyl group;
a group —$SO_2R_{11}$ wherein
$R_{11}$ is selected from $(C_1-C_6)$ alkyl; a phenyl ring which is optionally substituted with one or two groups selected in the list consisting of: halogen atom, hydroxyl, $(C_1-C_4)$ alkyl, $(C_1-C_4)$ alkoxy, a —$C(O)NR_{12}R_{13}$ group, wherein $R_{12}$ and $R_{13}$ are independently hydrogen, $(C_1-C_4)$ alkyl groups, or together with the nitrogen atom to which they are attached form a $(C_5-C_7)$ heterocycloalkyl group, and a group —$NR_{14}R_{15}$, wherein $R_{14}$ and $R_{15}$ are independently hydrogen, $(C_1-C_4)$ alkyl groups, or together with the nitrogen atom to which they are attached form a $(C_5-C_7)$ heterocycloalkyl group;
a group —$C(O)R_{16}$ wherein
$R_{16}$ is a phenyl ring which is optionally substituted with one or two groups selected in the list consisting of: halogen atom, hydroxyl, $(C_1-C_4)$ alkyl, $(C_1-C_4)$ alkoxy, a —$C(O)NR_{23}R_{24}$ group wherein $R_{23}$ and $R_{24}$ are independently hydrogen, $(C_1-C_4)$ alkyl groups, or together with the nitrogen atom to which they are attached form a $(C_5-C_7)$ heterocycloalkyl group, and a group —$NR_{25}R_{26}$, wherein $R_{25}$ and $R_{26}$ are independently hydrogen, $(C_1-C_4)$ alkyl groups, or together with the nitrogen atom to which they are attached form a ($C_5$-$C_7$) heterocycloalkyl group; or a group —$SO_2NR_{17}R_{18}$ wherein
$R_{17}$ is H or ($C_1$-$C_6$) alkyl; and
$R_{18}$ is selected from hydrogen; ($C_1$-$C_6$)alkyl; ($C_1$-$C_6$) alkyl which is substituted by a group —$NR_{19}R_{20}$ wherein $R_{19}$ and $R_{20}$ are independently H or ($C_1$-$C_6$) alkyl, or together with the nitrogen atom to which they are attached form a ($C_5$-$C_7$)heterocycloalkyl group; a phenyl ring optionally substituted with one or two halogen atoms, hydroxy, ($C_1$-$C_4$) alkyl or ($C_1$-$C_4$) alkoxy groups or with a group —$C(O)NR_{21}R_{22}$ wherein $R_{21}$ and $R_{22}$ are independently hydrogen, ($C_1$-$C_4$) alkyl groups, or together with the nitrogen atom to which they are attached form a ($C_5$-$C_7$) heterocycloalkyl group;

or a pharmaceutically acceptable salt thereof.

2. An N-oxide compound or pharmaceutically acceptable salt according to claim 1, wherein $R_1$ is ($C_1$-$C_6$) haloalkyl and $R_2$ is ($C_1$-$C_6$) alkyl which is substituted by ($C_3$-$C_7$) cycloalkyl.

3. An N-oxide compound or pharmaceutically acceptable salt according to claim 1, which has the absolute configuration of carbon (1) shown in formula (IA)':

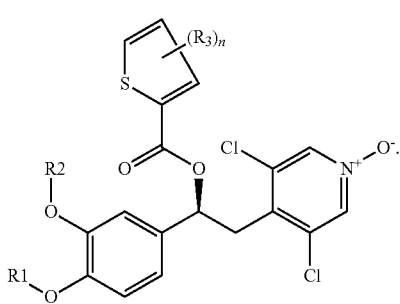

4. An N-oxide compound, which is selected from the group consisting of:
(S)-3,5-dichloro-4-(2-(3-(cyclopropylmethoxy)-4-(difluoromethoxy)-phenyl)-2-(thiophene-3-carbonyloxy) ethyl)pyridine 1-oxide;
(S)-3,5-dichloro-4-(2-(3-(cyclopropylmethoxy)-4-(difluoromethoxy)-phenyl)-2-(thiophene-2-carbonyloxy) ethyl)pyridine 1-oxide;
(S)-3,5-dichloro-4-(2-(3-(cyclopropylmethoxy)-4-(difluoromethoxy)-phenyl)-2-(5-methylthiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-methoxythiophene-2-carbonyloxy)ethyl)pyridine 1-oxide;
(S)-3,5-dichloro-4-(2-(5-chlorothiophene-2-carbonyloxy)-2-(3-(cyclopropylmethoxy)-4-(difluoromethoxy) phenyl)ethyl)pyridine 1-oxide;
(S)-3,5-dichloro-4-(2-(3-chloro-4-(methylsulfonyl)thiophene-2-carbonyloxy)-2-(3-(cyclopropylmethoxy)-4-(difluoromethoxy)phenyl)-ethyl)pyridine 1-oxide;
(S)-3,5-dichloro-4-(2-(3-(cyclopropylmethoxy)-4-(difluoromethoxy)-phenyl)-2-(5-methoxythiophene-2-carbonyloxy)ethyl)pyridine 1-oxide;
(S)-3,5-dichloro-4-(2-(3-(cyclopropylmethoxy)-4-(difluoromethoxy)-phenyl)-2-(4,5-dimethylthiophene-2-carbonyloxy)ethyl)pyridine 1-oxide;
(S)-3,5-dichloro-4-(2-(3-chlorothiophene-2-carbonyloxy)-2-(3-(cyclopropylmethoxy)-4-(difluoromethoxy) phenyl)ethyl)pyridine 1-oxide;
(S)-3,5-dichloro-4-(2-(3-(cyclopropylmethoxy)-4-(difluoromethoxy)-phenyl)-2-(3-(N-methylsulfamoyl) thiophene-2-carbonyloxy)ethyl)pyridine 1-oxide;
(S)-3,5-dichloro-4-(2-(3-(cyclopropylmethoxy)-4-(difluoromethoxy)-phenyl)-2-(3-(N-methyl-N-(2-morpholinoethyl)sulfamoyl)thiophene-2-carbonyloxy) ethyl)pyridine 1-oxide;
(S)-3,5-dichloro-4-(2-(3-(cyclopropylmethoxy)-4-(difluoromethoxy)-phenyl)-2-(3-(N-(2-morpholinoethyl) methylsulfonamido)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(3-(methylsulfonamido)thiophene-2-carbonyloxy)ethyl)pyridine 1-oxide;
(S)-3,5-dichloro-4-(2-(3-(cyclopropylmethoxy)-4-(difluoromethoxy)-phenyl)-2-(5-(N-(2-morpholinoethyl) methylsulfonamido)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(4-(methylsulfonamido)thiophene-2-carbonyloxy)ethyl)pyridine 1-oxide;
(S)-3,5-dichloro-4-(2-(4-(4-chlorophenylsulfonyl)thiophene-3-carbonyloxy)-2-(3-(cyclopropylmethoxy)-4-(difluoromethoxy)phenyl)ethyl)-pyridine 1-oxide;
(S)-4-(2-(3-benzoylthiophene-2-carbonyloxy)-2-(3-(cyclopropylmethoxy)-4-(difluoromethoxy)phenyl)ethyl)-3,5-dichloropyridine 1-oxide;
(S)-3,5-dichloro-4-(2-(3-(cyclopropylmethoxy)-4-(difluoromethoxy)-phenyl)-2-(3-(3-(dimethylcarbamoyl) phenylsulfonamido)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(5-(N-(3-(dimethylcarbamoyl)phenyl)sulfamoyl)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(5-(N-(4-(dimethylcarbamoyl)phenyl)sulfamoyl)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(5-(N-(pyridin-3-ylmethyl) methylsulfonamido)thiophene-2-carbonyloxy)ethyl) pyridine 1-oxide;
(S)-3,5-dichloro-4-(2-(3-(cyclopropylmethoxy)-4-(difluoromethoxy)-phenyl)-2-(5-(N-(2-(pyrrolidin-1-yl) ethyl)methylsulfonamido)thiophene-2-carbonyloxy) ethyl)pyridine 1-oxide;
(S)-3,5-dichloro-4-(2-(3-(cyclopropylmethoxy)-4-(difluoromethoxy)-phenyl)-2-(4-methoxy-5-(N-(2-morpholinoethyl)methylsulfonamido)-thiophene-2-carbonyloxy)ethyl)pyridine 1-oxide;
(S)-3,5-dichloro-4-(2-(5-(1-cyclopropyl-N-(2-morpholinoethyl)-methylsulfonamido)thiophene-2-carbonyloxy)-2-(3-(cyclopropylmethoxy)-4-(difluoromethoxy) phenyl)ethyl)pyridine 1-oxide;
(S)-3,5-dichloro-4-(2-(5-(1-cyclopropyl-N-(2-(pyrrolidin-1-yl)ethyl)-methylsulfonamido)thiophene-2-carbonyloxy)-2-(3-(cyclopropylmethoxy)-4-(difluoromethoxy)phenyl)ethyl)pyridine 1-oxide;
(S)-3,5-dichloro-4-(2-(3,4-dimethoxyphenyl)-2-(thiophene-2-carbonyloxy)ethyl)pyridine 1-oxide; and
(S)-3,5-dichloro-4-(2-(4-(difluoromethoxy)-3-methoxyphenyl)-2-(thiophene-2-carbonyloxy)ethyl)pyridine 1-oxide;

or a pharmaceutically acceptable salt of said N-oxide compound.

5. A combination, comprising an N-oxide compound or pharmaceutically acceptable salt according to claim 1 and a second pharmaceutical active component selected from the group consisting of beta2-agonist, a corticosteroid, and an antimuscarinic agent.

6. A pharmaceutical composition, comprising an N-oxide compound or pharmaceutically acceptable salt according to claim 1 and one or more pharmaceutically acceptable carriers and/or excipients.

7. A pharmaceutical composition, comprising a combination according to claim 5 and one or more pharmaceutically acceptable carriers and/or excipients.

8. A kit, comprising a pharmaceutical composition according to claim 6 and a device which is selected from a single- or multi-dose dry powder inhaler, a metered dose inhaler or a nebulizer.

9. A pharmaceutical composition, comprising an N-oxide compound or pharmaceutically acceptable salt according to claim 2 and one or more pharmaceutically acceptable carriers and/or excipients.

10. A pharmaceutical composition, comprising an N-oxide compound or pharmaceutically acceptable salt according to claim 3 and one or more pharmaceutically acceptable carriers and/or excipients.

11. A pharmaceutical composition, comprising an N-oxide compound or pharmaceutically acceptable salt according to claim 4 and one or more pharmaceutically acceptable carriers and/or excipients.

* * * * *